(12) United States Patent
Quay

(10) Patent No.: US 12,576,103 B2

(45) Date of Patent: Mar. 17, 2026

(54) HEPARIN AND N-ACETYLCYSTEINE FOR THE TREATMENT OF LUNG INJURY

(71) Applicant: Atossa Therapeutics, Inc., Seattle, WA (US)

(72) Inventor: Steven C. Quay, Seattle, WA (US)

(73) Assignee: Atossa Therapeutics, Inc., Seattle, WA (US)

( * ) Notice: Subject to any disclaimer, the term of this patent is extended or adjusted under 35 U.S.C. 154(b) by 515 days.

(21) Appl. No.: 17/802,711

(22) PCT Filed: Mar. 19, 2021

(86) PCT No.: PCT/US2021/023256

§ 371 (c)(1),
(2) Date: Aug. 26, 2022

(87) PCT Pub. No.: WO2021/194890

PCT Pub. Date: Sep. 30, 2021

(65) Prior Publication Data

US 2023/0110614 A1 Apr. 13, 2023

Related U.S. Application Data

(60) Provisional application No. 63/038,092, filed on Jun. 11, 2020, provisional application No. 63/026,674, filed on May 18, 2020, provisional application No. 63/011,287, filed on Apr. 16, 2020, provisional application No. 63/006,050, filed on Apr. 6, 2020, provisional application No. 63/001,344, filed on Mar. 29, 2020, provisional application No. 62/993,644, filed on Mar. 23, 2020.

(51) Int. Cl.
| | |
|---|---|
| *A61K 31/727* | (2006.01) |
| *A61K 9/00* | (2006.01) |
| *A61K 31/198* | (2006.01) |
| *A61K 45/06* | (2006.01) |
| *A61K 47/18* | (2017.01) |

(52) U.S. Cl.
CPC .......... *A61K 31/727* (2013.01); *A61K 9/0078* (2013.01); *A61K 31/198* (2013.01); *A61K 45/06* (2013.01); *A61K 47/183* (2013.01)

(58) Field of Classification Search
CPC .. A61K 31/727; A61K 9/0078; A61K 31/198; A61K 45/06; A61K 47/183
USPC ......................................................... 514/56
See application file for complete search history.

(56) References Cited

U.S. PATENT DOCUMENTS

| | | |
|---|---|---|
| 4,511,069 A | 4/1985 | Kalat |
| 5,681,811 A | 10/1997 | Ekwuribe |
| 10,301,377 B2 | 5/2019 | Graham et al. |
| 2006/0229276 A1 | 10/2006 | Hook et al. |

| | | |
|---|---|---|
| 2009/0061411 A1 | 3/2009 | Venkataraman et al. |
| 2010/0143312 A1* | 6/2010 | Hariri .................... A61K 35/50 |
| | | 424/93.7 |
| 2014/0288267 A1 | 9/2014 | Tripp et al. |

FOREIGN PATENT DOCUMENTS

| | | |
|---|---|---|
| CN | 107653228 A | 2/2018 |
| WO | WO-2005020885 A2 | 3/2005 |
| WO | WO-2016120787 A1 | 8/2016 |

OTHER PUBLICATIONS

Kummarapurugu et al. Molecular principles for heparin oligosaccharide-based inhibition of neutrophil elastase in cystic fibrosis. J. Biol. Chem. (2018) 293(32) 12480-12490. (Year: 2018).*

Elsharnouby et al. Heparin/N-acetylcysteine: An adjuvant in the management of burn inhalation injury: A study of different doses. Journal of Critical Care 29 (2014) 182.e1-182.e4. (Year: 2014).*

Andersen K., et al., "The Proximal Origin of SARS-CoV-2," Nature medicine 26.4 (2020): 450-452.

Ashraf U., et al., "Nebulized Heparin and N-Acetylcysteine for Smoke Inhalational Injury," Clinical Case Report, Medicine, vol. 97, No. 19, e0638, 2018, pp. 1-4.

Barbucci R., et al., "Swelling Behavior of Carboxymethylcellulose Hydrogels in Relation to Cross-Linking, pH, and Charge Density," Macromolecules, vol. 33(20), pp. 7475-7480. (2000).

Battle., et al., "Soluble Angiotensin-Converting Enzyme 2: a Potential Approach for Coronavirus Infection Therapy?," Clinical Science, vol. 134(5), Mar. 13, 2020, pp. 543-545.

Becker G.I., et al., "Highly Potent Inhibitors of Proprotein Convertase Furin as Potential Drugs for Treatment of Infectious Diseases," Journal of Biological Chemistry, vol. 287(26), Jun. 22, 2012, pp. 21992-22003.

Belouzard S., et al., "Activation of the SARS Coronavirus Spike Protein via Sequential Proteolytic Cleavage at Two Distinct Sites," Proceedings of the National Academy of Sciences 106.14 (2009): 5871-5876.

Bendstrup K.E., et al., "Effect of inhaled heparin on lung function and coagulation in healthy volunteers," European Respiratory Journal 19.4 (2002): 606-610.

Bendstrup K.E., et al., "Inhaled Heparin is Effective in Exacerbations of Asthma," Respiratory Medicine, Feb. 2000, vol. 94, No. 2, pp. 174-175.

Borsig L., "Heparin as in Inhibitor of Cancer Progression," Progress in Molecular Biology and Translational Science, vol. 93, 2010, pp. 335-349.

Cao Y., et al., "Comparative Genetic Analysis of the Novel Coronavirus (2019-nCoV/SARS-CoV-2) Receptor ACE2 in Different Populations," Cell Discovery, 2020, vol. 6(11), 4 pages.

(Continued)

*Primary Examiner* — Yih-Horng Shiao

(74) *Attorney, Agent, or Firm* — Kilpatrick Towsend & Stockton LLP

(57) ABSTRACT

Disclosed herein are compositions and methods for treatment or prevention of a respiratory viral infection. A composition of the present disclosure comprises one or more of heparin, or N-acetylcysteine. A composition for treatment or prevention of a respiratory viral infection may be administered by inhalation in intervals. Administration of a composition may treat or prevent a viral infection.

16 Claims, 7 Drawing Sheets

(56)    References Cited

OTHER PUBLICATIONS

Cazzola M., et al., "Influence of N-acetylcysteine on Chronic Bronchitis or COPD Exacerbations: a Meta-Analysis," European Respiratory Society, 2015, vol. 24, pp. 451-461.

Chen C., et al., "Cryo-EM structure of eastern equine encephalitis virus in complex with heparan sulfate analogues," Proceedings of the National Academy of Sciences 117.16 (2020): 8890-8899.

Choy K., et al., "Remdesivir, Lopinavir, Emetine, and Homoharringtonine Inhibit SARS-CoV-2 Replication in Vitro," Antiviral research 178 (2020): 104786, 5 pages.

Coutard B., et al., "The spike glycoprotein of the new coronavirus 2019-nCoV contains a furin-like cleavage site absent in CoV of the same clade," Antiviral research 176 (2020): 104742, 6 pages.

Desai M.H., et al., "Reduction in mortality in pediatric patients with inhalation injury with aerosolized heparin/N-acetylcystine [correction of acetylcystine] therapy," Journal of Burn Care & Rehabilitation, May 1998, vol. 19(3), pp. 210-212.

Feng F., et al., "Efficacy and safety of N-acetylcysteine therapy for idiopathic pulmonary fibrosis: An updated systematic review and meta-analysis," Experimental and therapeutic medicine 18.1 (2019): 802-816.

Gautret P., et al., "Hydroxychloroquine and Azithromycin as a Treatment of COVID-19: Results of an Open-Label Non-randomized Clinical Trial," International journal of antimicrobial agents (2020): 105949, 24 pages.

Haan C.A.M.D., et al., "Cleavage of Group 1 Coronavirus Spike Proteins: How Furin Cleavage Is Traded off against Heparan Sulfate Binding upon Cell Culture Adaptation," Journal of Virology, vol. 82(12), pp. 6078-6083, (2008).

Haan C.A.M.D., et al., "Murine Coronavirus with an Extended Host Range Uses Heparan Sulfate as an Entry Receptor," Journal of Virology, Nov. 2005, vol. 79(22), pp. 14451-14456.

Haeger S.M., et al., "Heparan Sulfate in the Developing, Healthy, and Injured Lung," American Journal of Respiratory Cell and Molecular Biology, 2016, vol. 55(1) pp. 5-11.

Hamahata A., et al., "Gamma-Tocopherol Nebulization by a Lipid Aerosolization Device Improves Pulmonary Function in Sheep with Burn and Smoke Inhalation Injury," Free Radical Biology & Medicine, Aug. 15, 2009, vol. 45(4) pp. 425-433.

Hardes K., et al., "Novel Furin Inhibitors with Potent Anti-infectious Activity," ChemMedChem, 2015, vol. 10(7), pp. 1218-1231.

Huang X., et al., "Human Coronavirus HKU1 Spike Protein Uses O-Acetylated Sialic Acid as an Attachment Receptor Determinant and Employs Hemagglutinin-Esterase Protein as a Receptor-Destroying Enzyme," Journal of Virology, Jul. 2015, vol. 89(14), pp. 7202-7213.

International Search Report and Written Opinion for International Application No. PCT/US2021/023256, mailed May 26, 2021, 10 pages.

Izaguirre G., "The Proteolytic Regulation of Virus Cell Entry by Furin and Other Proprotein Convertases," Viruses, 2011, vol. 11(9): 837, 19 pages.

Jia H.P., et al., "Ectodomain Shedding of Angiotensin Converting Enzyme 2 in Human Airway Epithelia," American Journal of Physiology Lung Cellular and Molecular Physiology, 2009, vol. 297, pp. l.84-l.96.

Jin Z., et al., "Structure of M pro from SARS-CoV-2 and Discovery of its Inhibitors," Nature (2020), 24 pages.

Juschten J., et al., "Nebulized anticoagulants in lung injury in critically ill patients—an updated systematic review of preclinical and clinical studies," Annals of Translational Medicine, Nov. 2017, vol. 5(22):444, 12 pages.

Kahler Z.P., et al., "Cost of Treating Venous Thromboembolism with Heparin and Warfarin Versus Home Treatment With Rivaroxaban," Academic Emergency Medicine, 2015, vol. 22(7), pp. 796-802.

Kent L.H., t al., "Physico-chemical studies of poly-d-glutamic acid from Bacillus anthracis grown in vitro," Microbiological Research Establishment, Jun. 6, 1957, vol. 250, pp. 1-43.

Lang J., et al., "Inhibition of SARS Pseudovirus Cell Entry by Lactoferrin Binding to Heparan Sulfate Proteoglycans," PLoS One, 2011, 11 pages.

Latorre R., et al., "Voltage-Dependent Conductance Induced by aLamethicin-phospholipid Conjugates in Lipid Bilayers," Biophysical journal 36.3 (1981), 803-809.

Lee M "Heparin inhibits activation of latent transforming growth factor-β1," Pharmacology 92.5-6 (2013): 238-244.

Li H., et al., "The use of sodium carboxymethylcellulose in the preparation of spray-dried proteins for pulmonary drug delivery," European Journal of Pharmaceutical Sciences, 2010, vol. 40, pp. 56-61.

Lin L., et al., "Hypothesis for Potential Pathogenesis of SARS-CoV-2 Infection—a Review of Immune Changes in Patients with Viral Pneumonia," Emerging Microbes & Infections, 9.1 (2020), 727-732.

Liu H., et al., "Lessons Learned from the Contamination of Heparin," Natural Product Reports, Mar. 2009, vol. 26(3), 22 pages.

Lukassen S., et al., "SARS-CoV-2 Receptor ACE 2 and TMPRSS 2 are Primarily Expressed in Bronchial Transient Secretory Cells," The EMBO journal 39.10 (2020): e105114, 15 pages.

Ma S.N., et al., "The Anti-Cancer Properties of Heparin and its Derivatives: A Review and Prospect," Cell Adhesion & Migration, vol. 14, No. 1, 2020, pp. 118-128.

Manning M.C., et al., "Stability of Protein Pharmaceuticals," Pharmaceutical Research, 1989, vol. 6 (11), pp. 903-918.

McIntire A.M., et al., "Outcomes following the use of nebulized heparin for inhalation injury (HIHI Study)," Journal of Burn Care & Research 38.1 (2017): 45-52.

Milewska A., et al., "Human Coronavirus NL63 Utilizes Heparan Sulfate Proteoglycans for Attachment to Target Cells," Journal of Virology, 2014, vol. 88(22), pp. 13221-13230.

Molina J.M., et al., "No Evidence of Rapid Antiviral Clearance or Clinical Benefit with the Combination of Hydroxychloroquine and Azithromycin in Patients with Severe COVID-19 Infection," Med Mal Infect 50.384 (2020), pp. 30085-30088.

Mu S., et al., "Unfractionated heparin ameliorates pulmonary microvascular endothelial barrier dysfunction via microtubule stabilization in acute lung injury," Respiratory research 19.1 (2018): 220, 15 pages.

Mycroft-West C., et al., "The 2019 Coronavirus (SARS-CoV-2) Surface Protein (Spike) S1 Receptor Binding Domain Undergoes Conformational Change upon Heparin Binding," BioRxiv (2020), 9 pages.

Paborji M., et al., "Chemical and Physical Stability of Chimeric L6, a Mouse-Human Monoclonal Antibody," Pharmaceutical Research, May 1994, vol. 11(5), pp. 764-771.

Peng M., et al., "Luteolin Restricts Dengue Virus Replication Through Inhibition of the Proprotein Convertase Furin," 2017, vol. 143, 48 pages.

Pramanick et al. "Excipient Selection In Parenteral Formulation Development" Mar. 2013, Pharma Times 45(3):65-77.

Quay S.C., et al., "Conformational studies of aqueous melittin: thermodynamic parameters of the monomer-tetramer self-association reaction," Biochemistry 22.3 (1983): 695-700.

Quay S.C., et al., "Molecular mechanisms of alamethicin channel gating," Biophysical journal 37.1 (1982): 154-156.

Racaniello V "Furin Cleavage Site in the SARS-CoV-2 Coronavirus Glycoprotein," Virology blog, 2020, 27 pages.

Riley M., et al., "Position Statement on Heparin Safety Concerns," The Journal of Pediatric Pharmacology and Therapeutics, 2016, vol. 21(6), pp. 530-532.

Rose L.M., et al., "Development of the first inhaled antibiotic for the treatment of cystic fibrosis," Science Translational Medicine, Dec. 22, 2010; 2(63): 63mr4, 5 pages.

Sainz-Serp D., et al., "Purification of Natural Anionic Polymers," Minerva Biotecnologica, 2005, vol. 17(4), 1 page.

Schoeman D., et al., "Coronavirus Envelope Protein: Current Knowledge," Virology journal 16.1 (2019): 69. 22 pages.

Seaman M., "Sodium polyphosphate enhances the antimicrobial activities of whole and fractionated peanut skin extract against food spoilage yeasts in a model juice system," Graduate Theses and Dissertations, 2013, 90 pages.

(56)                References Cited

OTHER PUBLICATIONS

Sheahan T.P., et al., "Broad-spectrum antiviral GS-5734 inhibits both epidemic and zoonotic coronaviruses," Science translational medicine 9.396 (2017), 17 pages.

Shen W.F., et al. Epitope resurfacing on dengue virus-like particle vaccine preparation to induce broad neutralizing antibody, Elife 7 (2018): e38970, 24 pages.

Sidleychem, "Properties of Sodium Carboxymethyl Cellulose," Retrieved from Internet URL: https://celluloseether.com/properties-of-cmc-carboxymethylcellulose/, Retrieved on Jul. 15, 2020, 2 pages.

Stehli D., et al., "Collapsed State of Polyglutamic Acid Results in Amyloid Spherulite Formation," Intrinsically Disordered Proteins, 2015, vol. 3(1). 12 pages.

Sturrock E.D., et al., "Assignment of Free and Disulfide-Bonded Cysteine Residues in Testis Angiotensin-Converting Enzyme: Functional Implications," Biochemistry, 1996, vol. 35(29), pp. 9560-9566.

Thuma J.B., et al., "Choline and NMDG directly reduce outward currents: reduced outward current when these substances replace Na+ is alone not evidence of Na+-activated K+ currents," Journal of Neurophysiology, vol. 120, No. 6, pp. 3217-3233, DOI: doi.org/10.1152/jn.00871.2017.

Ullian., et al., "N-acetylcysteine decreases angiotensin II receptor binding in vascular smooth muscle cells," Journal of the American Society of Nephrology 16.8 (2005): 2346-2353.

Ulus I.H., et al., "Choline as an Agonist: Determination of its Agonistic Potency on cholinergic Receptors," Biochemical Pharmacology, 1988, vol. 37(14), pp. 2747-2755.

Verdia-Baguena C., et al., "Coronavirus E protein Forms ion Channels with Functionally and Structurally-Involved Membrane Lipids," Virology, vol. 432, 2012, pp. 485-494.

Vicenzi E., et al., "Coronaviridae and SARS-associated Coronavirus Strain HSR1," Emerging Infectious Diseases, 2004, vol. 10(3), pp. 413-418.

Wang M., et al., "Remdesivir and Chloroquine Effectively Inhibit the Recently Emerged Novel Coronavirus (2019-nCoV) in Vitro," Cell Research, vol. 30: 269-271, Feb. 4, 2020, Retrieved on May 12, 2021, Retrieved from the Internet URL: https://pubmed.ncbi.nlm.nih.gov/32020029 , 3 pages.

Yahata T., et al., "Modulation of Airway Responsiveness by Anionic and Cationic Polyelectrolyte Substances," European Journal of Pharmacology, 2002, vol. 434(1-2):71-9.

Yan S., et al., "Structural basis for the recognition of SARS-CoV-2 by full-length human ACE2," Science, vol. 367(6485), Mar. 27, 2020, pp. 1444-1448.

Yu Y., et al., "Adjuvant Therapy with Heparin in Patients with Lung Cancer without Indication for Anticoagulants: A Systematic Review of the Literature with Meta-Analysis," Journal of Cancer Research and Therapeutics, vol. 12, 2016, pp. C37-C42.

Zaretzky F.R., et al., "Sulfated Polyanions Block Chlamydia Trachomatis Infection of Cervix-Derived Human Epithelia," Infection and Immunity, Sep. 1995, vol. 63(9), pp. 3520-3526.

Zielinski M., et al., "Is inhaled heparin a viable therapeutic option in inhalation injury?," Advances in respiratory medicine 87.3 (2019): 184-188.

Lee Y-J., et al., "Suppression of Human Prostate Cancer PC-3 Cell Growth by N-Acetylcysteine Involves Over-Expression of Cyr61," Toxicology in Vitro, Elsevier Science, vol. 25, No. 1, Feb. 1, 2011, pp. 199-205.

Page C., "Heparin and Related Drugs: Beyond Anticoagulant Activity," ISRN Pharmacology, vol. 2013, Jan. 1, 2013, 14 pages.

Yip L.Y., et al., "Safety and Potential Anticoagulant Effects of Nebulised Heparin in Burns Patients with Inhalational Injury at Singapore General Hospital Burns Centre," Burns, Jul. 4, 2011, vol. 37, No. 7, XP028297499, pp. 1154-1160.

* cited by examiner

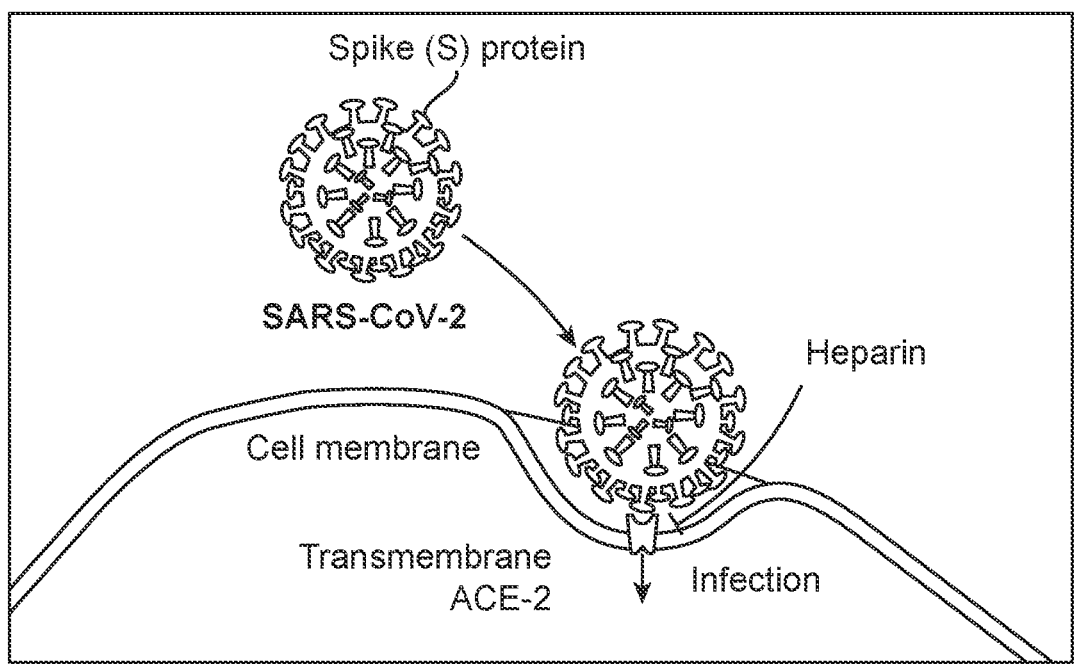
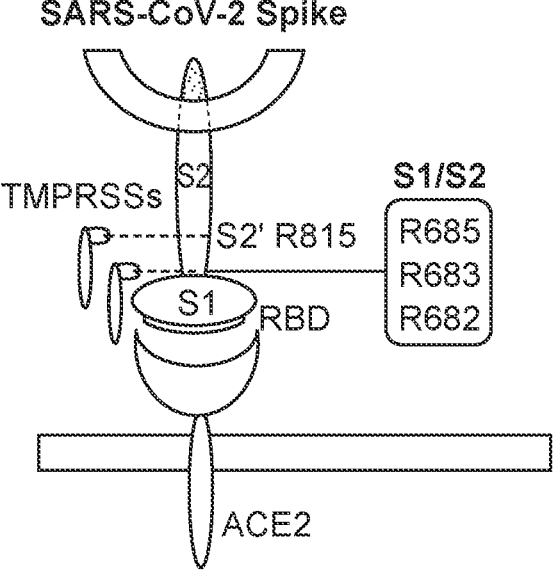
FIG. 2

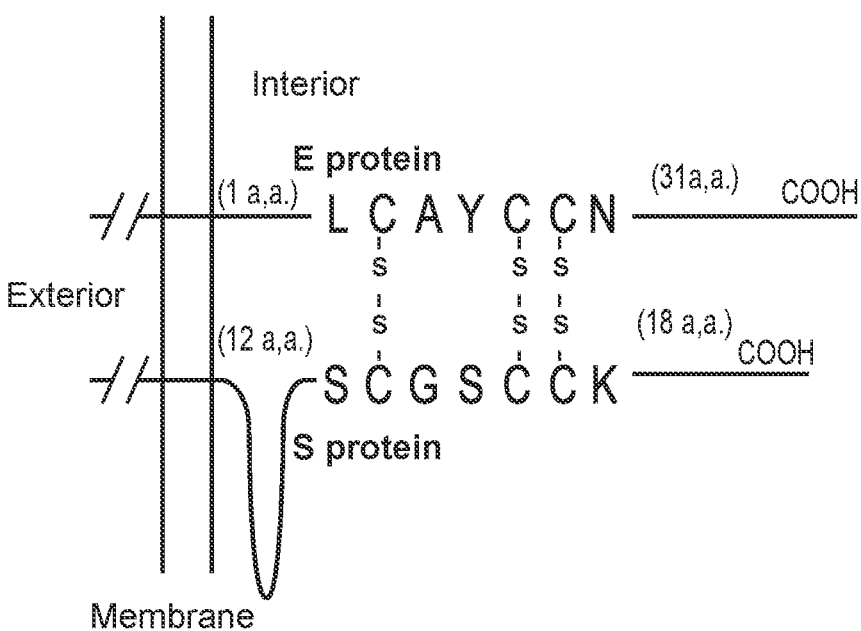

FIG. 3

| HPV type | L1-P1Arg74 | L2-P1Arg12 | L2-P1Arg305 |
|---|---|---|---|
| 6 | VSGYQYRVFK VVLPDP | MAHSRARRRKR ASATQL | SRRGLVRYSR IGQRGS |
| 11 | VSGYQYRVFK VVLPDP | MKPRARRRKR ASATQL | SRRGLVRFSR IGQRGS |
| 13 | VSGYQFRVFK VVLPDP | MAHSRARRRKR ASATQL | SRRGLVRFSR IGQRGS |
| 16 | VSGLQYRVFR IHLPDP | MRHKRSAKRTKR ASATQL | SRRTGIRYSR IGNKQT |
| 18 | VSAYQYRVFR VQLPDP | MVSHRAARRKR ASVTDL | SRRGTVRFSR LGQRAT |
| 31 | VSGLQYRVFR VRLPDP | MRSKRSTKRTKR ASATQL | SRRNTVRYSR LGNKQT |
| 33 | VSGLQYRVFR VRLPDP | MRHKRSTRRKR ASATQL | SRRHTVRFSR VGQKAT |
| 42 | VSGLQYRVFR VRLPDP | MPPQRSRRRKR ASATQL | SKQGSVRVSR IGQRLS |
| 44 | VSGFQYRVFK MVLPDP | MAHSRARRRKR ASATQL | SRRGRVRFSR IGQRGS |
| 52 | VSGLQYRVFR IKLPDP | MRYRRSTRHKR ASATQL | SRRGTVRFSR LGNKAT |
| 58 | VSGLQYRVFR VRLPDP | MRHKRSTRRKR ASATQL | SRRGTVRYSR VGQKAT |
| 59 | VSAYQYRVFR VNLPDP | MVSHRAARRKR ASATDL | SRRSTVRFSR LGQRAT |
| 66 | VSAYQYRVFR VRLPDP | MVAHRATRRKR ASATQL | TRRTGVRFSR LGKKAT |
| 68 | VSAYQYRVFR VSLPDP | MVSHRAARRKR ASATEL | SRRGTVRFSR VGKKAT |
| 72 | VSGYQYRVFR VKLPDP | MTQAVRRRKR ASATDL | ARQGTVRVSR LGQRAT |
| 94 | VSAYQYRVFR VRLPDP | MVAHRARRRKR ASATQL | SRRGAVRFSR LGQKFS |

FIG. 4

Heparan sulfate proteoglycans
assist virus delivery

HEPARIN AND N-ACETYLCYSTEINE FOR THE TREATMENT OF LUNG INJURY

CROSS-REFERENCE

The present application is a U.S. National Phase Application under 35 U.S.C. § 371 of International Application No. PCT/US2021/023256, entitled "HEPARIN AND N-ACETYLCYSTEINE FOR THE TREATMENT OF A RESPIRATORY VIRUS", filed on Mar. 19, 2021, which claims the benefit of U.S. Provisional Application No. 62/993,644, entitled "NEBULIZED THERAPEUTICS FOR COVID-19 DISEASE AND SARS-COV-2 TREATMENT AND PREVENTION", filed on Mar. 23, 2020, U.S. Provisional Application No. 63/001,344, entitled "EFFICACY AND SAFETY OF NEBULIZED HEPARIN-N-ACETYL-CYSTEINE IN COVID-19 PATIENTS BY EVALUATION OF PULMONARY FUNCTION IMPROVEMENT", filed on Mar. 29, 2020, U.S. Provisional Application No.: 63/006,050, entitled "SAFETY AND EFFICACY OF THE TWO-DRUG COMBINATION HEPARIN AND N-ACETYL-CYSTEINE (H-NAC) IN COVID-19 PATIENTS BY EVALUATION OF PULMONARY FUNCTION IMPROVEMENT", filed on Apr. 6, 2020, U.S. Provisional Application No. 63/011,287, entitled "SELECTIVE ESTROGEN RECEPTOR MODULATORS FOR THE TREATMENT OF VIRAL INFECTIONS", filed on Apr. 16, 2020, U.S. Provisional Application No. 63/026,674, entitled "HEPARIN AND N-ACETYLCYSTEINE FOR THE TREATMENT OF VIRAL INFECTIONS", filed on May 18, 2020, and U.S. Provisional Application No. 63/038,092, entitled "HEPARIN AND N-ACETYLCYSTEINE FOR THE TREATMENT OF VIRAL INFECTIONS", filed on Jun. 11, 2020, each of which applications are herein incorporated by reference in their entireties for all purposes.

BACKGROUND

Viral infections are responsible for hundreds of thousands of deaths each year. However, treatment options are limited for many viruses. Additionally, carriers of a virus may be asymptomatic, leading to high transmission rates from infected but asymptomatic individuals. There is a need for improved drugs to treat viral infections in both symptomatic and asymptomatic individuals. Furthermore, people such as healthcare workers who are in contact with infected individuals are at high-risk of infection. There is a need for drugs to prevent viral infections in at-risk individuals and other members of the population.

SUMMARY

In various aspects, the present disclosure provides a method of reducing an infectivity of a respiratory virus in a subject in need thereof, the method comprising administering a heparin to the subject, thereby reducing the infectivity of the respiratory virus in the subject.

In some aspects, the respiratory virus is a coronavirus. In some aspects, the coronavirus is SARS-COV-2.

In some aspects, the method further comprises administering N-acetylcysteine to the subject. In some aspects, the heparin has an average molecular weight of at least 3 kDa and not more than 10 kDa. In some aspects, the heparin has an average molecular weight of at least 4 kDa and not more than 5 kDa. In some aspects, the heparin is enoxaparin. In some aspects, the method comprises administering at least 10,000 IU and not more than 400,000 IU of the heparin per day. In some aspects, the method comprises administering at least 60,000 IU and not more than 70,000 IU of the heparin per day. In some aspects, the method comprises administering at least 0.5 mg/kg and not more than 2 mg/kg of the heparin per dose. In some aspects, the method comprises administering 1, 2, 3, or 4 doses of heparin per day. In some aspects, the method comprises administering at least 1 g and not more than 30 g of N-acetylcysteine per day. In some aspects, the method comprises administering at least 4 g and not more than 5 g of N-acetylcysteine per day. In some aspects, the method comprises administering at least 400 mg and not more than 700 mg of N-acetylcysteine per day. In some aspects, the method comprises administering 2, 3, 4, 5, 6, 7, or 8 doses of N-acetylcysteine per day.

In some aspects, the method comprises inhaling the heparin, N-acetylcysteine, or a combination thereof. In some aspects, the subject is breathing under the assistance of mechanical ventilation. In some aspects, the method comprises inhaling the heparin, N-acetylcysteine, or a combination thereof through a ventilator. In some aspects, the method further comprises nebulizing the heparin, the N-acetylcysteine, or both. In some aspects, the method comprises continuously administering the heparin, N-acetylcysteine, or a combination thereof over a period of at least 8 hours. In some aspects, the method comprises administering the heparin, N-acetylcysteine, or a combination thereof at least three times per day.

In some aspects, the method further comprises administering an antiviral agent to the subject. In some aspects, the antiviral agent is selected from the group consisting of remdesivir, tocilizumab, lopinavir, sarilumab, and interferon-beta, or a combination thereof.

In some aspects, the heparin interacts with a positively charged region of a viral surface protein of the respiratory virus, thereby reducing the infectivity of the respiratory virus in the subject. In some aspects, the heparin reduces an interaction between the viral surface protein and a host cell protein of the subject. In some aspects, the viral surface protein is a viral spike protein, and wherein the host cell protein is an angiotensin-converting enzyme 2, a type II transmembrane serine protease, or a furin protein. In some aspects, the heparin inhibits viroporin formation in a host cell of the subject.

In some aspects, the N-acetylcysteine reduces a cysteine residue in a viral protein of the respiratory virus. In some aspects, the viral protein is a spike protein, an envelope protein, or a combination thereof. In some aspects, the method further comprises administering a polybasic cleavage site peptide to the subject, comprising inhibiting furin cleavage of a viral protein of the respiratory virus, thereby reducing the infectivity of the respiratory virus in the subject. In some aspects, the polybasic cleavage site peptide inhibits furin cleavage of a viral protein of the respiratory virus, thereby reducing the infectivity of the respiratory virus in the subject.

In various aspects, the present disclosure provides a method of reducing an infectivity of a coronavirus in a subject in need thereof, the method comprising administering: at least 1 mg/kg and not more than 5 mg/kg of enoxaparin per day, and at least 3 g and not more than 5 g of N-acetylcysteine per day, via inhalation, thereby reducing the infectivity of the respiratory virus in the subject.

In some aspects, the administering occurs as multiple doses per day. In some aspects, the coronavirus is SARS-COV-2. In some aspects, the enoxaparin is administered twice per day. In some aspects, the N-acetylcysteine is administered four times per day.

In various aspects, the present disclosure provides a method of treating or preventing a coronavirus infection in a subject in need thereof, the method comprising administering to the subject: a polyanionic electrolyte, and an antioxidant, thereby treating or preventing the coronavirus infection.

In some aspects, the polyanionic electrolyte is a glycosaminoglycan. In some aspects, the glycosaminoglycan comprises at average of at least 1, at least 2, at least 3, at least 4, at least 5, at least 6, at least 7, at least 8, at least 9, or at least 10 sulfonated disaccharides. In some aspects, the glycosaminoglycan comprises an average of no more than 10, no more than 15, no more than 20, no more than 25, no more than 30, no more than 35, or no more than 40 disaccharides. In some aspects, the glycosaminoglycan is heparin or heparan sulfate. In some aspects, the glycosaminoglycan has an average molecular weight of from 3 kDa to 40 kDa. In some aspects, the glycosaminoglycan has an average molecular weight of from 3 kDa to 15 kDa. In some aspects, the glycosaminoglycan has an average molecular weight of from 3 kDa to 10 kDa. In some aspects, the glycosaminoglycan has an average molecular weight of from 3 kDa to 7 kDa. In some aspects, the glycosaminoglycan is low molecular weight heparin. In some aspects, the polyanionic electrolyte is poly-glutamate, poly-aspartate, alginate, carboxy-methyl-cellulose, polyacrylic acid, or keratin sulfate.

In some aspects, the antioxidant contains a sulfhydryl group capable of reducing disulfide bonds. In some aspects, the antioxidant is cysteine, poly-cysteine, Succimer, Cysteamine, Azathioprine, Mercaptopurine, S-Methylcysteine, Selenocysteine, S-Phosphocysteine, D-pantetheine 4'-phosphate or N-acetylcysteine. In some aspects, the method further comprises administering a soluble polybasic cleavage site peptide. In some aspects, the polybasic cleavage site peptide comprises an RXXR motif or an RXXK motif, where R is arginine, K is lysine, and X is any amino acid.

In some aspects, the administering is performed by inhalation. In some aspects, the inhalation is performed through a ventilator. In some aspects, the inhalation is facilitated by a nebulizer. In some aspects, the administering comprises administering from 10,000 IU to 400,000 IU of the polyanionic electrolyte per day. In some aspects, the administering comprises administering from 20,000 IU to 100,000 IU of the polyanionic electrolyte per day. In some aspects, the administering comprises administering from 20,000 IU to 70,000 IU of the polyanionic electrolyte per day. In some aspects, the administering comprises administering from 1 g to 30 g of the antioxidant per day. In some aspects, the administering comprises administering from 1 g to 20 g of the antioxidant per day. In some aspects, the administering comprises administering from 1 g to 10 g of the antioxidant per day. In some aspects, the administering comprises administering from 1 g to 5 g of the antioxidant per day. In some aspects, the administering is performed for 1, 2, 3, 4, 5, 6, 7, 8, 9, 10, 11, 12, 13, 14, 15, 18, 21, or 28 days. In some aspects, the administering is performed 1, 2, 3, 4, 5, 6, 7, 8, 9, or 10 times per day. In some aspects, the administering is performed continuously.

In some aspects, the coronavirus is SARS-COV-2. In some aspects, the coronavirus is SARS-COV or MERS-COV. In some aspects, the subject is prevented from contracting the coronavirus infection. In some aspects, the subject is at an elevated risk for contracting the coronavirus infection relative to normal. In some aspects, the subject has the coronavirus infection. In some aspects, the subject is suspected to have the coronavirus infection. In some aspects, the subject has tested positive for the coronavirus infection, and where the subject is asymptomatic for the coronavirus infection. In some aspects, the method is performed 1, 2, 3, 4, 5, 6, 7, 8, 9, 10, 11, 12, 13, or 14 days after the subject was exposed to the coronavirus.

In some aspects, the method further comprises administering an antiviral agent. In some aspects, the antiviral agent is selected from the group consisting of remdesivir, tocilizumab, topinavir, sarilumab, interferon-beta, tenofovir disoproxil fumarate, nevirapine, delavirdine, efavirenz, saquinavir, ritonavir, indinavir, nelfinavir, amprenavir, lopinavir, darunavir and atazanavir, peramivir, zanamivir, oseltamivir, amantadine, rimantadine, adefovir dipivoxil, famciclovir, penciclovir, imiquimod, docosanole, foscarnet, maribavir, BAY 38-4766, GW275175X, MVE-1, MVE-2, AM-3, AM-5, mannozym, bropirimine, 3,6-bis(2-p-peridinoethoxy) acridine trihydrochloride, phenyleneamine, 2-amino-5-halo-6-aryl-4 (3H)-pyrimidinones, 2-amino-5-bromo-6-methyl-4 (3H)-pyrimidinone, 7,8-didehydro-7-methyl-8-thioxoguanosine, 7-deazaguanosine, melatonin, 8-chloro-7-deazaguanosine, CL246,738, glycyrrhizin, pleconaril, bananin, iodobananin, vanillinbananin, ansabananin, cubananin, adeninobananin, cloroquine, valinomycin, idoxuridine, aciclovir, valaciclovir, ganciclovir, valganciclovir, adenosine arabinoside, AraA monophosphate, cytosine arabinoside, cytosine arabinoside monophosphate, azidothymidine, 1-beta-D-ribofuranosyl-1,2,4-triazole-3-carboxamide, 5-ethynyl-1-beta-D-ribofuranosylimidazole-4-carboxamide, EICAR-monophosphate, ribamidine, ribavirin 2',3',5'-acetate, ribavirin-5'-sulfamate, ribavirin 5'-triphosphate, ribavirin 5'-monophosphate, ZX-2401, mycophenolic acid, tiazofurin, tiazofurin-5'-monophosphate, tiazofurin 2',3',5'-acetate, 7-thia-8-oxoguanosine, selenazofurin, pyrazofurin, furanonaphthoquinone derivatives, merimepodib, viramidine, 6-azauridine, 9-(2-phosphonylmethoxyethyl) guanine, (S)-9-(3-hydroxy-2-phosphonylmethoxypropyl) adenine, 9-(2-phosphonylmethoxyethyl) adenine, 9-(2-phosphonylmethoxyethyl)-2,6-diaminopurine, didenosine, dideoxycytosine, stavudine, lamivudine, abacavir, iodo-deozyuridine, and bromovinyl deoxiuridine, (S)-1-(3-hydroxy-2-phosphonylmethoxypropyl) cytosine, cyclic(S)-1-(3-hydroxy-2-phosphonylmethoxypropyl) cytosine, hexadecyloxypropyl-cidofovir, 3-deazaguanine, 3-deazauridine, 9-(S)-(2,3-dihydroxypropyl) adenine, zidovudine, didanosine, zalcitabine, stavudine, lamivudine, abacavir, and emtricitabine.

In various aspects, the present disclosure provides a composition for use in the method of any one of claims, the composition comprising a polyanionic electrolyte, an antioxidant, or a combination thereof formulated for inhalation.

In some aspects, the composition further comprises vitamin E. In some aspects, the vitamin E is gamma-tocopherol.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2 schematically illustrates binding of a SARS-COV-2 virion to a transmembrane ACE2 receptor, mediating infection of a target cell. Binding of the virion to the ACE2 receptor may be inhibited by heparin (top). Internalization may be activated by type II transmembrane serine proteases (TMPRSSs) of the host cell interacting with an arginine cluster (R685, R683, and R682) in the S1 and S2 regions of a SARS-COV-2 spike protein (bottom).

FIG. 3 schematically illustrates cysteine bonds formed between interior regions of SARS-COV-2 envelope (E) proteins and spike(S) proteins.

FIG. 4 shows polybasic cleavage site peptide sequences from HPV that may use used individually or in combination to test for inhibition of virus infectivity.

DETAILED DESCRIPTION

Figure 1:
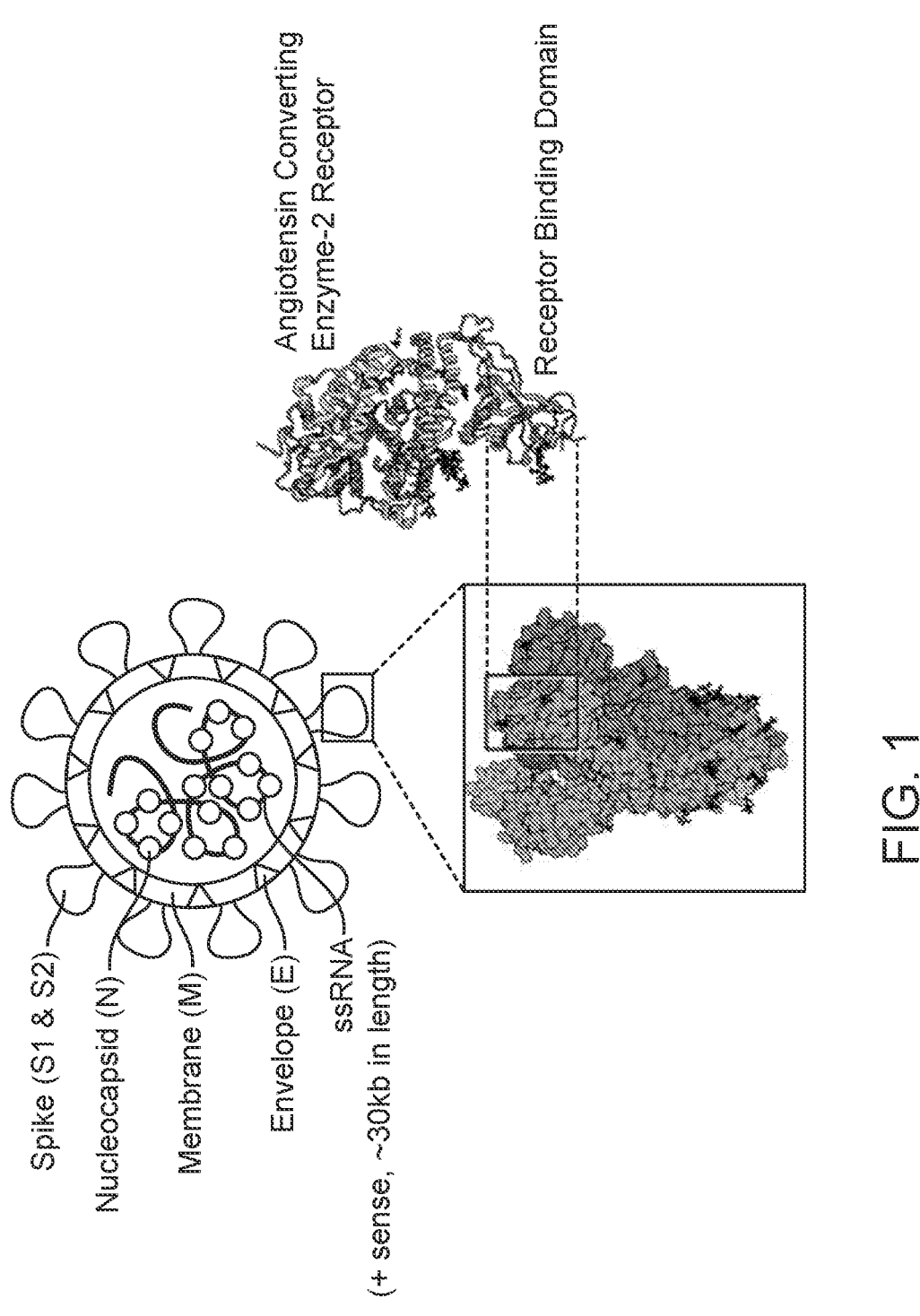
FIG. 1 schematically illustrates a SARS-COV-2 virion and a target cell angiotensin converting enzyme 2 (ACE2) receptor.

Disclosed herein are compositions and methods to treat or prevent a viral infection in a subject. The current COVID-19 pandemic has infected more than 100 million people and caused millions of deaths worldwide, as of this writing. Disclosed herein are compositions and methods for treatment, prevention, or reducing infectivity of viral infections, such as respiratory viral infections, including SARS-COV-2. Compositions for reducing infectivity of a viral infection may comprise a polyanionic electrolyte (e.g., a glycosaminoglycan such as heparin) and an antioxidant (e.g., an agent capable of reducing disulfide bonds such as N-acetylcysteine). For example, a composition for treatment of COVID-19 (caused by a SARS-CoV-2 infection) may comprise low molecular weight heparin (LMWH, e.g., enoxaparin), which may interact with surface proteins of SARS-COV-2 and inhibit viral infectivity, and N-acetyl-cysteine (NAC), which may disrupt interactions between viral envelope and spike proteins. In some embodiments, a composition of the present disclosure comprising heparin and N-acetylcysteine may be referred to herein as H-NAC. A composition of the present disclosure may act as a "chemical vaccine" based on a biophysical analysis of the eight separate envelope protein features of coronaviruses (e.g., SARS-COV-2) and corresponding host cell surface proteins and glycans which may be responsible for viral entry. In some embodiments, a composition of the present disclosure may reduce the infectivity of a viral infection (e.g., a respiratory viral infection such as a coronavirus infection). The compositions of the present disclosure may function to disrupt interactions between viral surface proteins and host cell receptor proteins, thereby preventing viral entry into the host cell, disrupt interactions between envelope capsid proteins, thereby inhibiting viral capsid formation, inhibit viroporin formation in host cell membranes, thereby slowing viral growth, prevent cleavage of viral spike proteins by host cell enzymes, thereby inhibiting viral membrane fusion, or a combination thereof. In some embodiments, a composition of the present disclosure may be used to treat a viral infection (e.g., a respiratory viral infection such as a coronavirus infection).

The methods and compositions disclosed herein may be used to reduce the infectivity of, treat, or prevent a viral infection. In some embodiments, the viral infection may be a respiratory virus infection. In some embodiments, the viral infection may be a coronavirus infection. The coronavirus may be SARS-COV, SARS-COV-2, MERS-COV, HKU1, OC43, or 229E. The coronavirus may be a beta-coronavirus. Pathogens with long incubation periods, such as SARS-COV-2 which has a median incubation period of about five days, may have high risk of transmission since many infected individuals may be unaware that they are infected.

SARS-COV-2 is the seventh coronavirus known to infect humans; SARS-COV, MERS-COV and SARS-COV-2 can cause severe disease, whereas HKU1, NL63, OC43 and 229E are associated with mild symptoms. The SARS-COV-2 human coronavirus is a 29,903-nucleotide, positive-strand RNA virus that is associated with a variety of highly prevalent and severe diseases, including SARS and Middle East respiratory syndrome (MERS).

Carriers of certain viruses (e.g., SARS-COV-2) may frequently be asymptomatic or have mild symptoms, leading to unknowing contact between a viral host and other members of a population. A subject at risk for a viral infection may come in contact with an asymptomatic carrier of the viral infection, thereby unknowingly contracting the viral infection. Methods and compositions are needed to prevent viral infections (e.g., coronavirus infections) in at-risk individuals (e.g., individuals who have come in contact with a carrier of a coronavirus or who may come in contact with a carrier of a coronavirus). In some embodiments, the methods and compositions disclosed herein may reduce the infectivity, treat, or prevent an infection caused by a virus. The virus may be one or more of arenaviridae (e.g., Pichinde virus, Lymphocytic Choriomeningitis Virus (LCMV), Lassa virus (causing Lassa fever) and Argentine hemorrhagic fever (AHF)), Paramyxoviridae (e.g., respiratory syncytial virus (RSV), measles virus (causing subacute sclerosing panencephalitis), mumps virus), herpesviridae (e.g., varicella-zoster (VZV), herpes simplex virus (HSV), human herpes virus-6 (HHV-6), cytomegalovirus (CMV), and Epstein Barr virus (EBV)), orthomyxoviridae (e.g., influenza A and B virus), picornaviridae (enteroviruses (3 polioviruses (PV), 28 echoviruses (ECV), 23 group A and 6 group B coxsackieviruses (CVA and CBV, respectively), or Theiler's virus), or 4 numbered enteroviruses), poxviridae (e.g., smallpox (variola), cowpox virus (CV), camelpox, monkeypox, or vaccinia viruses), reoviridae (e.g., bluetongue virus, rotavirus, simian (SA11) rotavirus or Colorado tick fever virus (CTFV)), polyomaviridae (e.g., JC Virus (JCV, causing PML in immune compromised patients), BK Virus (BKV), or simian virus 40 (SV40)), filoviridae (e.g., Marburg virus, or Ebola virus), rhabdoviridae (e.g., rabies), retroviridae (e.g., Human T-lymphotropic virus (HTLV, type I and II), or Human immunodeficiency virus (HIV, type I and II)), coronaviridae (e.g., coronavirus, or torovirus), adenoviridae, or iridoviridae.

A combined treatment of a polyanionic electrolyte (e.g., a heparin) and an antioxidant (e.g., N-acetylcysteine (NAC)) may act to reduce the infectivity of, prevent, treat, or prevent and treat a viral infection (e.g., a coronavirus infection) in a subject by targeting host cell entry, membrane fusion, viroporin formation, virion assembly, or a combination thereof. In some embodiments, a composition of the present disclosure may comprise an active agent (e.g., a drug) to prevent a viral infection, an agent to treat a viral infection, or both. In some embodiments, a composition provided herein may disrupt viral capsid formation. For example, N-acetylcysteine may disrupt SARS-COV-2 viral capsid assembly by disrupting cysteine bond formation between the E protein and the S protein of SARS-COV-2, as shown in FIG. 3. Heparin may disrupt interactions between viral proteins and host cell surface proteins, as shown in FIG. 2, or between the host cell membrane and a viroporin protein.

In some embodiments, a composition of the present disclosure (e.g., a composition comprising a heparin and N-acetylcysteine) may be administered to a subject noninvasively via inhalation (e.g., via a face mask, a nebulizer, or a ventilator). The composition may be formulated for delivery via inhalation. Delivery of a composition via inhalation may facilitate delivery of the composition into the lungs of a subject in need thereof and may, therefore, be a preferred delivery method for treatment of respiratory viruses (e.g., SARS-COV, MERS-CoV, and SARS-COV-2).

Mechanisms of Viral Inhibition

A viral infection may occur in multiple stages. First, a virus may infect a host cell by interacting with a host cell surface receptor and inserting viral genetic material into the host cell, either through internalization of the virion or by injection of the viral genetic material into the host cell. Following infection, the viral genetic material may hijack the host cell machinery to express viral proteins and assemble new virions. The newly assembled virions may then be released to infect other cells. Viruses may depend on protein-protein interactions between viral coat proteins (e.g., envelope proteins and spike proteins) for virion assembly. Additionally, viral growth rates may be enhanced by the incorporation of viroporins into membranes of host cells.

In some embodiments, a viral infection may be prevented by inhibiting the insertion of the viral genetic material into the host cell. FIG. 1 shows infection of a host cell with SARS-COV-2 mediated by interactions between the SARS-COV-2 spike(S) proteins and transmembrane ACE2 receptors of the host cell. Interactions between a viral surface protein (e.g., a coronavirus spike protein) and a host cell surface protein (e.g., an ACE2 receptor or a TMPRSS) may facilitate viral uptake. A viral infection may be prevented by disrupting interactions between a viral surface proteins and host cell proteins that activate or enhance insertion of the viral genetic material into the host cell. FIG. 2 shows interactions between a SARS-COV-2 spike protein, a host cell ACE2 receptor, and host cell type II transmembrane serine proteases (TMPRSSs). The TMPRSSs may interact with an arginine cluster within the SARS-COV-2 spike protein, thereby activating or enhancing viral invasion of the host cell. In some embodiments, a method of treating, preventing, or reducing the infectivity of a viral infection (e.g., a coronavirus infection) may comprise administering a polyanionic electrolyte (e.g., a negatively charged glycosaminoglycan such as heparin) to a subject.

Figure 6:
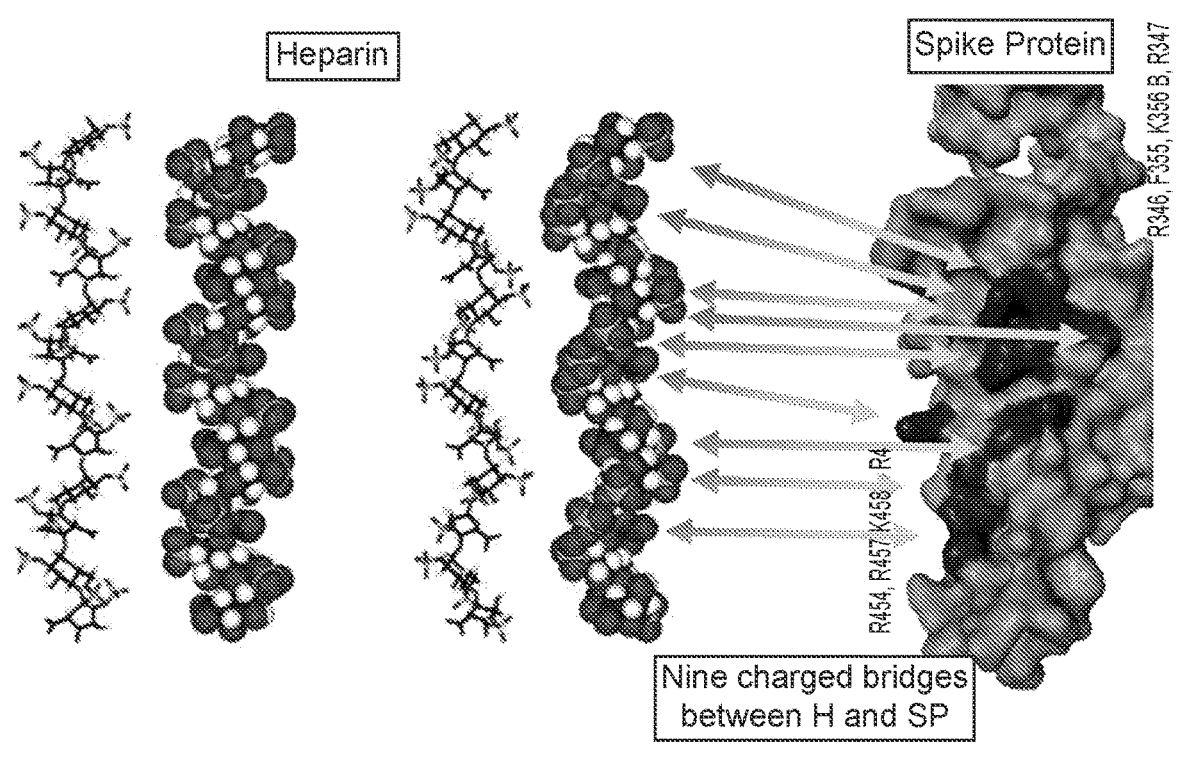
FIG. 6 illustrates the predicted binding of heparin to a SARS-COV-2 viral spike protein and formation of charged bridges.

Administering a composition comprising a polyanionic electrolyte may prevent a viral infection by preventing internalization of a virus into a cell of the subject or by preventing internalization of a viral genome into a cell of the subject. The polyanionic electrolyte may bind to positively charged regions of viral surface proteins (e.g., positively charged regions of a coronavirus spike protein) and block binding of the viral surface protein to host cell surface receptors (e.g., epithelial angiotensin converting enzyme (ACE) receptors). A composition provided herein (e.g., a composition comprising heparin and N-acetylcysteine) may disrupt or prevent an interaction between a viral surface protein (e.g., a spike protein or an envelope protein) and a host receptor protein (e.g., an epithelial angiotensin converting enzyme (ACE) or an epithelial furin enzyme). In some embodiments, the methods and compositions provided herein may prevent a viral infection by disrupting an interaction between a viral surface protein (e.g., a spike protein or an envelope protein) and an activating host cell protein (e.g., a type II transmembrane serine protease). For example, the polyanionic glycosaminoglycan heparin may block internalization of a coronavirus into a cell of a subject by blocking or disrupting interactions between a coronavirus spike protein and a host receptor protein, as illustrated in FIG. 1. Administering heparin to a subject at risk for a viral infection may reduce the risk of coronavirus infection in the subject. Heparin may disrupt interactions between an ACE2 receptor, thereby preventing a viral infection. Heparin may disrupt interactions by interacting with negatively charged amino acids on the surface of either the receptor or a viral spike protein. A putative binding site for heparin on a surface of a viral spike protein and the predicted electrostatic interactions are shown in FIG. 6. In some embodiments, the SARS-COV-2 surface protein (Spike) S1 Receptor Binding Domain may undergo a conformational change upon heparin binding.

Administration of a composition comprising an antioxidant may treat, prevent, or reduce the infectivity of a viral infection by inhibiting or disrupting interactions between proteins forming the viral capsid. Protein-protein interactions within a viral capsid may comprise disulfide bonds, as shown for interactions between coronavirus E proteins and S proteins in FIG. 3. FIG. 3 shows interactions between internal regions of a SARS-COV-2 E protein and a SARS-COV-2 S protein. In some embodiments, a viral infection may be treated by disrupting assembly of new virions or disrupting protein-protein interactions in assembled viral capsids. In some embodiments, the methods and compositions provided herein may treat a viral infection by disrupting assembly of a viral capsid. For example, a composition provided herein may disrupt cysteine bond formation between viral proteins (e.g., between a spike(S) protein and an envelope (E) protein). Viral capsids may be stabilized by cysteine bonds formed between the E proteins and the S proteins. An antioxidant (e.g., N-acetylcysteine) may disrupt disulfide interactions between the viral E proteins and S proteins, thereby disrupting viral assembly. An antioxidant may function by reducing the disulfide bonds, thereby inhibiting or disrupting interactions between viral capsid proteins. An example of an antioxidant that may be used in a composition or method of the present disclosure may be N-acetylcysteine (NAC).

Figure 5:
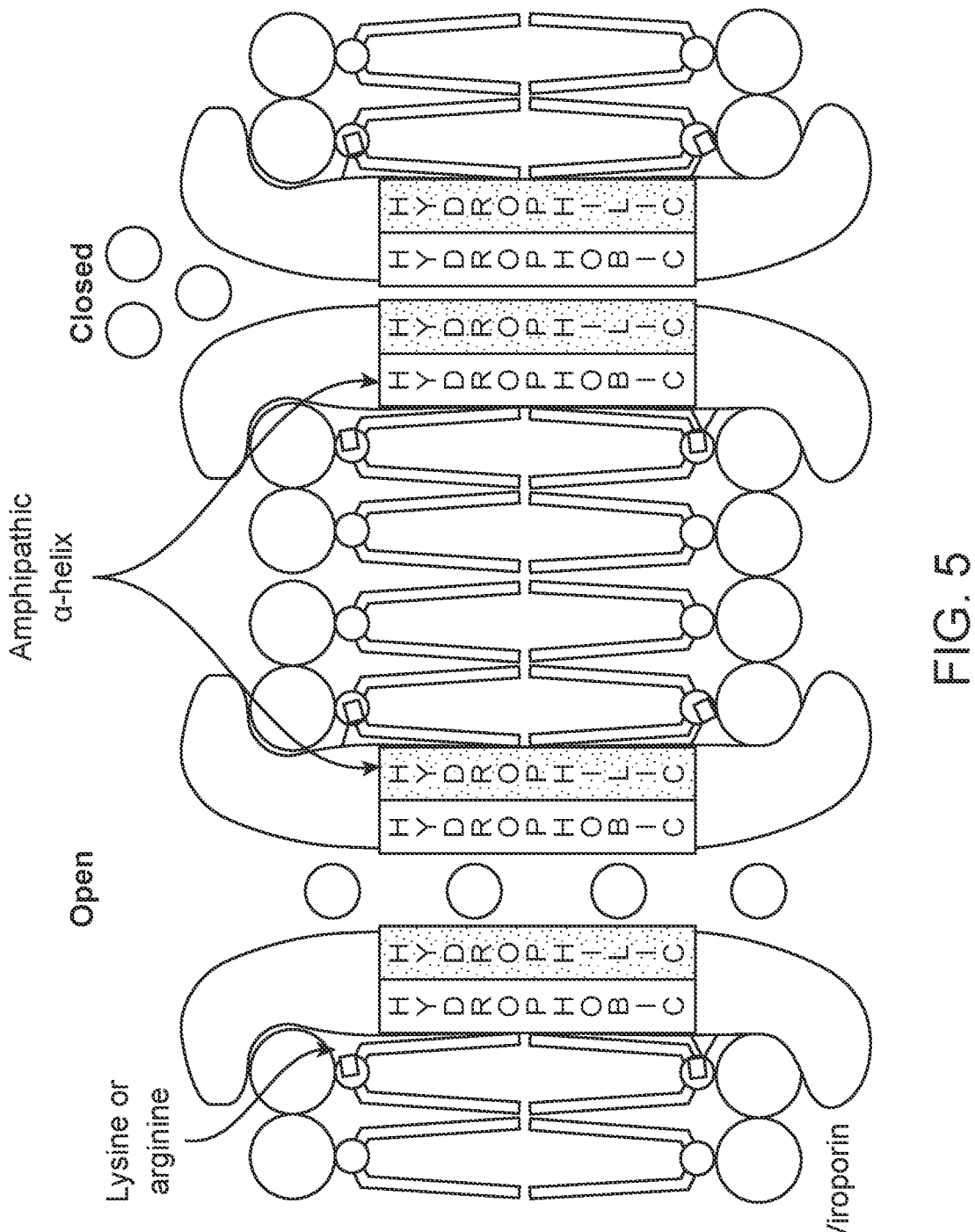
FIG. 5 shows a schematic of a viroporin structure showing cell surface basic amino acids, arginine and lysine, that anchor the protein at the membrane surface. Heparin is predicted to disrupt interactions between cell surface basic amino acids and the negatively charged cell membrane.

In some embodiments, the methods and compositions provided herein may treat, prevent, or reduce infectivity of a viral infection by disrupting viroporin formation in host cell membranes. Viroporins may increase growth rates of viruses in host cells, and disrupting viroporin formation may slow a viral infection. A viroporin may comprise positively charged amino acid residues (e.g., lysine or arginine) that ionically interact with the negatively charged phosphate groups of the host cell membrane. The ionic interactions formed between positively charged residues in a viroporin and a negatively charged cell membrane are illustrated in FIG. 5. A composition provided herein comprising a polyanionic electrolyte may disrupt viral ion channel formation (e.g., a viroporin ion channel) by disrupting ionic interactions between viroporins and host cell membranes. For example, a negatively charged glycosaminoglycan (e.g., heparin) may disrupt viral ion channel formation by disrupting interactions between basic amino acids in the ion channel and phospholipid heads in the viral capsid membrane.

In some embodiments, a composition of the present disclosure may comprise a polybasic cleavage site (PBCS) peptide. A PBCS peptide may comprise an RXXR motif or an RXXK motif. In some embodiments, a PBCS peptide may comprise an RAAR sequence. Examples of PBCS peptides are provided in FIG. 4. A PBCS peptide may function by inhibiting furin, thereby preventing cleavage of viral proteins comprising a PBCS by furin.

Viral and Host Cell Components Involved in Coronavirus Infectivity

The compositions and methods of the present disclosure may exploit one or more components of a virus or a host cell to treat, prevent, or reduce the infectivity of a viral infection. For example, a composition of the present disclosure comprising a polyanionic electrolyte (e.g., a heparin) and an antioxidant (e.g., N-acetylcysteine) may be administered to a subject having or at risk of having a viral infection. In some embodiments, the polyanionic electrolyte is a low molecular weight heparin (e.g., bemiparin, nadroparin, reviparin, enoxaparin, parnaparin, certoparin, dalteparin, or tinzaparin). The polyanionic electrolyte may inhibit ionic interactions between one or more of a viral spike protein and a host cell receptor, a viroporin and a host cell membrane, or a furin and a polybasic cleavage site. The antioxidant may prevent or disrupt protein-protein interactions between viral capsid proteins by breaking or inhibiting disulfide bond formation. In some embodiments, the composition may further comprise a PBCS peptide or lactoferrin. A PBCS peptide may inhibit furin cleavage of viral peptides comprising a PBCS, and lactoferrin may enhance neutrophil aggregation. In some embodiments, a composition of the present disclosure may be used to treat or prevent a coronavirus infection (e.g., a SARS-COV-2 infection).

There are at least four features that distinguish SARS-COV-2 from the other coronaviruses and which may be related to its virulence in humans: A series of six-point mutations in the Spike Protein (SP) receptor binding domain angiotensin converting enzyme 2 (ACE2) contact residues (residues 455 to 505) that have partial homology with mutations found in previous coronaviruses and which confer a 10- to 20-fold increased affinity for the cell entry receptor, ACE2; A polybasic cleavage site (PBCS), not previously found in human coronavirus SP, with canonical furin protease peptide sequence; A main coronavirus protease, called 3C-like protease, which has a slightly higher turnover rate than previous CoV-2 viral proteases but a >30-fold higher turnover rate than the human rhinovirus 3C protease. A transmembrane serine protease, TMPRSS2 that acts on the SP following ACE2 binding and is necessary to prime cell entry. An additional feature, shared by all other coronaviruses, is the presence of a viroporin which forms multimeric, cationic, transmembrane channels reminiscent of model membrane channels such as alamathicin. A composition of the present disclosure (e.g., a composition comprising a polyanionic electrolyte and an antioxidant) may target one or more of these features.

Human epithelial and endothelial cells have at least three features important for coronavirus infection: ACE2, the putative primary SARS-COV-2 viral binding receptor; Cell surface heparan sulfate proteoglycans, identified as pre-ACE2 docking sites which appear to accelerate ACE2 binding; Furin, a cell surface proprotein convertase as a putative receptor and/or covalent processor of SARS-COV-2, and its role in infectivity. Human coronavirus infectivity and the unique features of SARS-COV-2 among coronaviruses that can be targeted with the compositions and methods of the present disclosure are summarized in TABLE 1.

TABLE 1

Human Coronavirus Infectivity and Other Features

| Host/Virus | Feature Targeted | Structure | Function |
|---|---|---|---|
| Virus | Spike Protein (SP) binding motif | Polybasic cleavage site is part of the receptor binding domain of CoV-2 and has a basic amino acid motif containing nine R/K residues in close proximity | Allows effective cleavage by furin and other proteases and has a role in determining viral infectivity. |
| Virus | SP-viral E protein interactions | Envelope proteins SP and E protein are covalently bound together via three cystine —S—S— bonds; axial and peripheral E proteins contain basic, cationic motifs | Stabilizes the SP and facilitates SP binding to ACE2; provides a basis for virus binding to cell surface heparan sulfate proteoglycans |
| Virus | Main intracellular protease | A CoV-2 intracellular viral encoded cysteine-class protease | A cysteine-class viral protease essential for viral replication by virtue of processing 11 separate, highly conserved proteins from the overlapping polyproteins, pp1a and pp1ab, required for viral replication and transcription |
| Virus | Coronavirus viroporin | Small (60 to 120 amino acids), largely hydrophobic peptides that form cationic channels in the host membrane and that are anchored to the host membrane | While not essential for replication but their absence weakens or attenuates the virus and diminishes its pathogenic effects |

TABLE 1-continued

Human Coronavirus Infectivity and Other Features

| Host/ Virus | Feature Targeted | Structure | Function |
|---|---|---|---|
| | | laterally with phospholipid head group-arginine amino acid residues | |
| Host | Transmembrane protease, serine 2, TMPRSS2 | Responsible for cleavage of S1/S2 near R residues (R682, R683, R685, and R667, R797) | Following SP binding to ACE2, the cleavage of these S1/S2 motifs, primes CoV-2 for cell entry |
| Host | Epithelial ACE2 virus receptor | ACE protein contains seven extracellular cysteines, one unusual free cysteine and three disulfide cystine residues and these together contribute to ACE three-dimensional structure. | The primary SARS-CoV-2 receptor, found in high concentration in nasal mucosa, alveolar cells, and endothelial cells |
| Host | Epithelial heparan sulfate proteoglycan viral recognition site | Ubiquitous cell surface anionic polymers | Coronavirus cell surface recognition site |
| Host | Furin, epithelial surface viral processing enzyme, highly expressed in alveoli | Protease with a polybasic peptide substrate specificity | Activation of the SARS coronavirus spike protein via sequential proteolytic cleavage at two distinct sites by furin |

Figure 7:
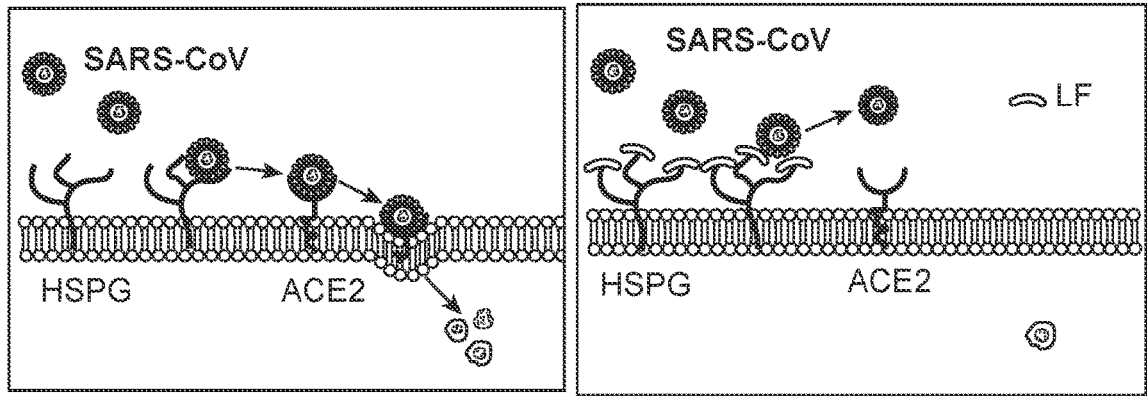
FIG. 7 illustrates internalization of a SARS-COV facilitated by ACE2 (left) and heparin proteoglycans (right). Soluble heparin may act as a decoy to prevent cell entry.

Studying SARS-COV-2 Spike protein structure and behavior in solution is a vital step for the development of effective therapeutics against SARS-COV-2. The SARS-COV-2 S1 receptor binding domain (RBD) may bind to a polyanionic electrolyte (e.g., heparin) via ionic interactions. Upon binding, a significant structural change may be induced. The receptor binding domain of SARS-COV-2 and interactions between heparin and the RBD are illustrated in FIG. 6. Moreover, moieties of basic amino acid residues, forming potential heparin binding domains, are solvent accessible on the SARS-COV-2 S1 RBD surface and form a continuous patch that is suitable for heparin binding (dark regions of SARS-COV-2 E protein shown in FIG. 6). Interactions between viral spike proteins and cell surface receptors that may be disrupted by polyanionic electrolytes are illustrated in FIG. 1, FIG. 2, and FIG. 7.

Glycosaminoglycans are ubiquitously present on almost all mammalian cells and this class of carbohydrates are central to the strategy employed by coronaviridae to attach to host cells. Negatively charged glycosaminoglycans bound to host cell surface proteins (e.g., heparan sulfate proteoglycans (HSPGs)) may facilitate viral recruitment to and incorporation into host cells, as shown in FIG. 7. Administration of a free glycosaminoglycan (e.g., heparin) may inhibit interactions between viral surface proteins and the host cell HSPGs, thereby inhibiting viral recruitment to the host cell. Since heparin may inhibit SARS-associated coronavirus strain HSR1 cell invasion by binding to viral spike proteins or cell surface receptors, glycosaminoglycan-derived pharmaceuticals (e.g., low molecular weight heparin) may be effective against SARS-associated coronaviruses (e.g., SARS-COV or SARS-COV-2).

The cell surface binding of SARS-COV-2, the first step in internalization and replication in pulmonary epithelial cells, may be governed by the biophysical interaction of five biological components: the viral Spike Protein binding motif, the viral E protein-Spike protein interactions, the epithelial heparin sulfate poly-anion surface decoration, the epithelial Angiotensin Converting Enzyme 2 (ACE), the putative primary viral binding receptor, the epithelial furin enzyme, a cell surface proprotein convertase as a receptor and/or covalent processor of SARS-COV-2, and its role in infectivity. A two-drug combination comprising a polyanionic electrolyte and an antioxidant may function to treat or prevent a viral infection at multiple stages.

Spike and Envelope Proteins

The coronavirus envelope (E) protein is a short, integral membrane protein of 76-109 amino acids, ranging from 8.4 to 12 kDa in size. The primary and secondary structure reveals that E has a short, hydrophilic amino terminus consisting of 7-12 amino acids, followed by a large hydrophobic transmembrane domain (TMD) of 25 amino acids, and ends with a long, hydrophilic carboxyl terminus, which comprises the majority of the protein. The coronavirus(S) protein is the spike protein. Both E and S contain a triple cysteine motif located directly after the E protein TMD (NH2- . . . L-Cys-A-Y-Cys-Cys-N . . . COOH) and a similar motif located in the C-terminus of S (NH2- . . . S-Cys-G-S-Cys-Cys-K . . . COOH), as shown in FIG. 3. The predicted orientation, position, and composition of these two motifs could serve as a structural basis for the association between E and S, which would be mediated by the formation of disulfide bonds between the corresponding cysteine residues. The 2019 coronavirus (SARS-COV-2) surface protein (Spike) S1 Receptor Binding Domain undergoes a substantial conformational change upon heparin binding. A composition of the present disclosure comprising an antioxidant may disrupt disulfide bonds between a viral envelope protein and a viral spike protein. For example, N-acetylcysteine may reduce the disulfide bonds formed between a SARS-COV-2 E protein and a SARS-COV-2 S protein, thereby disrupting viral capsid formation.

A composition comprising a polyanionic electrolyte (e.g., a heparin) may inhibit a coronavirus infection (e.g., a SARS-COV-2 infection) by interacting with a spike protein (e.g., a SARS-COV-2 S1 protein), thereby preventing interactions with host cell proteins. For example, heparin may bind to the SARS-COV-2 spike protein through the unique, solvent accessible nine amino acid motif of the polybasic cleavage site, and that SP undergoes a significant change in secondary protein structure.

ACE2

Angiotensin-converting enzyme 2 (ACE2) is a terminal carboxypeptidase and the receptor for the SARS and NL63 coronaviruses (CoV). Loss of ACE2 function is implicated in severe acute respiratory syndrome (SARS) pathogenesis, but little is known about ACE2 biogenesis and activity in the airways. ACE2 may be shed from human airway epithelia, a site of SARS-COV infection. Constitutive generation of soluble ACE2 may be inhibited by DPC 333, implicating a disintegrin and metalloprotease 17 (ADAM17). Phorbol ester, ionomycin, endotoxin, and IL-ip and TNFa may induce ACE2 release, further supporting that ADAM17 and ADAM10 regulate ACE2 cleavage. Soluble ACE2 may be enzymatically active and partially inhibit virus entry into target cells. The ACE2 cleavage site resides between amino acid 716 and the putative transmembrane domain starting at amino acid 741. A point mutation in the ACE2 ectodomain, L584A, has been shown to markedly attenuated shedding while trafficking to the cell membrane and may facilitate SARS-COV entry into target cells, suggesting that the ACE2 ectodomain regulates its release and that residue L584 may be part of a putative sheddase recognition motif. Cell-associated ACE2 may serve as a coronavirus receptor, and soluble ACE2 might play a role in modifying inflammatory processes at the airway mucosal surface.

Lactoferrin (LF) may participate in the host immune response against SARS-COV invasion by enhancing NK cell activity and stimulating neutrophil aggregation and adhesion. LF may inhibit SARS infection. LF may be able to block the binding of spike protein to host cells, inhibiting the viral attachment stage. LF may not disrupt the interaction of spike protein with angiotensin-converting enzyme 2 (ACE2), the functional receptor of SARS-COV.

LF may co-localize with the widely distributed cell-surface heparan sulfate proteoglycans (HSPGs). Treatment of the cells with heparinase or exogenous heparin may prevent binding of spike protein to host cells and inhibit SARS infection at the early attachment phase. LF may play a protective role in host defense against SARS-COV infection through binding to HSPGs and blocking the preliminary interaction between SARS-COV and host cells.

A composition of the present disclosure comprising a polyanionic electrolyte (e.g., heparin) may prevent or treat a viral infection by binding to a positively charged region of a viral surface protein (e.g., a spike protein) and preventing interactions between the viral surface protein and the host cell ACE2 receptor.

Viroporins

Viroporins are viral encoded membrane pore-forming proteins that can modulate cellular ion channels and have been suggested to regulate and function in multiple stages of the viral life cycle, from viral entry to assembly and release, and even pathogenesis. Although viroporins are not essential to viral replication, their absence may weaken or attenuate the virus and diminishes its pathogenic effects. They tend to be small proteins (~60-120 amino acids) of a predominantly hydrophobic nature that oligomerize in the membranes of infected cells, forming hydrophilic pores. The hydrophobic residues line the outside of the structure, oriented toward the phospholipids, while the inside of the pore is made up of the hydrophilic resides. Most viroporins share certain structural features such as an amphipathic a-helix in the hydrophobic domain (HD) along with a cluster of positively charged, basic amino acids (such as lysine or arginine) which anchor the pore to the membrane through electrostatic interactions with the negatively charged phospholipids. This may be disrupted by heparin. A viroporin and the electrostatic interactions between the viroporin and a host cell membrane are illustrated in FIG. 5.

A composition of the present disclosure comprising a polyanionic electrolyte (e.g., heparin) may prevent, treat, or reduce the infectivity of a viral infection (e.g., a coronavirus infection) by disrupting interactions between the viroporin and the host cell membrane, thereby preventing viroporin formation and slowing viral growth.

Furin

The presence of a polybasic cleavage site (PBSC) in the viral spike protein of SARS-CoV-2 may allow effective cleavage by furin and other proteases and may have a role in determining viral infectivity and host range. The PBCS is not present in related coronaviruses, such SARS COV, bat coronavirus RaRG13, bat SARS-COV-related virus, and pangolin coronavirus. The three arginine residues in close proximity present in the SARS-CoV spike protein sequence are unusual. Proteins with PBSCs are also present in other viral proteins. For example, PBCS proteins from human papilloma virus (HPV) are shown in FIG. 4.

The PBCS sequence is, for example, similar to the furin cleavage sites of a series of HPV viruses. The furin PBCS peptide from HPV shown in FIG. 4 can be used individually or in combinations to test inhibition of virus infectivity by various compositions of the present disclosure.

Furin is a protein that in humans is encoded by the FURIN gene. Some proteins are inactive when they are first synthesized, and must have sections removed in order to become active. Furin cleaves these sections and activates the proteins. For example, some group 1 coronavirus spike proteins carry a furin enzyme recognition motif and may be cleaved by furin to become active. Interestingly, this feature can be lost during cell culture adaptation by a single mutation in the cleavage motif. This mutation, however, preserves a heparan sulfate binding motif and renders infection by the virus heparin sulfate dependent.

Furin was named because it was in the upstream region of an oncogene known as FES. The gene was known as FUR (FES Upstream Region) and therefore the protein was named furin. Furin is also known as PACE (Paired basic amino acid Cleaving Enzyme).

The spike glycoprotein of SARS-COV-2 contains a furin-like cleavage site absent in coronavirus of the same clade. Since furin is highly expressed in lungs, an enveloped virus that infects the respiratory tract may successfully exploit this convertase to activate its surface glycoprotein. Prior to the emergence of SARS-COV-2, a furin cleavage site was not observed in the lineage of beta coronaviruses. However, it is shared by other coronaviruses (e.g., HCoV, OC43, MERS-COV, and MHV-A59) containing furin-like cleavage sites in their S-proteins which may be processed by furin. The SARS-COV-2 S protein sequence contains 12 additional nucleotides upstream of the single Arg cleavage site, leading to a predictably solvent-exposed PRRAR SV sequence, which corresponds to a canonical furin-like cleavage site. This furin-like cleavage site may be cleaved during virus egress for S-protein priming and may provide a gain of function to the SARS-COV-2 for efficient spreading in the human population as compared to other beta coronaviruses. If this site is not processed, the S-protein may be cleaved at a second site during virus endocytosis, as observed for SARS-COV.

The coronavirus spike protein(S) may play a key role in the early steps of viral infection, with the S1 domain responsible for receptor binding and the S2 domain mediating membrane fusion. In some cases, the S protein may be proteolytically cleaved at the S1-S2 boundary (e.g., by furin). In the case of SARS-COV, virus entry may require the endosomal protease cathepsin L. However, infection of SARS-COV may be strongly induced by trypsin treatment. A proteolytic cleavage site within the SARS-COV S2 domain (S2', R797) may play a role in viral infection. Mutation of R797 may inhibit trypsin-dependent fusion. Introduction of a furin cleavage site at both the S2' cleavage site within S2 793-KPTKR-797 (S2') may allow trypsin-independent cell-cell fusion, and presence of a second furin cleavage site at the junction of S1 and S2 may further increase this effect. A proteolytic cleavage event on the SARS-COV S protein at position 797 (S2'), acting in concert with the S1-S2 cleavage site, ma mediate membrane fusion and virus infectivity. Inhibition of proteolytic cleavage (e.g., by administration of a polyanionic electrolyte or a PBCS peptide) may reduce the infectivity of, treat or prevent a viral infection (e.g., a SARS-COV-2 infection).

The mechanistic basis for a two-drug combination comprising a polyanionic electrolyte and an antioxidant is two-fold: SARS-COV-2, unlike the other six human SARS viruses has acquired a Polybasic Cleavage Site (PBCS), a short peptide sequence at residues 681-685 of the Spike(S) protein with three basic arginine residues. In other human viral pathogens the PBCS is a substrate for the cell surface enzyme, furin, and in these viruses, PBCS processing by furin is required for successful viral cycling. The polyanion, heparin, has been shown to alter the Spike protein structure of SARS-COV-2 and would be expected to bind electrostatically to the PBSC, blocking furin cleavage and infectivity. In vitro experiments demonstrate heparin blocks infectivity of virus that contain PBSC sequences. In addition to the PBCS site, another polybasic amino acid grouping is nearby, making an almost continuous, cluster of nine basic amino acids.

H-NAC Components for Inhibition of Viral Infections

A biophysical analysis of surface features of the SARS-COV-2 virus capsid provides a mechanistically-based hypothesis that nebulized heparin and N-acetylcysteine (NAC), either sequentially or together, may be effective in treating COVID-19 in hospitalized patients. These two drugs are currently FDA approved individually for other indications and therefore are immediately available immediately. This could potentially reduce the need for transition to mechanical ventilation in some patients and to lead to earlier hospital release for other patients.

A treatment comprising nebulized heparin (e.g., a low molecular weight heparin such as enoxaparin, daltaparin, or tinzaparin) and N-acetylcysteine may be referred to as nebulized H-NAC. The safety profile of these FDA-approved pharmaceuticals suggests that they be immediately tested in clinical trials in COVID-19 patients.

Heparin, also known as unfractionated heparin (UFH), is a medication and naturally occurring glycosaminoglycan. As a medication it is used as an anticoagulant (blood thinner). It may also be used in the treatment of heart attacks and unstable angina. It can be given by injection into a vein or under the skin. Common side effects include bleeding, pain at the injection site, and low blood platelets. Heparin is a polyanion and its structure is shown here. The most common disaccharide unit is composed of a 2-O-sulfated iduronic acid and 6-O-sulfated, N-sulfated glucosamine, IdoA (2S)-GlcNS (6S). For example, this makes up 85% of heparins from beef lung and about 75% of those from porcine intestinal mucosa.

Based in part on an understanding of the behavior of polybasic model peptides such as the honeybee (*Apis mellifera*) venom, melittin, with respect to membrane binding and fusion properties, heparin, is a polysaccharide with the highest anionic charge density found in nature, was identified as potential SARS-COV-2 viral entry inhibitor. The identification of several key cystine bridge structures that are important for viral cell surface binding or entry permitted a proposal that N-acetyl-cysteine might disrupt infectivity by the known irreversible cleavage of the S1-S2 viral spike protein bonds with the formation of S1-S-NAC and NAC-S-S2 moieties. TABLE 2 lists potential mechanisms of action of heparin and N-acetylcysteine (H-NAC) in inhibiting SARS-COV-2 infectivity.

TABLE 2

| Mechanisms of Action for H-NAC in the Inhibition of SARS-CoV-2 Infectivity | | |
|---|---|---|
| Feature Targeted | Structure | Predicted Mechanism of Action of H-NAC |
| Spike Protein (SP) binding motif | Polybasic cleavage site is part of the receptor binding domain of CoV-2 and has a basic amino acid motif containing nine R/K residues in close proximity | Heparin: Electrostatic binding, preventing SP docking |
| SP-viral E protein interactions | Envelope proteins SP and E protein are covalently bound together via three cystine —S—S— bonds; axial and peripheral E proteins contain basic, cationic motifs | NAC: Cystine cleavage with SP-E destabilization; Heparin: electrostatic interference with cell surface heparan binding |
| Main intracellular protease | A CoV-2 intracellular viral encoded cysteine-class protease | NAC: Irreversible enzyme inhibitor |
| Transmembrane protease, serine 2, TMPRSS2 | Responsible for cleavage of S1/S2 near R residues (R682, R683, R685, and R667, R797) | Heparin: Electrostatic interference with S1/S2 priming, by creating a fusion motif |
| Coronavirus viroporin | Small (60 to 120 amino acids), largely hydrophobic peptides that form cationic channels in the host membrane and that are anchored to the host membrane laterally with phospholipid head group-arginine amino acid residues | Heparin: Electrostatic interference with arginine-phospholipid binding a viroporin collapse |
| Epithelial ACE2 virus receptor | ACE protein contains seven extracellular cysteines, one unusual free cysteine and three disulfide cystine residues and these together contribute to ACE three-dimensional structure. | NAC: Cystine cleavage with reduced SP binding affinity |
| Epithelial heparan sulfate proteoglycan viral recognition site | Ubiquitous cell surface anionic polymers | Heparin: A soluble decoy substrate for CoV-2 binding |
| Furin, epithelial surface viral | Protease with a polybasic peptide substrate specificity | Heparin: in vitro demonstration of inhibition of furin |

TABLE 2-continued

| Mechanisms of Action for H-NAC in the Inhibition of SARS-CoV-2 Infectivity | | |
| --- | --- | --- |
| Feature Targeted | Structure | Predicted Mechanism of Action of H-NAC |
| processing enzyme, highly expressed in alveoli | | |

Respiratory resistance after antigen exposure may be improved following pre-inhalation of low-molecular-weight heparin, poly-L-glutamic acid, poly-L-lysine, or dextran, with or without oral intake of dalteparin. Both immediate and late responses after antigen exposure were may decrease after pretreatment with inhaled low-molecular-weight heparin or poly-L glutamic acid. Oral dalteparin may further decrease late responses. Low-molecular-weight heparin and poly-L-glutamic acid may decrease the airway response to methacholine. The airway response to methacholine may be increased after pretreatment with inhaled poly-L-lysine. Pretreatment with inhaled low-molecular-weight heparin before poly-L-lysine exposure may suppress the airway hyper-responsiveness after inhaled poly-L-lysine. The "cationic-anionic interaction" may play an important role in airway responsiveness and contribute to the efficacy of heparin in improving respiratory function. Binding of HCoV-NL63 to heparan sulfate may facilitate viral attachment and infection of target cells, serving as attachment receptors for HCoV-NL63. ACE2 may be involved in viral entry. Heparan sulfate proteoglycans may function as adhesion molecules, increasing virus density on the cell surface and possibly facilitating the interaction between HCoV-NL63 and its receptor. Administration of a polyanionic electrolyte (e.g., heparin or heparan sulfate) may disrupt electrostatic interactions between viral surface proteins and ACE2 surface proteoglycans (e.g., heparan sulfate) and prevent recruitment of viral capsids to the host cell membrane, thereby reducing infectivity of the virus. This cationic amino acid cluster of the coronavirus spike protein is the putative heparin anionic binding site. Polyanionic electrolytes (e.g., heparin) may inhibit infection of host cells by viruses lacking a PBCS (e.g., SARS-COV) by inhibiting spike protein interactions with host cell proteins.

The cell surface binding of SARS-COV-2, the first step in internalization and replication in pulmonary epithelial cells is governed by the interaction of six biological components: The viral Spike Protein binding motif, the viral E protein-Spike protein interactions, the epithelial heparin sulfate poly-anion surface decoration, the epithelial Angiotensin Converting Enzyme 2 (ACE), the putative primary viral binding receptor, the epithelial furin enzyme, a cell surface proprotein convertase as a receptor and/or covalent processor of SARS-COV-2, and its role in infectivity. M Protein-lipid, Viroporin, can be disrupted by heparin.

Proteoglycan-binding peptides were designed based on consensus sequences in heparin binding proteins: XBBXBX and XBBBXXBX, where X and B are hydropathic and basic residues, respectively. Initial peptide constructs included $(AKKARA)_n$ and $(ARKKAAKA)_n$ (n=1-6). Affinity co-electrophoresis revealed that low $M_r$ peptides (600-1300) had no affinities for low molecular weight ($M_r$) heparin, but higher $M_r$ peptides (2000-3500) exhibited significant affinities ($K_d$~50-150 nM), which increased with peptide $M_r$.

A composition of the present disclosure may comprise a glycosaminoglycan (e.g., heparin). The glycosaminoglycan may comprise at average of at least 1, at least 2, at least 3, at least 4, at least 5, at least 6, at least 7, at least 8, at least 9, at least 10, at least 20, at least 30, at least 40, or at least 50 sulfonated disaccharides. In some embodiments, the glycosaminoglycan may comprise an average of no more than 10, no more than 15, no more than 20, no more than 25, no more than 30, no more than 35, no more than 40 disaccharides, no more than 50, no more than 60, or no more than 70 disaccharides. In some embodiments, the glycosaminoglycan may comprise an average molecular weight of from 3 kDa to 40 kDa, from 3 kDa to 15 kDa, 3 kDa to 10 kDa, or 3 kDa to 7 kDa, or from 4 kDa to 5 kDa. In some embodiments, the glycosaminoglycan may comprise an average molecular weight of about 4.5 kDa. In some embodiments, the glycosaminoglycan may be low molecular weight heparin. In some embodiments, the low molecular weight heparin is bemiparin, nadroparin, reviparin, enoxaparin, parnaparin, certoparin, dalteparin, or tinzaparin.

Antioxidants may inhibit angiotensin II (Ang II) actions by consuming stimulated reactive oxygen species. Antioxidants that are also strong reducers of disulfide bonds (e.g., N-acetylcysteine) may inhibit the binding of Ang II to its surface receptors with consequent attenuation of signal transduction and cell action. In contract, N-acetylserine, a nonreducing analogue of NAC, may not inhibit Ang II binding. Other antioxidants may regulate Ang II receptors differently: for example, alpha-Lipoic acid may lower Ang II binding after 24 h, and vitamin E may not lower Ang II binding at all. Certain antioxidants that are reducing agents may lower Ang II receptor binding, and Ang II-stimulated signal transduction may be decreased in proportion to decreased receptor binding.

In some embodiments, an antioxidant may disrupt disulfide bonds in human testicular angiotensin-converting enzyme (tACE).

Nitrate tolerance has been explained by 1) a direct loss of pharmacological effect due to reduced bioconversion and 2) an indirect effect due to activation of the renin/angiotensin system and counter-regulatory vasoconstriction. The sulfhydryl compound N-acetylcysteine (NAC) has been shown to attenuate and partly counteract tolerance to nitrates, and this effect has been attributed to a nitrate/sulfhydryl interaction and increased production of vasoactive intermediates. Sulfhydryl supplementation (e.g., with NAC) may modify the function of the renin/angiotensin system in vivo and may be mediated by inhibition of angiotensin converting enzyme activity.

Compositions

A composition of the present disclosure may comprise one or more active agents. In some embodiments, an active agent may be an agent to prevent or treat a viral infection. A composition of the present disclosure may comprise an active agent to prevent a viral infection, an active agent to treat a viral infection, or a combination thereof. In some embodiments, an active agent may be a polyanionic electrolyte (e.g., poly-glutamate, poly-aspartate, alginate, carboxy-methyl-cellulose, polyacrylic acid, keratin sulfate, heparan sulfate, or heparin), an antioxidant (e.g., cysteine, poly-cysteine, Succimer, Cysteamine, Azathioprine, Mercaptopurine, S-Methylcysteine, Selenocysteine, S-Phosphocysteine, D-pantetheine 4'-phosphate or N-acetylcysteine), a polyphosphate, a soluble polybasic cleavage site (PBCS) peptide, or a combination thereof. In some embodiments, the antioxidant may be a sulfhydryl-containing molecule. In some embodiments, the PBCS peptide may comprise an RXXR or an RXXK motif, where R is arginine, K is lysine, and X is any amino acid. In some embodiments, a composition may comprise heparin and N-acetylcysteine. Additional components may include vitamin E nebulization by a lipid aerosolization device to block the inward gated potassium channel involved in viral infectivity. For example, additional components may include nebulized gamma-tocopherol.

A viral infection may be mediated by an interaction between viral coat proteins and host cell surface receptors. Interaction between the viral coat proteins and the host cell surface receptors may lead to internalization of the virus into the host cell, leading to an infection. In some embodiments, interaction between the viral coat proteins and the host cell surface receptors may lead to internalization of a viral genome into the host cell. In some embodiments, an active agent to prevent a viral infection may bind to the host cell surface receptor, thereby preventing the interaction between the viral coat protein and the cell surface receptor and inhibiting internalization of the virus or the viral genome.

An active agent of the present disclosure may disrupt an interaction between a host cell protein and a viral protein. In some embodiments, an active agent of the present disclosure may disrupt an interaction between a viral protein and a host cell protein such as ACE2, TMPRSS, Furin, CHUK, CREBP, CSNK2A1, ADRB2, EIF4E, TUBB, ESR1, ESR2, MTOR, GRB2, NR3C1, HIFIA, HNF4A, APEX1, APP, AR, MITF, PPARG, TOP2A, TP53, VCAM1, or CALM1. The active agent may affect a virus-associated protein such as G3BP1, SYNCRIP, PARP1, DDX5, EEF1A1, PABC1, GSK3B, ANXA2, HNRNPA1, HNRNPA2B1, HSPA9, HSPD1, IKBKB, JUN, KPNB1, KPNA2, SMAD3, NCL, NONO, NPM1, PHB, PPPICA, PSMDI, BCL2L1, RPS20, SKP2, STAT3, STA5A, UBE2I, XPO1, BAG6, CAVI, EIF3F, EIF3I, or HGS. In some embodiments, an active agent may bind to a viroporin. In some embodiments, an active agent to prevent a viral infection may bind to the viral coat protein, thereby preventing the interaction between the viral coat protein and the cell surface receptor and inhibiting internalization of the virus. In some embodiments, an active agent to prevent a viral infection may bind to or interact with a viral spike protein, a viral E-protein, a host transmembrane protease (e.g., serine 2 or TMP RSS2), an ACE2 receptor, an epithelial heparin sulfate proteoglycan viral recognition site, or a furin. For example, furin inhibitors may be included in a composition of the present disclosure. In some embodiments, an active agent that may prevent a viral infection (e.g., a coronavirus infection) may be a polyanionic electrolyte (e.g., heparin), an antioxidant (e.g., N-acetylcysteine), or a soluble PBCS peptide. For example, heparin may bind to a pike protein binding motif, disrupt electrostatic interactions between a viral viroporin and a phospholipid, disrupt electrostatic interactions between S1 and S2 of a viral spike protein, bind to and inhibit furin, or inhibit viral interactions with a host cell by binding to the viral surface. In another example, N-acetylcysteine may disrupt an interaction between a viral spike protein and a viral E-protein, inhibit an intracellular viral protease, or disrupt cysteine bonds to reduce spike protein binding.

Once a virus or a viral genome has internalized into a host cell, the virions may amplify by synthesizing viral proteins and assembling into new virions. Virion assembly may require cysteine bond formation or interactions between two or more proteins. In some embodiments, an active agent may disrupt interactions between one or more of a viral spike protein, a viral envelope protein, a viral envelope, a viral nucleocapsid protein, or a viral nucleic acid (e.g., single stranded RNA, single stranded DNA, double stranded RNA, or double stranded DNA). In some embodiments, an active agent to treat a viral infection may disrupt cysteine bond formation in viral proteins, thereby disrupting virion formation. In some embodiments, an agent to treat a viral infection may disrupt interactions between two or more viral proteins, thereby disrupting virion formation. Release of new virions from a host cell may be facilitated by viroporins formed in the plasma membrane of the host cell. In some embodiments, an active agent to treat a viral infection may disrupt viroporin formation, thereby preventing release of newly formed virions. For example, heparin may disrupt viroporin formation. In some embodiments, an active agent to treat a viral infection may bind to or interact with an intracellular protease, a viral spike protein, a viral E-protein, a host transmembrane protease (e.g., serine 2 or TMP RSS2), an ACE2 receptor, an epithelial heparin sulfate proteoglycan viral recognition site, or a furin. An active agent that may treat a viral infection (e.g., a SARS-COV-2 infection) may be heparin, N-acetylcysteine, or a combination thereof.

A composition to reduce the infectivity of, treat, or prevent a viral infection may comprise heparin. A composition to reduce the infectivity of, treat, or prevent a viral infection may comprise heparin and N-acetylcysteine. For example, heparin may bind to a pike protein binding motif, disrupt electrostatic interactions between a viral viroporin and a phospholipid, disrupt electrostatic interactions between S1 and S2 of a viral spike protein, bind to and inhibit furin, or inhibit viral interactions with a host cell by binding to the viral surface. In another example, N-acetylcysteine may disrupt an interaction between a viral spike protein and a viral E-protein, inhibit an intracellular viral protease, or disrupt cysteine bonds to reduce spike protein binding.

In some embodiments, a composition to reduce the infectivity of, treat, or prevent a viral infection may comprise an additional antiviral agent. For example, a composition may comprise chloroquine, hydroxychloroquine, Remdesivir, Tocilizumab, Lopinavir, Sarilumab, interferon-beta, or a combination thereof. The additional antiviral agent may kill a virus or suppress viral replication. In some embodiments, a composition of the present disclosure may comprise tenofovir disoproxil fumarate, nevirapine, delavirdine, efavirenz, saquinavir, ritonavir, indinavir, nelfinavir, amprenavir, lopinavir, darunavir and atazanavir, peramivir, zanamivir (Tamiflu), oseltamivir (Relenza), amantadine, rimantadine, adefovir dipivoxil, famciclovir, penciclovir, imiquimod, docosanole, foscarnet (PFA), maribavir, BAY 38-4766, GW275175X, MVE-1, MVE-2, AM-3, AM-5, mannozym, bropirimine, 3,6-bis(2-p-peridinoethoxy) acridine trihydrochloride, phenylencamine, 2-amino-5-halo-6-aryl-4 (3H)-pyrimidinones, 2-amino-5-bromo-6-methyl-4 (3H)-pyrimidinone, 7,8-didehydro-7-methyl-8-thioxoguanosine, 7-deazaguanosine, melatonin, 8-chloro-7-deazaguanosine, CL246,738, glycyrrhizin, pleconaril, bananin, iodobananin, vanillinbananin, ansabananin, cubananin, adeninobananin, cloroquine, valinomycin, idoxuridine, aciclovir (acyclovir or acycloguansoine), valaciclovir (valacyclovir), ganciclovir, valganciclovir, adenosine arabinoside (AraA, Vidarabine), AraA monophosphate, cytosine arabinoside (AraC, cytarabine), cytosine arabinoside monophosphate (Ara-CMP), azidothymidine (AZT), 1-beta-D-ribofuranosyl-1,2, 4-triazole-3-carboxamide (ribavirin or RBV), 5-ethynyl-1-beta-D-ribofuranosylimidazole-4-carboxamide (EICAR), EICAR-monophosphate, ribamidine, ribavirin 2',3',5'-acetate, ribavirin-5'-sulfamate, ribavirin 5'-triphosphate, ribavirin 5'-monophosphate, ZX-2401, mycophenolic acid, tiazofurin, tiazofurin-5'-monophosphate, tiazofurin 2',3',5'-acetate, 7-thia-8-oxoguanosine, selenazofurin, pyrazofurin, furanonaphthoquinone derivatives, merimepodib (VX497), viramidine, 6-azauridine, 9-(2-phosphonylmethoxyethyl) guanine (PMEG), (S)-9-(3-hydroxy-2-phosphonylmethoxy-propyl) adenine (HPMPA), 9-(2-phosphonylmethoxyethyl) adenine (PMEA), 9-(2-phosphonylmethoxyethyl)-2,6-di-aminopurine (PMEDAP), didenosine (DDI), dideoxycyto-sine (DDC), stavudine (d4T), lamivudine (3TC, e.g., Epivir), abacavir (ABC), iodo-deozyuridine (DU), and bromovinyl deoxiuridine (BVDU or brivudin), (S)-1-(3-hydroxy-2-phosphonylmethoxypropyl) cytosine (HPMPC, cidofovir, CDV or Vistide®), cyclic HPMPC, hexadecy-loxypropyl-cidofovir (HDP-CDV, or CMX001), 3-deaz-aguanine (3-DG), 3-deazauridine, 9-(S)-(2,3-dihydroxypro-pyl) adenine ((S)-DHPA), zidovudine, didanosine, zalcitabine, stavudine, lamivudine, abacavir, emtricitabine, or a combination thereof.

Methods

A method of the present disclosure may comprise administering one or more compositions of the present disclosure (e.g., a composition comprising one or more active agents to reduce the infectivity of, treat, or prevent a viral infection) to a subject in need thereof. In some embodiments, a method of the present disclosure may comprise administering one or more active agents (e.g., an agent to prevent or treat a viral infection) to a subject in need thereof. The subject may be a human subject. The subject may have a viral infection (e.g., a coronavirus infection). The subject may have a suspected viral infection (e.g., a suspected coronavirus infection). The subject may be at risk of contracting a viral infection. For example, the subject may have had contact or be in contact with one or more individuals who have, are suspected to have, or are at risk of having a viral infection, or the subject may have been susceptible to or at risk of complications due to a viral infection (e.g., have an underlying health condition). In some embodiments, a method to reduce the infectivity of, treat, or prevent a viral infection may comprise administering one or more active agents. An active agent may be a polyanionic electrolyte (e.g., heparin), an antioxidant (e.g., N-acetylcysteine), a PBCS peptide (e.g., a peptide comprising an RXXR motif or an RXXK motif), hydroxychloroquine, a SERM, or an antiviral agent. In some embodiments, the one or more active agents may be administered in a single composition. In some embodiments, one or more active agents may be administered separately.

Dosing Regiments

In some embodiments, a method of the present disclosure may comprise administering a dose of a heparin, and optionally a dose of N-acetylcysteine, by inhalation via nebulization at regular intervals over a treatment duration. For example, heparin (e.g., a low molecular weight heparin such as enoxaparin) may be administered to a patient with a respiratory virus about every 12 hours for about 7 days, or until symptoms of the respiratory virus improve. In another example, heparin (e.g., a low molecular weight heparin such as enoxaparin) may be administered to a patient with a respiratory virus about every 12 hours followed along with N-acetylcysteine administered about every 6 hours for about 7 days, or until symptoms of the respiratory virus improve. In some embodiments, alternating doses N-acetylcysteine may be administered about 30 minutes after administering the heparin. In some embodiments, alternating doses of N-acetylcysteine may be administered concurrently with heparin. In some embodiments, a heparin may be administered to a patient with a respiratory viral infection about 2 times per day and N-acetylcysteine may be administered about 4 times per day for about 7 days, or until symptoms of the respiratory virus improve. In some embodiments, the N-acetylcysteine may be administered at from about 500 mg per dose to about 700 mg per dose. In some embodiments, the heparin may be administered at from about 0.5 mg/kg per dose to about 2 mg/kg per dose. In some embodiments, the heparin may be administered at from about 30 mg to about 200 mg per dose for an adult or from about 10 mg to about 100 mg per dose for a child. In some embodiments, the heparin may be administered at from about 50 IU/kg per dose to about 200 IU/kg per dose. International standard units (IU) of heparin may the anti-Factor Xa activity of heparin. Anti-factor Xa activity of heparin may be based on reference to the W.H.O. First International Low Molecular Weight Heparin Reference Standard.

In some embodiments, heparin (e.g., a low molecular weight heparin) may be administered to a patient with a respiratory viral infection about every 6, about every 7, about every 8, about every 9, about every 10, about every 11, about every 12, about every 13, about every 14, about every 15, about every 16, about every 17, or about every 18 hours for a desired treatment duration. In some embodiments, heparin may be administered to a patient with a respiratory viral infection about every 3 to 5 hours, every 4 to 6 hours, every 5 to 7 hours, every 6 to 8 hours, every 7 to 9 hours, every 8 to 10 hours, every 9 to 11 hours, every 10 to 12 hours, every 11 to 13 hours, every 12 to 14 hours, every 13 to 15 hours, every 14 to 16 hours, every 15 to 17 hours, every 16 to 18 hours, every 17 to 19 hours, every 19 to 21 hours, every 20 to 22 hours, every 21 to 23 hours, or every 22 to 24 hours for a desired treatment duration. In some embodiments, N-acetylcysteine may be administered to a patient with a respiratory viral infection about every 1, about every 2, about every 3, about every 4, about every 5, about every 6, about every 7, about every 8, about every 9, about every 10, about every 11, about every 12, about every 13, about every 14, about every 15, about every 16, about every 17, or about every 18 hours. In some embodiments, heparin may be administered about 1, 2, 3, 4, 5, 6, 7, or 8 times per day. In some embodiments, N-acetylcysteine may be administered about 2, 3, 4, 5, 6, 7, 8, 9, or 10 times per day.

In some embodiments, a treatment comprising heparin, and optionally N-acetylcysteine, may be administered for a treatment duration of about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days. In some embodiments, a treatment comprising heparin, and optionally N-acetylcysteine, may be administered for a treatment duration of up to about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days. In some embodiments, a treatment comprising heparin, and optionally N-acetylcysteine, may be administered until symptoms of the respiratory viral infection improve.

In some embodiments, heparin may be administered at about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.2 mg/kg, about 1.4 mg/kg, about 1.6 mg/kg, about 1.8 mg/kg, about 2 mg/kg, about 2.2 mg/kg, about 2.4 mg/kg, about 2.6 mg/kg, about 2.8 mg/kg, about 3 mg/kg, about 3.5 mg/kg, about 4 mg/kg, about 4.5 mg/kg, about 5 mg/kg, about 5.5 mg/kg, or about 6 mg/kg per dose. In some embodiments, heparin may be administered at from about 0.1 mg/kg to about 1 mg/kg, from about 0.1 mg/kg to about 2 mg/kg, from about 0.1 mg/kg to about 3 mg/kg, from about 0.1 mg/kg to about 4 mg/kg, from about 0.1 mg/kg to about 5 mg/kg, from about 0.1 mg/kg to about 6 mg/kg, from about 0.5 mg/kg to about 1 mg/kg, from about 0.5 mg/kg to about 2 mg/kg, from about 0.5 mg/kg to about 3 mg/kg, from about 0.5 mg/kg to about 4 mg/kg, from about 0.5 mg/kg to about 5 mg/kg, from about 0.5 mg/kg to about 6 mg/kg, from about 1 mg/kg to about 2 mg/kg, from about 1 mg/kg to about 3 mg/kg, from about 1 mg/kg to about 4 mg/kg, from about 1 mg/kg to about 5 mg/kg, from about 1 mg/kg to about 6 mg/kg, from about 2 mg/kg to about 3 mg/kg, from about 2 mg/kg to about 4 mg/kg, from about 2 mg/kg to about 5 mg/kg, from about 2 mg/kg to about 6 mg/kg, from about 3 mg/kg to about 4 mg/kg, from about 3 mg/kg to about 5 mg/kg, from about 3 mg/kg to about 6 mg/kg, from about 4 mg/kg to about 5 mg/kg, from about 4 mg/kg to about 6 mg/kg, or from about 5 mg/kg to about 6 mg/kg per dose.

In some embodiments, heparin may be administered at about 10 IU/kg, about 20 IU/kg, about 30 IU/kg, about 40 IU/kg, about 50 IU/kg, about 60 IU/kg, about 70 IU/kg, about 80 IU/kg, about 90 IU/kg, about 100 IU/kg, about 120 IU/kg, about 140 IU/kg, about 160 IU/kg, about 180 IU/kg, about 200 IU/kg, about 220 IU/kg, about 240 IU/kg, about 260 IU/kg, about 280 IU/kg, about 300 IU/kg, about 350 IU/kg, about 400 IU/kg, about 450 IU/kg, about 500 IU/kg, about 550 IU/kg, or about 600 IU/kg per dose. In some embodiments, heparin may be administered at from about 10 IU/kg to about 100 IU/kg, from about 10 IU/kg to about 200 IU/kg, from about 10 IU/kg to about 300 IU/kg, from about 10 IU/kg to about 400 IU/kg, from about 10 IU/kg to about 500 IU/kg, from about 10 IU/kg to about 600 IU/kg, from about 50 IU/kg to about 100 IU/kg, from about 50 IU/kg to about 200 IU/kg, from about 50 IU/kg to about 300 IU/kg, from about 50 IU/kg to about 400 IU/kg, from about 50 IU/kg to about 500 IU/kg, from about 50 IU/kg to about 600 IU/kg, from about 100 IU/kg to about 200 IU/kg, from about 100 IU/kg to about 300 IU/kg, from about 100 IU/kg to about 400 IU/kg, from about 100 IU/kg to about 500 IU/kg, from about 100 IU/kg to about 600 IU/kg, from about 200 IU/kg to about 300 IU/kg, from about 200 IU/kg to about 400 IU/kg, from about 200 IU/kg to about 500 IU/kg, from about 200 IU/kg to about 600 IU/kg, from about 300 IU/kg to about 400 IU/kg, from about 300 IU/kg to about 500 IU/kg, from about 300 IU/kg to about 600 IU/kg, from about 400 IU/kg to about 500 IU/kg, from about 400 IU/kg to about 600 IU/kg, or from about 500 IU/kg to about 600 IU/kg per dose. International standard units (IU) of heparin may the anti-Factor Xa activity of heparin. Anti-factor Xa activity of heparin may be based on reference to the W.H.O. First International Low Molecular Weight Heparin Reference Standard.

In some embodiments, heparin may be administered at about 10 mg, about 20 mg, about 30 mg, about 40 mg, about 50 mg, about 60 mg, about 70 mg, about 80 mg, about 90 mg, about 100 mg, about 120 mg, about 140 mg, about 160 mg, about 180 mg, about 200 mg, about 220 mg, about 240 mg, about 260 mg, about 280 mg, about 300 mg, about 350 mg, about 400 mg, about 450 mg, about 500 mg, about 550 mg, or about 600 mg per dose. In some embodiments, heparin may be administered at from about 10 mg to about 100 mg, from about 10 mg to about 200 mg, from about 10 mg to about 300 mg, from about 10 mg to about 400 mg, from about 10 mg to about 500 mg, from about 10 mg to about 600 mg, from about 50 mg to about 100 mg, from about 50 mg to about 200 mg, from about 50 mg to about 300 mg, from about 50 mg to about 400 mg, from about 50 mg to about 500 mg, from about 50 mg to about 600 mg, from about 100 mg to about 200 mg, from about 100 mg to about 300 mg, from about 100 mg to about 400 mg, from about 100 mg to about 500 mg, from about 100 mg to about 600 mg, from about 200 mg to about 300 mg, from about 200 mg to about 400 mg, from about 200 mg to about 500 mg, from about 200 mg to about 600 mg, from about 300 mg to about 400 mg, from about 300 mg to about 500 mg, from about 300 mg to about 600 mg, from about 400 mg to about 500 mg, from about 400 mg to about 600 mg, or from about 500 mg to about 600 mg per dose.

In some embodiments, N-acetylcysteine may be administered at about 20 mg, about 40 mg, about 60 mg, about 80 mg, about 100 mg, about 120 mg, about 140 mg, about 160 mg, about 180 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg per dose. In some embodiments, N-acetylcysteine may be administered at from about 20 mg to about 200 mg, from about 20 mg to about 400 mg, from about 20 mg to about 600 mg, from about 20 mg to about 800 mg, from about 50 mg to about 1000 mg, from about 50 mg to about 200 mg, from about 50 mg to about 400 mg, from about 50 mg to about 600 mg, from about 50 mg to about 800 mg, from about 50 mg to about 1000 mg, from about 100 mg to about 200 mg, from about 100 mg to about 400 mg, from about 100 mg to about 600 mg, from about 100 mg to about 800 mg, from about 100 mg to about 1000 mg, from about 200 mg to about 400 mg, from about 200 mg to about 600 mg, from about 200 mg to about 800 mg, from about 200 mg to about 1000 mg, from about 400 mg to about 600 mg, from about 400 mg to about 800 mg, from about 400 mg to about 1000 mg, from about 600 mg to about 800 mg, from about 600 mg to about 1000 mg, or from about 800 mg to about 1000 mg per dose.

Treatment Plans

A method or a composition of the present disclosure may be used in a treatment plan for an individual at a stage of a viral infection (e.g., a coronavirus infection). A stage of a viral infection may be an asymptomatic stage, a mildly symptomatic stage, or a severely symptomatic stage. In some embodiments, an individual at an asymptomatic stage may be positive for the viral infection but may not showing symptoms, or the individual may have been exposed to the virus or may be at high risk of being exposed to the virus but has not tested positive for the viral infection. In some embodiments, an individual at a mildly symptomatic stage may be showing symptoms of the viral infection. The symptoms may not be severe enough to require mechanical ventilation. An individual at the mildly symptomatic stage may have tested positive for the viral infection, or the individual may be presumed positive for the viral infection. In some embodiments, an individual at the severely symptomatic stage may have severe symptoms of the viral infection. The severe symptoms may require mechanical ventilation. An individual at the severely symptomatic stage may have tested positive for the viral infection, or the individual may be presumed positive for the viral infection. In some embodiments, a composition may be administered during a viral incubation period. A composition may be administered to an individual after the individual has been exposed to or may have been exposed to a virus (e.g., a coronavirus) but before the individual shows symptoms of the virus. For example, a composition may be individual during the 5-day incubation period of a SARS-COV-2 infection.

A treatment plan for an individual at an asymptomatic stage of a viral infection (e.g., a coronavirus infection) may comprise administering a composition (e.g., heparin and NAC) to the individual. In some embodiments, the composition may be administered via inhalation (e.g., via a nebulizer). The composition may be administered orally. The composition may be administered intranasally. In some embodiments, the composition may be administered at a low dose. The composition may prevent the viral infection, or the composition may slow development or reduce the severity of symptoms associated with the viral infection. The composition may reduce the infectivity of the viral infection. A treatment plan for an individual at an asymptomatic stage of a viral infection (e.g., a coronavirus infection) may comprise administering heparin (e.g., low molecular weight heparin), N-acetylcysteine, or a combination thereof. The heparin, N-acetylcysteine, or both may be administered by inhalation (e.g., via a nebulizer). The heparin, N-acetylcysteine, or both may be administered orally. The heparin, N-acetylcysteine, or both may be administered intranasally. In some embodiments, the heparin, N-acetylcysteine, or both may be administered at a low dose. The heparin, N-acetylcysteine, or both may prevent the viral infection, or the heparin, N-acetylcysteine, or both may slow development or reduce the severity of symptoms associated with the viral infection. The heparin, N-acetylcysteine, or both may reduce the infectivity of the virus.

A treatment plan for an individual at a mildly symptomatic stage of a viral infection (e.g., a coronavirus infection) may comprise administering a composition (e.g., heparin and NAC) to the individual. In some embodiments, the composition may be administered via inhalation (e.g., via a nebulizer). The composition may be administered orally. The composition may be administered intranasally. In some embodiments, the composition may be administered at a moderate dose. The composition may slow development or reduce the severity of symptoms associated with the viral infection. A treatment plan for an individual at a mildly symptomatic stage of a viral infection (e.g., a coronavirus infection) may comprise administering heparin, N-acetylcysteine, or a combination thereof. The heparin, N-acetylcysteine, or both may be administered by inhalation (e.g., via a nebulizer). The heparin, N-acetylcysteine, or both may be administered orally. The heparin, N-acetylcysteine, or both may be administered intranasally. In some embodiments, the heparin, N-acetylcysteine, or both may be administered at a moderate dose. The heparin, N-acetylcysteine, or both may slow development or reduce the severity of symptoms associated with the viral infection. The treatment plan for an individual at a mildly symptomatic stage of a viral infection may further comprise administering an additional antiviral agent (e.g., chloroquine, Remdesivir, Tocilizumab, Lopinavir, Sarilumab, hydroxychloroquine, interferon-beta, or a combination thereof).

A treatment plan for an individual at a severely symptomatic stage of a viral infection (e.g., a coronavirus infection) may comprise administering a composition (e.g., heparin and NAC) to the individual. The composition may be administered orally. The composition may be administered by inhalation (e.g., through a side port of a ventilator or via a nebulizer). In some embodiments, the composition may be administered at a high dose. The composition may reduce the severity of symptoms associated with the viral infection, or the composition may decrease the duration of mechanical ventilation of the individual. A treatment plan for an individual at a severely symptomatic stage of a viral infection (e.g., a coronavirus infection) may comprise administering heparin, N-acetylcysteine, or a combination thereof. The heparin, N-acetylcysteine, or both may be administered orally. The heparin, N-acetylcysteine, or both may be administered by inhalation (e.g., through a side port of a ventilator or via a nebulizer). In some embodiments, the heparin, N-acetylcysteine, or both may be administered at a high dose. The heparin, N-acetylcysteine, or both may reduce the severity of symptoms associated with the viral infection, or the heparin, N-acetylcysteine, or both may decrease the duration of mechanical ventilation of the individual. The heparin, N-acetylcysteine, or both may reduce the infectivity of a virus (e.g., a coronavirus). The treatment plan for an individual at a severely symptomatic stage of a viral infection may further comprise administering an additional antiviral agent (e.g., chloroquine, hydroxychloroquine, Remdesivir, Tocilizumab, Lopinavir, Sarilumab, interferon-beta, or a combination thereof).

A treatment plan may be selected for an individual having a viral infection or at risk of having a viral infection based on one or more risk factors. For example, a treatment course may not utilize an active agent if the individual has one or more risk factors that may increase the likelihood of an adverse effect of the active agent. An active agent may not be administered to an individual if the individual has had an allergic reaction to the active agent. A treatment plan comprising administering one or more active agents may be stopped if the individual develops an adverse side effect. For example, a treatment plan may be stopped if the individual shows symptoms of an adverse reaction (e.g., rash, dizziness, shortness of breath, itching, swelling, slow heartbeat, heart failure, fatigue, mood change, sign of infection, sign of liver disease, weakness, hair loss, skin color change, hair color change, hearing change, uncontrolled movements, nausea, vomiting, diarrhea, headache, low blood sugar, or vision impairment). In some embodiments, a composition of the present disclosure may be administered to a subject with increased genetic expression of ACE virus binding proteins. For example, a subject with an ethnic background (e.g., East Asian) linked to an increased expression of ACE virus binding proteins may be a preferred patient population for treatment with a composition of the present disclosure. In some embodiments, a subject taking an ACE inhibitor may be a preferred patient population for treatment with a composition of the present disclosure. In some embodiments, a composition of the present disclosure may be administered in combination with an ACE inhibitor.

In some embodiments, a composition may be administered orally. In some embodiments, a composition may be administered via inhalation. For example, a composition may be administered using a nebulizer. In some embodiments, a composition may be administered to a subject breathing with assistance of a ventilator. For example, a composition may be administered to a subject by inhalation through a port of a ventilator using a nebulizer. Any mode of delivery may be used, including, but not limited to, oral, anal, parenteral, intravenous, or intrathecal delivery.

Administration

A method of the present disclosure may comprise administering a composition comprising a heparin (e.g., bemiparin, nadroparin, reviparin, enoxaparin, parnaparin, certoparin, dalteparin, danaparoid, or tinzaparin). The composition may comprise from 500 IU to 1000 IU, from 1000 IU to 1500 IU, from 1500 IU to 2000 IU, from 2000 IU to 2500 IU, from 2500 IU to 3000 IU, from 3000 IU to 3500 IU, from 3500 IU to 4000 IU, from 4000 IU to 4500 IU, from 4500 IU to 5000 IU, from 5000 IU to 5500 IU, from 5500 IU to 6000 IU, from 6000 IU to 6500 IU, from 6500 IU to 7000 IU, from 7000 IU to 7500 IU, from 7500 IU to 8000 IU, from 8000 IU to 8500 IU, from 8500 IU to 9000 IU, from 9000 IU to 9500 IU, from 9500 IU to 10000 IU, from 10000 IU to 20000 IU, from 20000 IU to 30000 IU, from 30000 IU to 40000 IU, from 40000 IU to 50000 IU, from 50000 IU to 60000 IU, from 60000 IU to 70000 IU, from 70000 IU to 80000 IU, from 80000 IU to 90000 IU, from 90000 IU to 100000 IU, from 100000 IU to 110000 IU, from 110000 IU to 120000 IU, from 120000 IU to 130000 IU, from 130000 IU to 140000 IU, from 140000 IU to 150000 IU, from 150000 IU to 160000 IU, from 160000 IU to 170000 IU, from 170000 IU to 180000 IU, from 180000 IU to 190000 IU, or from 190000 IU to 200000 IU of polyanionic electrolyte. In some embodiments, from 500 IU to 1000 IU, from 1000 IU to 1500 IU, from 1500 IU to 2000 IU, from 2000 IU to 2500 IU, from 2500 IU to 3000 IU, from 3000 IU to 3500 IU, from 3500 IU to 4000 IU, from 4000 IU to 4500 IU, from 4500 IU to 5000 IU, from 5000 IU to 5500 IU, from 5500 IU to 6000 IU, from 6000 IU to 6500 IU, from 6500 IU to 7000 IU, from 7000 IU to 7500 IU, from 7500 IU to 8000 IU, from 8000 IU to 8500 IU, from 8500 IU to 9000 IU, from 9000 IU to 9500 IU, from 9500 IU to 10000 IU, from 10000 IU to 20000 IU, from 20000 IU to 30000 IU, from 30000 IU to 40000 IU, from 40000 IU to 50000 IU, from 50000 IU to 60000 IU, from 60000 IU to 70000 IU, from 70000 IU to 80000 IU, from 80000 IU to 90000 IU, from 90000 IU to 100000 IU, from 100000 IU to 110000 IU, from 110000 IU to 120000 IU, from 120000 IU to 130000 IU, from 130000 IU to 140000 IU, from 140000 IU to 150000 IU, from 150000 IU to 160000 IU, from 160000 IU to 170000 IU, from 170000 IU to 180000 IU, from 180000 IU to 190000 IU, or from 190000 IU to 200000 IU of heparin may be administered to a subject per day. In some embodiments, from 20,000 IU to 100,000 IU, or from 20,000 IU to 70,000 IU of the heparin (e.g., bemiparin, nadroparin, reviparin, enoxaparin, parnaparin, certoparin, dalteparin, or tinzaparin) may be administered to the subject per day. The terms "international standard units," "IU," and "units" are used interchangeably herein to refer to an amount of an active compound. International standard units (IU) of heparin may the anti-Factor Xa activity of heparin. Anti-factor Xa activity of heparin may be based on reference to the W.H.O. First International Low Molecular Weight Heparin Reference Standard.

A method of the present disclosure may comprise administering a composition comprising an antioxidant (e.g., N-acetylcysteine). The composition may comprise from 10 mg to 50 mg, from 50 mg to 100 mg, from 100 mg to 150 mg, from 150 mg to 200 mg, from 200 mg to 250 mg, from 250 mg to 300 mg, from 300 mg to 350 mg, from 350 mg to 400 mg, from 400 mg to 450 mg, from 450 mg to 500 mg, from 500 mg to 550 mg, from 550 mg to 600 mg, from 600 mg to 650 mg, from 650 mg to 700 mg, from 700 mg to 750 mg, from 750 mg to 800 mg, from 800 mg to 850 mg, from 850 mg to 900 mg, from 900 mg to 950 mg, from 950 mg to 1000 mg, from 1000 mg to 2000 mg, from 2000 mg to 3000 mg, from 3000 mg to 4000 mg, from 4000 mg to 5000 mg, or from 5000 mg to 10000 mg of antioxidant. In some embodiments, from 10 mg to 50 mg, from 50 mg to 100 mg, from 100 mg to 150 mg, from 150 mg to 200 mg, from 200 mg to 250 mg, from 250 mg to 300 mg, from 300 mg to 350 mg, from 350 mg to 400 mg, from 400 mg to 450 mg, from 450 mg to 500 mg, from 500 mg to 550 mg, from 550 mg to 600 mg, from 600 mg to 650 mg, from 650 mg to 700 mg, from 700 mg to 750 mg, from 750 mg to 800 mg, from 800 mg to 850 mg, from 850 mg to 900 mg, from 900 mg to 950 mg, from 950 mg to 1000 mg, from 1000 mg to 2000 mg, from 2000 mg to 3000 mg, from 3000 mg to 4000 mg, from 4000 mg to 5000 mg, or from 5000 mg to 10000 mg of antioxidant may be administered to a subject per day. In some embodiments, from 1 g to 30 g, from 1 g to 20 g, from 1 g to 10 g, or from 1 g to 5 g of antioxidant (e.g., N-acetylcysteine) may be administered to a subject per day.

A method of the present disclosure may comprise administering a composition comprising a PBCS peptide (e.g., a peptide comprising an RXXR motif or an RXXK motif). The composition may comprise from 1 mg to 10 mg, from 10 mg to 50 mg, from 50 mg to 100 mg, from 100 mg to 150 mg, from 1 mg to 160 mg, from 150 mg to 200 mg, from 200 mg to 250 mg, from 250 mg to 300 mg, from 300 mg to 350 mg, from 350 mg to 400 mg, from 400 mg to 450 mg, or from 450 mg to 500 mg of the PBCS peptide. In some embodiments, from 1 mg to 10 mg, from 10 mg to 50 mg, from 50 mg to 100 mg, from 100 mg to 150 mg, from 1 mg to 160 mg, from 150 mg to 200 mg, from 200 mg to 250 mg, from 250 mg to 300 mg, from 300 mg to 350 mg, from 350 mg to 400 mg, from 400 mg to 450 mg, or from 450 mg to 500 mg of the PBCS peptide may be administered to a subject per day.

A composition of the present disclosure may be administered 1, 2, 3, 4, 5, 6, 7, 8, 9, 10, 11, 12, 13, 14, 15, 16, 17, 18, 19, 20, 21, 22, 23, or 24 times per day. In some embodiments, a composition (e.g., a composition formulated for inhalation) may be administered over a duration of from about 1 hour to about 2 hours, from about 2 hours to about 3 hours, from about 3 hours to about 4 hours, from about 4 hours to about 5 hours, from about 5 hours to about 6 hours, from about 6 hours to about 7 hours, from about 7 hours to about 8 hours, from about 8 hours to about 9 hours, from about 9 hours to about 10 hours, from about 10 hours to about 11 hours, from about 11 hours to about 12 hours, from about 12 hours to about 13 hours, from about 13 hours to about 14 hours, from about 14 hours to about 15 hours, from about 15 hours to about 16 hours, from about 16 hours to about 17 hours, from about 17 hours to about 18 hours, from about 18 hours to about 19 hours, from about 19 hours to about 20 hours, from about 20 hours to about 21 hours, from about 21 hours to about 22 hours, from about 22 hours to about 23 hours, or from about 23 hours to about 24 hours. In some embodiments, a composition (e.g., a composition comprising heparin and N-acetylcysteine) may be administered for 1, 2, 3, 4, 5, 6, 7, 8, 9, 10, 11, 12, 13, 14, 15, 18, 21, or 28 days. In some embodiments, a composition may be administered 1, 2, 3, 4, 5, 6, 7, 8, 9, 10, 11, 12, 13, or 14 days after a subject was exposed to a viral infection (e.g., a coronavirus infection).

Formulations for Delivery via Inhalation

A method of the present disclosure may comprise administering a composition comprising one or more active agents (e.g., a composition comprising heparin, N-acetylcysteine, or both) to a subject in need thereof via inhalation. The composition may be formulated for delivery via inhalation. A method of treating a respiratory virus (e.g., SARS-CoV or SARS-COV-2) may comprise delivering a composition of the present disclosure to the lungs of a subject in need thereof by administering the composition by inhalation. In some embodiments, a composition formulated for inhalation may be administered using a nasal spray, a nebulizer, a face mask, or a ventilator.

A formulation comprising a composition for nasal or pulmonary deliver may have a pH corresponding to a physiologically acidic nasal pH. The physiologically acidic nasal pH may depend on intact nasal mucosal function. A composition may comprise a pHI of about be 6.5±0.5 (5.9 to 7.3) or about 6.7±0.6 (5.3 to 7.6). A composition may comprise a pH of about 3.8-7.7 (mean±SD 5.7±0.9). A composition for nasal or pulmonary deliver may be in the slightly acidic range. The average pH may have an acidity of pH 5.7.

In some embodiments, a formulation for inhalation via nebulization may comprise a pH of about be 6.5±0.5 (5.9 to 7.3) or about 6.7±0.6 (5.3 to 7.6), or a composition may comprise a pH of about 3.8-7.7 (mean±SD 5.7±0.9).

In some embodiments, a composition may comprise an acid to adjust the pH. For example, a composition may comprise hydrochloric acid, acetic acid, or citric acid. In some embodiments, a composition may comprise a base to adjust the pH. For example, a composition may comprise sodium hydroxide or potassium hydroxide.

In some embodiments, a composition of the present disclosure (e.g., a composition to reduce the infectivity of, treat, or prevent a viral infection) may be formulated to minimize a chloride ion concentration. A chloride ion concentration may be less than about 1 M, less than about 100 mM, less than about 10 mM, less than about 1 mM, less than about 0.1 mM, or less than about 0.01 mM. A chloride ion bound to an ACE-2 inhibitor may have catalytic activity.

Exemplary mucoadhesive polymer-enzyme inhibitor complexes that are useful within the mucosal formulations and methods of the invention include, but are not limited to: heparin, N-acetyl-cysteine, Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil—elastatinal (anti-elastase); Chitosan—antipain (anti-trypsin); Poly(acrylic acid)—bacitracin (anti-aminopeptidase N); Chitosan—EDTA (anti-aminopeptidase N, anti-carboxypeptidase A); Chitosan—EDTA—antipain (anti-trypsin, anti-chymotrypsin, anti-clastase).

Endotoxin-Free Formulations

In some embodiments, an endotoxin-free formulation may be a formulation which contains a Y2-receptor-binding peptide and one or more mucosal delivery enhancing agents. The solution may be substantially free of endotoxins and/or related pyrogenic substances. Endotoxins include toxins that are confined inside a microorganism and are released only when the microorganisms are broken down or die. Pyrogenic substances include fever-inducing, thermostable substances (glycoproteins) from the outer membrane of bacteria and other microorganisms. Both of these substances can cause fever, hypotension and shock if administered to humans. Producing formulations that are endotoxin-free can require special equipment, expert artisans, and can be significantly more expensive than making formulations that are not endotoxin-free.

Mucolytic and Mucus-Clearing Agents and Methods

Effective delivery of therapeutic agents via nasal or pulmonary administration may take into account the decreased drug transport rate across the protective mucus lining of the nasal mucosa, in addition to drug loss due to binding to glycoproteins of the mucus layer. Normal mucus is a viscoelastic, gel-like substance consisting of water, electrolytes, mucins, macromolecules, and sloughed epithelial cells. It serves primarily as a cytoprotective and lubricative covering for the underlying mucosal tissues. Mucus is secreted by randomly distributed secretory cells located in the nasal epithelium and in other mucosal epithelia. The structural unit of mucus is mucin. This glycoprotein is mainly responsible for the viscoelastic nature of mucus, although other macromolecules may also contribute to this property. In airway mucus, such macromolecules include locally produced secretory IgA, IgM, IgE, lysozyme, and bronchotransferrin, which also play an important role in host defense mechanisms.

The coordinate administration methods of the instant invention optionally incorporate effective mucolytic or mucus-clearing agents, which serve to degrade, thin or clear mucus from intranasal mucosal surfaces to facilitate absorption and/or adsorption of intranasally administered biotherapeutic agents. Within these methods, a mucolytic or mucus-clearing agent is coordinately administered as an adjunct compound to enhance intranasal delivery of the biologically active agent. Alternatively, an effective amount of a mucolytic or mucus-clearing agent is incorporated as a processing agent within a multi-processing method of the invention, or as an additive within a combinatorial formulation of the invention, to provide an improved formulation that enhances intranasal delivery of biotherapeutic compounds by reducing the barrier effects of intranasal mucus.

A variety of mucolytic or mucus-clearing agents are available for incorporation within the methods and compositions of the invention. Based on their mechanisms of action, mucolytic and mucus clearing agents can often be classified into the following groups: proteases (e.g., pronase, papain) that cleave the protein core of mucin glycoproteins; sulfhydryl compounds that split mucoprotein disulfide linkages; and detergents (e.g., Triton X-100, Tween 20) that break non-covalent bonds within the mucus. Additional compounds in this context include, but are not limited to, bile salts and surfactants, for example, sodium deoxycholate, sodium taurodeoxycholate, sodium glycocholate, and lysophosphatidylcholine.

The effectiveness of bile salts in causing structural breakdown of mucus is in the order deoxycholate>taurocholate>glycocholate. Other effective agents that reduce mucus viscosity or adhesion to enhance intranasal delivery according to the methods of the invention include, e.g., short-chain fatty acids, and mucolytic agents that work by chelation, such as N-acylcollagen peptides, bile acids, and saponins (the latter function in part by chelating $Ca^{2+}$ and/or $Mg^{2+}$ which play an important role in maintaining mucus layer structure).

Additional mucolytic agents for use within the methods and compositions of the invention include N-acetyl-L-cysteine (ACS), a potent mucolytic agent that reduces both the viscosity and adherence of bronchopulmonary mucus and is reported to modestly increase nasal bioavailability of human growth hormone in anesthetized rats (from 7.5 to 12.2%). These and other mucolytic or mucus-clearing agents are contacted with the nasal mucosa, typically in a concentration range of about 0.2 to 20 mM, coordinately with administration of the biologically active agent, to reduce the polar viscosity and/or elasticity of intranasal mucus.

Still other mucolytic or mucus-clearing agents may be selected from a range of glycosidase enzymes, which are able to cleave glycosidic bonds within the mucus glycoprotein. .alpha.-amylase and .beta.-amylase are representative of this class of enzymes, although their mucolytic effect may be limited. In contrast, bacterial glycosidases which allow these microorganisms to permeate mucus layers of their hosts.

For combinatorial use with most biologically active agents within the invention, including peptide and protein therapeutics, non-ionogenic detergents are generally also useful as mucolytic or mucus-clearing agents. These agents typically will not modify or substantially impair the activity of therapeutic polypeptides.

Ciliostatic Agents and Methods

Because the self-cleaning capacity of certain mucosal tissues (e.g., nasal mucosal tissues) by mucociliary clearance is necessary as a protective function (e.g., to remove dust, allergens, and bacteria), it has been generally considered that this function should not be substantially impaired by mucosal medications. Mucociliary transport in the respiratory tract is a particularly important defense mechanism against infections. To achieve this function, ciliary beating in the nasal and airway passages moves a layer of mucus along the mucosa to removing inhaled particles and microorganisms.

Ciliostatic agents find use within the methods and compositions of the invention to increase the residence time of mucosally (e.g., intranasally or pulmonary) administered biologically active agents against viruses disclosed herein. In particular, the delivery these agents within the methods and compositions of the invention is significantly enhanced in certain aspects by the coordinate administration or combinatorial formulation of one or more ciliostatic agents that function to reversibly inhibit ciliary activity of mucosal cells, to provide for a temporary, reversible increase in the residence time of the mucosally administered active agent (s). For use within these aspects of the invention, the foregoing ciliostatic factors, either specific or indirect in their activity, are all candidates for successful employment as ciliostatic agents in appropriate amounts (depending on concentration, duration and mode of delivery) such that they yield a transient (i.e., reversible) reduction or cessation of mucociliary clearance at a mucosal site of administration to enhance delivery of biologically active agents disclosed herein, without unacceptable adverse side effects.

Within more detailed aspects, a specific ciliostatic factor is employed in a combined formulation or coordinate administration protocol with one or more Y2 receptor-binding peptide proteins, analogs and mimetics, and/or other biologically active agents disclosed herein. Various bacterial ciliostatic factors isolated and characterized in the literature may be employed within these embodiments of the invention. Ciliostatic factors from the bacterium *Pseudomonas aeruginosa* include a phenazine derivative, a pyo compound (2-alkyl-4-hydroxyquinolines), and a rhamnolipid (also known as a hemolysin). The pyo compound produced ciliostasis at concentrations of 50 µg/ml and without obvious ultrastructural lesions. The phenazine derivative also inhibited ciliary motility but caused some membrane disruption, although at substantially greater concentrations of 400 µg/ml. Limited exposure of tracheal explants to the rhamnolipid resulted in ciliostasis, which was associated with altered ciliary membranes. More extensive exposure to rhamnolipid was associated with removal of dynein arms from axonemes.

Surface Active Agents and Methods

Within more detailed aspects of the invention, one or more membrane penetration-enhancing agents may be employed within a mucosal delivery method or formulation of the invention to enhance mucosal delivery biologically active agents disclosed herein. Membrane penetration enhancing agents in this context can be selected from: (i) a surfactant, (ii) a bile salt, (iii) a phospholipid additive, mixed micelle, liposome, or carrier, (iv) an alcohol, (v) an enamine, (vi) an NO donor compound, (vii) a long-chain amphipathic molecule (viii) a small hydrophobic penetration enhancer; (ix) sodium or a salicylic acid derivative; (x) a glycerol ester of acetoacetic acid (xi) a clyclodextrin or beta-cyclodextrin derivative, (xii) a medium-chain fatty acid, (xiii) a chelating agent, (xiv) an amino acid or salt thereof, (xv) an N-acety-lamino acid or salt thereof, (xvi) an enzyme degradative to a selected membrane component, (xvii) an inhibitor of fatty acid synthesis, or (xviii) an inhibitor of cholesterol synthesis; or (xix) any combination of the membrane penetration enhancing agents recited in (i) (xix).

Certain surface-active agents are readily incorporated within the mucosal delivery formulations and methods of the invention as mucosal absorption and/or adsorption enhancing agents. These agents, which may be coordinately administered or combinatorially formulated with other biologically active agents disclosed herein, may be selected from a broad assemblage of known surfactants. Surfactants, which generally fall into three classes: (1) nonionic polyoxyethylene ethers; (2) bile salts such as sodium glycocholate (SGC) and deoxycholate (DOC); and (3) derivatives of fusidic acid such as sodium taurodihydrofusidate (STDHF). The mechanisms of action of these various classes of surface-active agents typically include solubilization of the biologically active agent. For proteins and peptides which often form aggregates, the surface active properties of these absorption and/or adsorption promoters can allow interactions with proteins such that smaller units such as surfactant coated monomers may be more readily maintained in solution. Examples of other surface-active agents are L-.alpha.-Phosphatidylcholine Didecanoyl (DDPC) polysorbate 80 and polysorbate 20. These monomers are presumably more transportable units than aggregates. A second potential mechanism is the protection of the peptide or protein from proteolytic degradation by proteases in the mucosal environment. Both bile salts and some fusidic acid derivatives reportedly inhibit proteolytic degradation of proteins by nasal homogenates at concentrations less than or equivalent to those required to enhance protein absorption and/or adsorption. This protease inhibition may be especially important for peptides with short biological half-lives.

Vasodilator Agents and Methods

While generally it is intended the formulations of this invention remain on the nasal mucosa to perform their virus inhibiting action, yet another class of absorption and/or adsorption-promoting agents that shows beneficial utility within the coordinate administration and combinatorial formulation methods and compositions of the invention are vasoactive compounds, more specifically vasodilators. These compounds function within the invention to modulate the structure and physiology of the submucosal vasculature, increasing the transport rate of biologically active agents into or through the mucosal epithelium and/or to specific target tissues or compartments (e.g., the systemic circulation or central nervous system.).

Vasodilator agents for use within the invention typically cause submucosal blood vessel relaxation by either a decrease in cytoplasmic calcium, an increase in nitric oxide (NO) or by inhibiting myosin light chain kinase. They are generally divided into 9 classes: calcium antagonists, potassium channel openers, ACE inhibitors, angiotensin-II receptor antagonists, .alpha.-adrenergic and imidazole receptor antagonists, .beta.1-adrenergic agonists, phosphodiesterase inhibitors, eicosanoids and NO donors.

Despite chemical differences, the pharmacokinetic properties of calcium antagonists are similar. Absorption and/or adsorption into the systemic circulation is high, and these agents therefore undergo considerable first-pass metabolism by the liver, resulting in individual variation in pharmacokinetics. Except for the newer drugs of the dihydropyridine type (amlodipine, felodipine, isradipine, nilvadipine, nisoldipine and nitrendipine), the half-life of calcium antagonists is short. Therefore, to maintain an effective drug concentration for many of these may require delivery by multiple dosing, or controlled release formulations, as described elsewhere herein. Treatment with the potassium channel opener minoxidil may also be limited in manner and level of administration due to potential adverse side effects.

ACE inhibitors prevent conversion of angiotensin-I to angiotensin-II, and are most effective when renin production is increased. Since ACE is identical to kininase-II, which inactivates the potent endogenous vasodilator bradykinin, ACE inhibition causes a reduction in bradykinin degradation. ACE inhibitors provide the added advantage of cardioprotective and cardioreparative effects, by preventing and reversing cardiac fibrosis and ventricular hypertrophy in animal models. The predominant elimination pathway of most ACE inhibitors is via renal excretion. Therefore, renal impairment is associated with reduced elimination and a dosage reduction of 25 to 50% is recommended in patients with moderate to severe renal impairment.

With regard to NO donors, these compounds are particularly useful within the invention for their additional effects on mucosal permeability. In addition to the above-noted NO donors, complexes of NO with nucleophiles called NO/nucleophiles, or NONOates, spontaneously and nonenzymatically release NO when dissolved in aqueous solution at physiologic pH. In contrast, nitro vasodilators such as nitroglycerin require specific enzyme activity for NO release. NONOates release NO with a defined stoichiometry and at predictable rates ranging from <3 minutes for diethylamine/NO to approximately 20 hours for diethylenetriamine/NO (DETANO).

Polymeric Delivery Vehicles and Methods

Within certain aspects of the invention, biologically active agents disclosed herein, and delivery-enhancing agents as described above, are, individually or combinatorially, incorporated within a mucosally (e.g., nasally or pulmonary) administered formulation that includes a biocompatible polymer functioning as a carrier or base. Such polymer carriers include polymeric powders, matrices or microparticulate delivery vehicles, among other polymer forms. The polymer can be of plant, animal, or synthetic origin. Often the polymer is crosslinked. Additionally, in these delivery systems the Virus entry and infectivity inhibitor, can be functionalized in a manner where it can be covalently bound to the polymer and rendered inseparable from the polymer by simple washing. In other embodiments, the polymer is chemically modified with an inhibitor of enzymes or other agents which may degrade or inactivate the biologically active agent(s) and/or delivery enhancing agent(s). In certain formulations, the polymer is a partially or completely water insoluble but water swellable polymer, e.g., a hydrogel. Polymers useful in this aspect of the invention are desirably water interactive and/or hydrophilic in nature to absorb significant quantities of water, and they often form hydrogels when placed in contact with water or aqueous media for a period of time sufficient to reach equilibrium with water. In more detailed embodiments, the polymer is a hydrogel which, when placed in contact with excess water, absorbs at least two times its weight of water at equilibrium when exposed to water at room temperature.

Drug delivery systems based on biodegradable polymers are preferred in many biomedical applications because such systems are broken down either by hydrolysis or by enzymatic reaction into non-toxic molecules. The rate of degradation is controlled by manipulating the composition of the biodegradable polymer matrix. These types of systems can therefore be employed in certain settings for long-term release of biologically active agents. Biodegradable polymers such as poly(glycolic acid) (PGA), poly-(lactic acid) (PLA), and poly(D,L-lactic-co-glycolic acid) (PLGA), have received considerable attention as possible drug delivery carriers, since the degradation products of these polymers have been found to have low toxicity. During the normal metabolic function of the body these polymers degrade into carbon dioxide and water. These polymers have also exhibited excellent biocompatibility.

For prolonging the biological activity of virus entry and infectivity inhibitor and other biologically active agents disclosed herein, as well as optional delivery-enhancing agents, these agents may be incorporated into polymeric matrices, e.g., polyorthoesters, polyanhydrides, or polyesters. This yields sustained activity and release of the active agent(s), e.g., as determined by the degradation of the polymer matrix. Although the encapsulation of biotherapeutic molecules inside synthetic polymers may stabilize them during storage and delivery, the largest obstacle of polymer-based release technology is the activity loss of the therapeutic molecules during the formulation processes that often involve heat, sonication or organic solvents.

Absorption and/or adsorption-promoting polymers contemplated for use within the invention may include derivatives and chemically or physically modified versions of the foregoing types of polymers, in addition to other naturally occurring or synthetic polymers, gums, resins, and other agents, as well as blends of these materials with each other or other polymers, so long as the alterations, modifications or blending do not adversely affect the desired properties, such as water absorption and/or adsorption, hydrogel formation, and/or chemical stability for useful application. In more detailed aspects of the invention, polymers such as nylon, acrylan and other normally hydrophobic synthetic polymers may be sufficiently modified by reaction to become water swellable and/or form stable gels in aqueous media.

Absorption and/or adsorption-promoting polymers of the invention may include polymers from the group of homo- and copolymers based on various combinations of the following vinyl monomers: acrylic and methacrylic acids, acrylamide, methacrylamide, hydroxyethylacrylate or methacrylate, vinylpyrrolidones, as well as polyvinylalcohol and its co- and terpolymers, polyvinylacetate, its co- and terpolymers with the above listed monomers and 2-acrylamido-2-methyl-propanesulfonic acid (AMPS.RTM.). Very useful are copolymers of the above listed monomers with copolymerizable functional monomers such as acryl or methacryl amide acrylate or methacrylate esters where the ester groups are derived from straight or branched chain alkyl, aryl having up to four aromatic rings which may contain alkyl substituents of 1 to 6 carbons; steroidal, sulfates, phosphates or cationic monomers such as N,N-dimethylaminoalkyl (meth)acrylamide, dimethylaminoalkyl (meth)acrylate, (meth)acryloxyalkyltrimethylammonium chloride, (meth) acryloxyalkyldimethylbenzyl ammonium chloride.

Additional absorption and/or adsorption-promoting polymers for use within the invention are those classified as dextrans, dextrins, and from the class of materials classified as natural gums and resins, or from the class of natural polymers such as processed collagen, chitin, chitosan, pullalan, zooglan, alginates and modified alginates such as "Kelcoloid" (a polypropylene glycol modified alginate) gellan gums such as "Kelocogel", Xanathan gums such as "Keltrol", estastin, alpha hydroxy butyrate and its copolymers, hyaluronic acid and its derivatives, polylactic and glycolic acids.

A very useful class of polymers applicable within the instant invention are olefinically-unsaturated carboxylic acids containing at least one activated carbon-to-carbon olefinic double bond, and at least one carboxyl group; that is, an acid or functional group readily converted to an acid containing an olefinic double bond which readily functions in polymerization because of its presence in the monomer molecule, either in the alpha-beta position with respect to a carboxyl group, or as part of a terminal methylene grouping. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule.

Representative acrylates useful as absorption and/or adsorption-promoting agents within the invention include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate and methacrylate versions thereof. Mixtures of two or three or more long chain acrylic esters may be successfully polymerized with one of the carboxylic monomers. Other comonomers include olefins, including alpha olefins, vinyl ethers, vinyl esters, and mixtures thereof.

Other vinylidene monomers, including the acrylic nitriles, may also be used as absorption and/or adsorption-promoting agents within the methods and compositions of the invention to enhance delivery and adsorption of one or more Y2 receptor-binding peptide proteins, analogs and mimetics, and other biologically active agent(s), including to enhance delivery of the active agent(s) to a target tissue or compartment in the subject (e.g., the liver, hepatic portal vein, CNS tissue or fluid, or blood plasma). Useful alpha, beta-olefinically unsaturated nitriles are preferably monoolefinically unsaturated nitriles having from 3 to 10 carbon atoms such as acrylonitrile, methacrylonitrile, and the like. Most preferred are acrylonitrile and methacrylonitrile. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha, beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like.

Yet additional useful absorption and/or adsorption promoting materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chloro-styrene; vinyl and allyl ethers and ketones such as vinyl methyl ether and methyl vinyl ketone; chloroacrylates; cyanoalkyl acrylates such as alpha-cyanomethyl acrylate, and the alpha-, beta-, and gamma-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, methylene-bis-acrylamide, allylpentaerythritol, and the like; and bis(beta-haloalkyl) alkenyl phosphonates such as bis(beta-chloroethyl) vinyl phosphonate and the like as are known to those skilled in the art. Copolymers wherein the carboxy containing monomer is a minor constituent, and the other vinylidene monomers present as major components are readily prepared in accordance with the methods disclosed herein.

When hydrogels are employed as absorption and/or adsorption promoting agents within the invention, these may be composed of synthetic copolymers from the group of acrylic and methacrylic acids, acrylamide, methacrylamide, hydroxyethylacrylate (HEA) or methacrylate (HEMA), and vinylpyrrolidones which are water interactive and swellable. Specific illustrative examples of useful polymers, especially for the delivery of peptides or proteins, are the following types of polymers: (meth)acrylamide and 0.1 to 99 wt. % (meth)acrylic acid; (meth)acrylamides and 0.1 75 wt % (meth)acryloxyethyl trimethyammonium chloride; (meth) acrylamide and 0.1 75 wt % (meth)acrylamide; acrylic acid and 0.1 75 wt % alkyl (meth)acrylates; (meth)acrylamide and 0.1 75 wt % AMPS.RTM. (trademark of Lubrizol Corp.); (meth)acrylamide and 0 to 30 wt % alkyl (meth) acrylamides and 0.1 75 wt % AMPS.RTM.; (meth)acrylamide and 0.1 99 wt. % HEMA; (meth)acrylamide and 0.1 to 75 wt % HEMA and 0.1 to 99% (meth)acrylic acid; (meth) acrylic acid and 0.1 99 wt % HEMA; 50 mole % vinyl ether and 50 mole % maleic anhydride; (meth)acrylamide and 0.1 to 75 wt % (meth)acryloxyalky dimethyl benzylammonium chloride; (meth)acrylamide and 0.1 to 99 wt % vinyl pyrrolidone; (meth)acrylamide and 50 wt % vinyl pyrrolidone and 0.1 99.9 wt % (meth)acrylic acid; (meth)acrylic acid and 0.1 to 75 wt % AMPS.RTM. and 0.1 75 wt % alkyl (meth)acrylamide. In the above examples, alkyl means $C_1$ to $C_{30}$, preferably $C_1$ to $C_{22}$, linear and branched and $C_4$ to $C_{16}$ cyclic; where (meth) is used, it means that the monomers with and without the methyl group are included. Other very useful hydrogel polymers are swellable, but insoluble versions of poly(vinyl pyrrolidone) starch, carboxymethyl cellulose and polyvinyl alcohol.

Additional polymeric hydrogel materials useful within the invention include (poly) hydroxyalkyl (meth)acrylate: anionic and cationic hydrogels: poly(electrolyte) complexes; poly(vinyl alcohols) having a low acetate residual: a swellable mixture of crosslinked agar and crosslinked carboxymethyl cellulose: a swellable composition comprising methyl cellulose mixed with a sparingly crosslinked agar; a water swellable copolymer produced by a dispersion of finely divided copolymer of maleic anhydride with styrene, ethylene, propylene, or isobutylene; a water swellable polymer of N-vinyl lactams; swellable sodium salts of carboxymethyl cellulose; and the like.

Other gelable, fluid imbibing and retaining polymers useful for forming the hydrophilic hydrogel for mucosal delivery of biologically active agents within the invention include pectin; polysaccharides such as agar, acacia, karaya, tragacenth, algins and guar and their crosslinked versions; acrylic acid polymers, copolymers and salt derivatives, polyacrylamides; water swellable indene maleic anhydride polymers; starch graft copolymers; acrylate type polymers and copolymers with water absorbability of about 2 to 400 times its original weight; diesters of polyglucan; a mixture of crosslinked poly(vinyl alcohol) and poly(N-vinyl-2-pyrrolidone); polyoxybutylene-polyethylene block copolymer gels; carob gum; polyester gels; poly urea gels; polyether gels; polyamide gels; polyimide gels; polypeptide gels; polyamino acid gels; poly cellulosic gels; crosslinked indene-maleic anhydride acrylate polymers; and polysaccharides.

Synthetic hydrogel polymers for use within the invention may be made by an infinite combination of several monomers in several ratios. The hydrogel can be crosslinked and generally possesses the ability to imbibe and absorb fluid and swell or expand to an enlarged equilibrium state. The hydrogel typically swells or expands upon delivery to the nasal mucosal surface, absorbing about 2 5, 5 10, 10 50, up to 50 100 or more times fold its weight of water. The optimum degree of swellability for a given hydrogel will be determined for different biologically active agents depending upon such factors as molecular weight, size, solubility and diffusion characteristics of the active agent carried by or entrapped or encapsulated within the polymer, and the specific spacing and cooperative chain motion associated with each individual polymer.

Hydrophilic polymers useful within the invention are water insoluble but water swellable. Such water-swollen polymers as typically referred to as hydrogels or gels. Such gels may be conveniently produced from water-soluble polymer by the process of crosslinking the polymers by a suitable crosslinking agent. However, stable hydrogels may also be formed from specific polymers under defined conditions of pH, temperature and/or ionic concentration, according to know methods in the art. Typically the polymers are cross-linked, that is, cross-linked to the extent that the polymers possess good hydrophilic properties, have improved physical integrity (as compared to non cross-linked polymers of the same or similar type) and exhibit improved ability to retain within the gel network both the biologically active agent of interest and additional compounds for coadministration therewith such as a cytokine or enzyme inhibitor, while retaining the ability to release the active agent(s) at the appropriate location and time.

Generally hydrogel polymers for use within the invention are crosslinked with a difunctional cross-linking in the amount of from 0.01 to 25 weight percent, based on the weight of the monomers forming the copolymer, and more preferably from 0.1 to 20 weight percent and more often from 0.1 to 15 weight percent of the crosslinking agent. Another useful amount of a crosslinking agent is 0.1 to 10 weight percent. Tri, tetra or higher multifunctional crosslinking agents may also be employed. When such reagents are utilized, lower amounts may be required to attain equivalent crosslinking density, i.e., the degree of crosslinking, or network properties that are sufficient to contain effectively the biologically active agent(s).

The crosslinks can be covalent, ionic or hydrogen bonds with the polymer possessing the ability to swell in the presence of water containing fluids. Such crosslinkers and crosslinking reactions are known to those skilled in the art and in many cases are dependent upon the polymer system. Thus a crosslinked network may be formed by free radical copolymerization of unsaturated monomers. Polymeric hydrogels may also be formed by crosslinking preformed polymers by reacting functional groups found on the polymers such as alcohols, acids, amines with such groups as glyoxal, formaldehyde or glutaraldehyde, bis anhydrides and the like.

The polymers also may be cross-linked with any polyene, e.g. decadiene or trivinyl cyclohexane; acrylamides, such as N,N-methylene-bis(acrylamide); polyfunctional acrylates, such as trimethylol propane triacrylate; or polyfunctional vinylidene monomer containing at least 2 terminal $CH_2<$groups, including, for example, divinyl benzene, divinyl naphthlene, allyl acrylates and the like. In certain embodiments, cross-linking monomers for use in preparing the copolymers are polyalkenyl polyethers having more than one alkenyl ether grouping per molecule, which may optionally possess alkenyl groups in which an olefinic double bond is present attached to a terminal methylene grouping (e.g., made by the etherification of a polyhydric alcohol containing at least 2 carbon atoms and at least 2 hydroxyl groups). Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Efficiency of the polyether cross-linking agent increases with the number of potentially polymerizable groups on the molecule. Typically, polyethers containing an average of two or more alkenyl ether groupings per molecule are used. Other cross-linking monomers include for example, diallyl esters, dimethallyl ethers, allyl or methallyl acrylates and acrylamides, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide suitable polymers. When the cross-linking agent is present, the polymeric mixtures usually contain between about 0.01 to 20 weight percent, e.g., 1%, 5%, or 10% or more by weight of cross-linking monomer based on the total of carboxylic acid monomer, plus other monomers.

In more detailed aspects of the invention, mucosal delivery of biologically active agents disclosed herein, is enhanced by retaining the active agent(s) in a slow-release or enzymatically or physiologically protective carrier or vehicle, for example a hydrogel that shields the active agent from the action of the degradative enzymes. In certain embodiments, the active agent is bound by chemical means to the carrier or vehicle, to which may also be admixed or bound additional agents such as enzyme inhibitors, cytokines, etc. The active agent may alternately be immobilized through sufficient physical entrapment within the carrier or vehicle, e.g., a polymer matrix.

Polymers such as hydrogels useful within the invention may incorporate functional linked agents such as glycosides chemically incorporated into the polymer for enhancing intranasal bioavailability of active agents formulated therewith. Examples of such glycosides are glucosides, fructosides, galactosides, arabinosides, mannosides and their alkyl substituted derivatives and natural glycosides such as arbutin, phlorizin, amygdalin, digitonin, saponin, and indican. There are several ways in which a typical glycoside may be bound to a polymer. For example, the hydrogen of the hydroxyl groups of a glycoside or other similar carbohydrate may be replaced by the alkyl group from a hydrogel polymer to form an ether. Also, the hydroxyl groups of the glycosides may be reacted to esterify the carboxyl groups of a polymeric hydrogel to form polymeric esters in situ. Another approach is to employ condensation of acetobromoglucose with cholest-5-en-3beta-ol on a copolymer of maleic acid. N-substituted polyacrylamides can be synthesized by the reaction of activated polymers with omega-aminoalkylglycosides: (1) (carbohydrate-spacer) (n)-polyacrylamide, 'pseudopolysaccharides'; (2) (carbohydrate spacer) (n)-phosphatidylethanolamine (m)-polyacrylamide, neoglycolipids, derivatives of phosphatidylethanolamine; (3) (carbohydrate-spacer) (n)-biotin (m)-polyacrylamide. These biotinylated derivatives may attach to lectins on the mucosal surface to facilitate absorption and/or adsorption of the biologically active agent(s), e.g., a polymer-encapsulated Y2 receptor-binding peptide.

Within more detailed aspects of the invention, one or more biologically active agents (e.g., a polyanionic electrolyte or an antioxidant), disclosed herein, optionally including secondary active agents such as protease inhibitor(s), cytokine(s), additional modulator(s) of intercellular junctional physiology, etc., are modified and bound to a polymeric carrier or matrix. For example, this may be accomplished by chemically binding a peptide or protein active agent and other optional agent(s) within a crosslinked polymer network. It is also possible to chemically modify the polymer separately with an interactive agent such as a glycosidal containing molecule. In certain aspects, the biologically active agent(s), and optional secondary active agent(s), may be functionalized, i.e., wherein an appropriate reactive group is identified or is chemically added to the active agent(s). Most often an ethylenic polymerizable group is added, and the functionalized active agent is then copolymerized with monomers and a crosslinking agent using a standard polymerization method such as solution polymerization (usually in water), emulsion, suspension or dispersion polymerization. Often, the functionalizing agent is provided with a high enough concentration of functional or polymerizable groups to insure that several sites on the active agent(s) are functionalized. For example, in a polypeptide comprising 16 amine sites, it is generally desired to functionalize at least 2, 4, 5, 7, and up to 8 or more of the sites.

After functionalization, the functionalized active agent(s) is/are mixed with monomers and a crosslinking agent that comprise the reagents from which the polymer of interest is formed. Polymerization is then induced in this medium to create a polymer containing the bound active agent(s). The polymer is then washed with water or other appropriate solvents and otherwise purified to remove trace unreacted impurities and, if necessary, ground or broken up by physical means such as by stirring, forcing it through a mesh, ultrasonication or other suitable means to a desired particle size. The solvent, usually water, is then removed in such a manner as to not denature or otherwise degrade the active agent(s). One desired method is lyophilization (freeze drying) but other methods are available and may be used (e.g., vacuum drying, air drying, spray drying, etc.).

To introduce polymerizable groups in peptides, proteins and other active agents within the invention, it is possible to react available amino, hydroxyl, thiol and other reactive groups with electrophiles containing unsaturated groups. For example, unsaturated monomers containing N-hydroxy succinimidyl groups, active carbonates such as p-nitrophenyl carbonate, trichlorophenyl carbonates, tresylate, oxycarbonylimidazoles, epoxide, isocyanates and aldehyde, and unsaturated carboxymethyl azides and unsaturated orthopyridyl-disulfide belong to this category of reagents. Illustrative examples of unsaturated reagents are allyl glycidyl ether, allyl chloride, allylbromide, allyl iodide, acryloyl chloride, allyl isocyanate, allylsulfonyl chloride, maleic anhydride, copolymers of maleic anhydride and allyl ether, and the like.

All of the lysine active derivatives, except aldehyde, can generally react with other amino acids such as imidazole groups of histidine and hydroxyl groups of tyrosine and the thiol groups of cystine if the local environment enhances nucleophilicity of these groups. Aldehyde containing functionalizing reagents are specific to lysine. These types of reactions with available groups from lysines, cysteines, tyrosine have been extensively documented in the literature and are known to those skilled in the art.

In the case of biologically active agents that contain amine groups, it is convenient to react such groups with an acyloyl chloride, such as acryloyl chloride, and introduce the polymerizable acrylic group onto the reacted agent. Then during preparation of the polymer, such as during the crosslinking of the copolymer of acrylamide and acrylic acid, the functionalized active agent, through the acrylic groups, is attached to the polymer and becomes bound thereto.

In additional aspects of the invention, biologically active agents, including peptides, proteins, nucleosides, and other molecules which are bioactive in vivo, are conjugation-stabilized by covalently bonding one or more active agent(s) to a polymer incorporating as an integral part thereof both a hydrophilic moiety, e.g., a linear polyalkylene glycol, a lipophilic moiety (see, e.g., U.S. Pat. No. 5,681,811). In one aspect, a biologically active agent is covalently coupled with a polymer comprising (i) a linear polyalkylene glycol moiety and (ii) a lipophilic moiety, wherein the active agent, linear polyalkylene glycol moiety, and the lipophilic moiety are conformationally arranged in relation to one another such that the active therapeutic agent has an enhanced in vivo resistance to enzymatic degradation (i.e., relative to its stability under similar conditions in an unconjugated form devoid of the polymer coupled thereto). In another aspect, the conjugation-stabilized formulation has a three-dimensional conformation comprising the biologically active agent covalently coupled with a polysorbate complex comprising (i) a linear polyalkylene glycol moiety and (ii) a lipophilic moiety, wherein the active agent, the linear polyalkylene glycol moiety and the lipophilic moiety are conformationally arranged in relation to one another such that (a) the lipophilic moiety is exteriorly available in the three-dimensional conformation, and (b) the active agent in the composition has an enhanced in vivo resistance to enzymatic degradation.

In a further related aspect, a multiligand conjugated complex is provided which comprises a biologically active agent covalently coupled with a triglyceride backbone moiety through a polyalkylene glycol spacer group bonded at a carbon atom of the triglyceride backbone moiety, and at least one fatty acid moiety covalently attached either directly to a carbon atom of the triglyceride backbone moiety or covalently joined through a polyalkylene glycol spacer moiety (see, e.g., U.S. Pat. No. 5,681,811). In such a multiligand conjugated therapeutic agent complex, the alpha and beta carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the alpha and alpha carbons of the triglyceride backbone moiety, with the bioactive therapeutic agent being covalently coupled with the gamma-carbon of the triglyceride backbone moiety, either being directly covalently bonded thereto or indirectly bonded thereto through a polyalkylene spacer moiety. It will be recognized that a wide variety of structural, compositional, and conformational forms are possible for the multiligand conjugated therapeutic agent complex comprising the triglyceride backbone moiety, within the scope of the invention. It is further noted that in such a multiligand conjugated therapeutic agent complex, the biologically active agent(s) may advantageously be covalently coupled with the triglyceride modified backbone moiety through alkyl spacer groups, or alternatively other acceptable spacer groups, within the scope of the invention. As used in such context, acceptability of the spacer group refers to steric, compositional, and end use application specific acceptability characteristics.

In yet additional aspects of the invention, a conjugation-stabilized complex is provided which comprises a polysorbate complex comprising a polysorbate moiety including a triglyceride backbone having covalently coupled to alpha, alpha and beta carbon atoms thereof functionalizing groups including (i) a fatty acid group; and (ii) a polyethylene glycol group having a biologically active agent or moiety covalently bonded thereto, e.g., bonded to an appropriate functionality of the polyethylene glycol group. Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the biologically active agent or moiety may be covalently bonded.

In yet additional aspects of the invention, a stable, aqueously soluble, conjugation-stabilized complex is provided which comprises one or more biologically active agent(s)+ disclosed herein covalently coupled to a physiologically compatible polyethylene glycol (PEG) modified glycolipid moiety. In such complex, the biologically active agent(s) may be covalently coupled to the physiologically compatible PEG modified glycolipid moiety by a labile covalent bond at a free amino acid group of the active agent, wherein the labile covalent bond is scissionable in vivo by biochemical hydrolysis and/or proteolysis. The physiologically compatible PEG modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monolcate, dioleate, trioleate, monostearate, distearate, and tristearate. In such complex, the physiologically compatible PEG modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids.

Compositions according to the present invention are often administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. The formulations may be presented in multi-dose containers, for example in the sealed dispensing system disclosed in U.S. Pat. No. 4,511,069. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface-active agent, such as a nonionic surfactant (e.g., polysorbate-80), and one or more buffers. In some embodiments of the present invention, the nasal spray solution further comprises a propellant. The pH of the nasal spray solution is optionally between about pH 3.0 and 6.0, preferably 5.0.+−.0.3. Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, chlorobutanol, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5μ mass median equivalent aerodynamic diameter (MMEAD), commonly about 1μ MMEAD, and more typically about 2μ MMEAD. Maximum particle size appropriate for deposition within the nasal passages is often about 10μ MMEAD, commonly about 8μ MMEAD, and more typically about 4μ MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI), which rely on the patient's breath, upon pulmonary or nasal inhalation, to disperse the power into an aerosolized amount. Alternatively, the dry powder may be administered via air-assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

To formulate compositions for mucosal delivery within the present invention, the biologically active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclo-dextrins and derivatives thereof), stabilizers (e.g., serum albumin), and reducing agents (e.g., glutathione) can be included. When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to 3, more typically ½ to 2, and most often ¾ to 1.7.

Administration of Compositions for Viral Inhibition

Diseases from coronaviruses, including SARS-COV-2, can be prevented or treated by administering pharmaceuticals (e.g., the pharmaceutical compositions of the present disclosure) intranasally using a nasal spray or aerosol or via inhalation. This is surprising because coronaviruses are thought to infect the lungs initially and that many inhibitors, proteins and peptides have been shown to be sheared or denatured due to the mechanical forces generated by the actuator in producing the spray or aerosol.

In this area the following definitions are useful. Aerosol is a product that is packaged under pressure and contains therapeutically active ingredients that are released upon activation of an appropriate valve system. Metered aerosol is a pressurized dosage form comprised of metered dose valves, which allow for the delivery of a uniform quantity of spray upon each activation. Powder aerosol is a product that is packaged under pressure and contains therapeutically active ingredients in the form of a powder, which are released upon activation of an appropriate valve system. Spray aerosol is an aerosol product that utilizes a compressed gas as the propellant to provide the force necessary to expel the product as a wet spray; it generally applicable to solutions of medicinal agents in aqueous solvents. Spray is a liquid minutely divided as by a jet of air or steam. Nasal spray drug products contain therapeutically active ingredients dissolved or suspended in solutions or mixtures of excipients in non-pressurized dispensers. Metered spray is a non-pressurized dosage form consisting of valves that allow the dispensing of a specified quantity of spray upon each activation. Suspension spray is a liquid preparation contain-ing solid particles dispersed in a liquid vehicle and in the form of course droplets or as finely divided solids.

The fluid dynamic characterization of the aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps.

Plume Height is the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study. Major Axis is the largest chord that can be drawn within the fitted spray pattern that crosses the COMw in base units (mm). Minor Axis is the smallest chord that can be drawn within the fitted spray pattern that crosses the COMw in base units (mm). Ellipticity Ratio is the ratio of the major axis to the minor axis $D_{10}$ is the diameter of droplet for which 10% of the total liquid volume of sample consists of droplets of a smaller diameter ($\mu$m). $D_{50}$ is the diameter of droplet for which 50% of the total liquid volume of sample consists of droplets of a smaller diameter ($\mu$m), also known as the mass median diameter. D90 is the diameter of droplet for which 90% of the total liquid volume of sample consists of droplets of a smaller diameter ($\mu$m) Span—measurement of the width of the distribution. The smaller the value, the narrower the distribution. Span is calculated as: $(D_{90}-D_{10})$ $D_{50}$. % RSD is the percent relative standard deviation, the standard deviation divided by the mean of the series and multiplied by 100, also known as % CV.

A composition of the present disclosure may be administered nasally in any of the spray patterns described herein. A composition may be administered nasally in from about 0.01 mL to about 0.1 mL, from about 0.05 mL to about 0.15 mL, from about 0.1 mL to about 0.2 mL, from about 0.01 mL to about 0.3 mL, or from about 0.05 mL to about 0.5 mL per spray. A composition of the present disclosure may be administered nasally about 1, 2, 3, 4, 5, 6, 7, 8, 9, or 10 times per day. A composition may be administered nasally for about 1, 2, 3, 4, 5, 6, 7, 8, 9, 10, 11, 12, 13, 14, 15, 16, 17, 18, 19, or 20 days. The total amount of the composition administered during a course of treatment may be from about 1 mL to about 5 mL, from about 2 mL to about 6 mL, from about 3 mL to about 7 mL, from about 4 mL to about 8 mL, from about 5 mL to about 9 mL, from about 6 mL to about 10 mL, from about 7 mL to about 11 mL, from about 8 mL to about 12 mL, from about 9 mL to about 13 mL, or from about 10 mL to about 14 mL.

Pharmaceutical Formulations

A composition of the present disclosure (comprising one or more active agents) may be formulated as a pharmaceutical composition. A pharmaceutical composition may comprise a pharmaceutically acceptable carrier or excipient. As used herein "pharmaceutically acceptable" or "pharmacologically acceptable" includes molecular entities and compositions that do not produce an adverse, allergic or other untoward reaction when administered to a subject, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients are often also incorporated into the compositions.

A pharmaceutical composition comprising an active agent of the present disclosure is formulated according to known methods to prepare pharmaceutically useful compositions, for example, as found in "Excipient Selection in Parenteral Formulation Development" Pramanick et. al., Pharma Times, Vol. 45, No. 3, March 2013, incorporated in its entirety herein by reference. In some aspects, the active agent is combined with a pharmaceutically acceptable carrier. A composition is said to be a pharmaceutically acceptable carrier if its administration is tolerated by a recipient patient. Sterile phosphate-buffered saline is one example of a pharmaceutically acceptable carrier. Other suitable carriers are well-known to those in the art. Sec, for example, Gennaro (ed.), Remington's Pharmaceutical Sciences, 19th Edition (Mack Publishing Company 1995).

Formulations for administration of the active agents of the present disclosure are typically provided but are not limited to as liquid, solid or semi-solid products or dosage forms, exemplified by tablets, capsules, pellets, a powder or a lyophilized product. In some aspects, the active agent is formulated to comprise no additional materials except for a pharmaceutical carrier. In some other aspects, the active agent is formulated such that it comprises a core "matrix material" which encapsulates, binds to, coats or is adjacent to the active agent. In some other aspects, the active agent and matrix material further comprises a protective coatings. Various formulations are well-known to those in the art. See, for example, Gennaro (ed.), Remington's Pharmaceutical Sciences, 19th Edition (Mack Publishing Company 1995).

Suitable excipients for use with the active agents of the present disclosure are often included in formulations for inhalation or for oral delivery. In some embodiments, a composition may be formulated for anal, parenteral, intravenous, or intrathecal delivery. More specifically, formulations which include active agents and one or more but not limited to suitable excipients, exemplified by matrix materials, binders, lubricants, glidants or disintegrates which aid in modulating the pharmacokinetic (PK) profile of administered active agents are preferred. In some aspects, compositions comprising active agents in combination with one or more suitable excipients and one or more specific product characteristics (such as dissolution or water content) which result in improved pharmacokinetic profiles of active agents in vivo. Thus, the in vivo performance of active agent's dosage forms/products included herein is based upon the composition of the excipients added during manufacturing and/or the final product characteristics generated through specific processing parameters and methods. Other excipients are well-known to those in the art. See, for example, Gennaro (ed.), Remington's Pharmaceutical Sciences, 19th Edition (Mack Publishing Company 1995).

Suitable carriers for intravenous administration include for example but are not limited to physiological saline or phosphate buffered saline (PBS), Tris, and solutions containing solubilizing agents, such as glucose, polyethylene glycol, polypropylene glycol, additional agents such as histidine, dextrose, mannitol and mixtures thereof. In some aspects, carriers for intravenous administration include a mixture of histidine and dextrose, Tris and dextrose or Tris and mannitol. Other carriers are well-known to those in the art. See, for example, Gennaro (ed.), Remington's Pharmaceutical Sciences, 19th Edition (Mack Publishing Company 1995).

The formulation often includes an aqueous vehicle. Aqueous vehicles include, by way of example and without limitation, sodium chloride solution, Ringers solution, isotonic dextrose solution, sterile water solution, dextrose and lactated Ringers solution. Nonaqueous vehicles include, by way of example and without limitation, fixed oils of vegetable origin, cottonseed oil, corn oil, sesame oil and peanut oil, benzyl benzoate, castor oil, N,N-dimethylacetamide, ethanol, dehydrated ethanol, glycerin, glycerol, N-methyl-2-pyrrolidone, polyethylene glycol and any derivative thereof, propylene glycol, safflower oil and soybean oil. Other vehicles are well-known to those in the art. See, for example, Gennaro (ed.), Remington's Pharmaceutical Sciences, 19th Edition (Mack Publishing Company 1995).

In some aspects, the composition the pharmaceutically acceptable carrier comprises an osmolyte. In some aspects, the osmolyte comprises a sugar, a sugar alcohol, or a combination thereof.

In certain aspects, the composition comprises a sugar alcohol selected from sorbitol, inositol, mannitol, xylitol and glycerol, or a combination thereof. In further aspects, the sugar alcohol comprises mannitol. In certain aspects, the composition comprises from 2% to 20% (wt/vol %) mannitol. In some aspects, the composition comprises from 2% to 10% (wt/vol %) mannitol. In further aspects, the composition comprises essentially 5% (wt/vol %) mannitol.

In other aspects, the composition comprises a sugar. In certain aspects, the sugar is selected from trehalose, lactose, sucrose, glucose, galactose, maltose, mannose, fructose, dextrose, or a combination thereof. In additional aspects, the sugar is selected from trehalose, sucrose, or a combination thereof. In some aspects, the composition comprises from 1% to 40% (wt/vol %) of trehalose, sucrose, or a combination of trehalose and sucrose. In other aspects, the composition comprises from 1% to 20% (wt/vol %) of trehalose, sucrose, or a combination of trehalose and sucrose. In additional aspects, the composition comprises 2% (wt/vol %) of trehalose, sucrose, or a combination of trehalose and sucrose.

In certain aspects, the composition further comprises an osmolyte selected from glycine, carnitine, cthanolamine, their phosphates, mono sugars, or a combination thereof. In some embodiments, cationic choline can be added to a formulation as a counter ion, for example as a counterion to polyanionic heparin.

In some aspects, the present compositions are isotonic. In other aspects, the compositions are essentially isotonic. In certain aspects, the ionic strength of the composition is less than 50 mM. In other aspects, the ionic strength of the composition is less than 10 mM.

Antimicrobial agents in bacteriostatic or fungistatic concentrations are typically added to preparations packaged in multiple dose containers which include by way of example and without limitation, phenols or cresols, mercurials, benzyl alcohol, chlorobutanol, methyl and propyl p-hydroxybenzoic acid esters, thimerosal, benzalkonium chloride and benzethonium chloride. Other antimicrobial agents are well-known to those in the art. See, for example, Gennaro (ed.), Remington's Pharmaceutical Sciences, 19th Edition (Mack Publishing Company 1995).

Buffers include by way of example and without limitation, acetate, ammonium sulfate, ammonium hydroxide, arginine, aspartic acid, benzene sulfonic acid, benzoate sodium, benzoate acid, carbonate, sodium carbonate, carbon dioxide, citrate, diethanolamine, glucono delta lactone, glycine, glycine HCl, histidine, histidine HCl, hydrochloric acid, hydrobromic acid, lysine maleic acid, meglumine, methanesulfonic acid, monoethanolamine, phosphate, sodium phosphate, citrate, succinate sodium, sulfuric acid, tartarate sodium, tromethamine, sodium citrate, hydroxide, sodium hydroxide, Tris base, Tris base-65, Tris acetate, Tris HCl, and Tris HICI-65.

In various aspects, the pharmaceutically acceptable carrier comprises a buffer. In some aspects, the buffer is selected from tris, HEPES, histidine, ethylene diamine, or a combination thereof. In other aspects, the buffer is selected from tris, histidine, or a combination thereof. In further aspects, the buffer comprises histidine, which is optionally L-histidine. In additional aspects, the composition comprises at least 100 mM histidine. In further aspects, the composition comprises at least 50 mM histidine. In some aspects, the composition comprises at least 20 mM histidine. In additional aspects, the composition comprises 10 to 100 mM histidine. In other aspects, the composition comprises 10 to 20 mM histidine.

Antioxidants include by way of example and without limitation, sodium bisulfate, acetone sodium bisulfate, argon, ascorbyl palmitate, ascorbate sodium, ascorbate acid, butylated hydroxy anisole, butylated hydroxy toluene, cysteine, cystenate HCl, dithionite sodium, gentistic acid, gentistic acid ethanoloamine, glutamate monosodium, glutathione, formaldehyde solfoxylate sodium, metabisulfite potassium, metabisulfite sodium, methionine, monothioglycerol, nitrogen, propyl gallate, sulfite sodium, tocopherol alpha, alpha tocopherol hydrogen succinate and thioglycolyate sodium.

In some aspects, the compositions comprise an antioxidant, a free radical scavenger, a quencher, an antioxidant synergist or a combination thereof.

In some aspects, the antioxidant is selected from methionine, butylated hydroxytoluene, butylated hydroxyanisole, propyl gallate, or a combination thereof. In other aspects, the antioxidant comprises methionine. In further aspects, the antioxidant is L-methionine. In certain aspects, the compositions comprise at least 20 mM methionine. In other aspects, aspects, the compositions comprise at least 10 mM methionine.

Suspending, emulsifying and/or dispersing agents include by way of example and without limitation, sodium carboxymethylcelluose, hydroxypropyl methylcellulose, Polysorbate 80 (TWEEN® 80) and polyvinylpyrrolidone.

In various aspects, the compositions comprise a surfactant. In certain aspects, the surfactant is selected from polysorbate 20, polysorbate 80, a pluronic, polyoxyethylene sorbitan mono-oleate, polyethylene mono-laureate, N-actylglucoside, or a combination thereof. In certain aspects, the surfactant is polysorbate 20. In further aspects, the compositions comprise from 0.0001% to 0.1% (wt/vol %) polysorbate 20. In additional aspects, the compositions comprise cyclodextrin. In further aspects, the cyclodextrin comprises (2-hydroxypropyl)-β-cyclodextrin.

A sequestering or chelating agent of metal ions include by way of example and without limitation, calcium disodium EDTA, disodium EDTA, sodium EDTA, calcium versetaminde sodium, calteridol and DPTA. In some aspects, the present compositions comprise a metal chelator. In certain aspects, the metal chelator is selected from EDTA, deferoxamine mesylate, EGTA, fumaric acid, and malic acid, salts thereof, or combinations thereof. In further aspects, the metal chelator comprises EDTA or salts thereof. In certain aspects, the compositions have an EDTA concentration of about 0.1 mg/ml to about 1.0 mg/ml.

In some embodiments, a composition of the present disclosure (e.g., a composition comprising N-acetylcysteine) may contain disodium edetate at a concentration of about 0.01 mg/ml to about 0.1 mg/ml, about 0.1 mg/ml to about 1.0 mg/ml, about 0.1 mg/ml to about 0.2 mg/ml, about 0.1 mg/ml to about 0.5 mg/ml, about 0.5 mg/ml to about 1.0 mg/ml, about 0.1 mg/ml to about 2.0 mg/ml, about 1.0 mg/ml to about 2.0 mg/ml, about 2.0 mg/ml to about 3.0 mg/ml, or about 3.0 mg/ml to about 5.0 mg/ml.

An example of an N-acetylcysteine formulation for inhalation may comprise acetylcysteine, disodium edetate, sodium hydroxide, and water. In some embodiments, the N-acetylcysteine may be present in the formulation at a concentration of about 20% (w/v).

An example of a heparin formulation for inhalation may comprise enoxaparin sodium and water. In some embodiments, the enoxaparin sodium may be present in the formulation at a concentration of about 100 mg per 1 ml. In some embodiments, the enoxaparin sodium may be present in the formulation at a concentration of about 150 mg per 1 ml.

Other isotonic agents, buffers, antioxidants, anesthetics, suspending and dispersing agents, emulsifying agents and chelating agents are well-known to those in the art. See, for example, Gennaro (ed.), Remington's Pharmaceutical Sciences, 19th Edition (Mack Publishing Company 1995).

Pharmaceutical carriers also include, by way of example and without limitation, ethyl alcohol, polyethylene glycol and propylene glycol for water miscible vehicles and sodium hydroxide, hydrochloric acid, citric acid or lactic acid. Other pharmaceutical carriers are well-known to those in the art. See, for example, Gennaro (ed.), Remington's Pharmaceutical Sciences, 19th Edition (Mack Publishing Company 1995).

The active agents described herein are often formulated using a variety of parameters including by way of example and without limitation, pHI, molarity, % weight/volume, % volume/volume and the like. Other factors considered in the formulation of, stability of, storage of, shipping of active agents include by way of example and without limitation, the gas environment, container material, container color, cap material, cap color, presence of additional aspects, such as antioxidants, stabilizers, photoprotective compounds, protectants, sugars, ion chelators, ion donors or the like. Any factor which serves as any one of the above factors known to one of ordinary skill in the art is often used with the active agents described herein but not limited as such.

The preparation of pharmaceutical or pharmacological compositions are known to those of skill in the art in light of the present disclosure. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants and aerosols are examples of such formulations.

The active agents are often stored at various temperatures, including by way of example and without limitation, freezing, for example at about −20° C., about −70° C., about −100° C., about −120° C., about −150° C., about −200° C. or more than about −200° C., cold storage, for example at about 10° C., about 5° C., about 4° C., about 2° C., about 0° C., about −2° C. or more than about −5° C., or any other suitable temperature such that the composition remains stable.

In some aspects, compositions comprising the compounds described herein are stored as lyophilized solids. In some aspects, the present disclosure provides methods for producing the lyophilized composition, the method comprising providing the composition; and lyophilizing the composition, thereby producing the lyophilized composition.

Using lyophilization, it is possible to store the compounds in a manner that maintains physiological or otherwise optimal pH, isotonicity and stability. Such materials include pH buffers, preservatives, tonicity adjusting agents, anti-oxidants, other polymers (e.g., viscosity adjusting agents or extenders) and excipients to stabilize the labile protein against the stresses of drying and storage of the dried product. Specific illustrative examples of such additives include phosphate, citrate, or borate buffers; thimerosal; sorbic acid; methyl or propyl paraben, and chlorobutanol preservatives; sodium chloride: polyvinyl alcohol, polyvinyl pyrrolidone; mannitol, dextrose, dextran, lactose, sucrose, ethylene diamine tetra-acetic acid, and the like. Suitable formulations, known in the art, (Remington's Pharmaceutical Sciences (latest edition), Mack Publishing Company, Easton, Pa.; Arakawa et al. (1990), supra; Carpenter et al. (1991), supra; and Pikal (1990), supra).

In certain aspects, the pharmaceutically acceptable carrier comprises a reconstitution stabilizer. In other aspects, the reconstitution stabilizer comprises a water-soluble polymer. In additional aspects, the water-soluble polymer is selected from a polaxamer, a polyol, a polyethylene glycol, a polyvinylalcohol, a hydroxyethyl starch, dextran, polyvinylpyrrolidene poly(acrylic acid), or a combination thereof.

The term "reconstitution stabilizer" means any excipient which is capable of preventing aggregation of a reconstituted protein in an aqueous medium. Excipients possessing the necessary characteristics for the present invention are well-known in the art and generally function by the mechanisms of charge repulsion, steric hindrance, hydrophobic binding or specific high-affinity binding to the dried protein. Exemplary excipients include various osmolytes, various salts, water soluble synthetic and natural polymers, surfactants, sulfated polysaccharides, carrier proteins, buffers and the like (Manning et al. (1989), Pharmaceutical Research, 6:903-918; and Paborji, et al. (1994), Pharmaceutical Research, 11:764-771).

The present compounds and an effective amount of the reconstitution stabilizer are admixed under conditions effective to reduce aggregation of present compounds upon reconstitution with the reconstitution medium (e.g., a solvent and optionally other components such as antibacterials). The reconstitution stabilizer may be admixed with the compounds at a suitable time before, during or after reconstitution; preferably the reconstitution stabilizer will be pre-dissolved in the reconstitution medium. The compound is reconstituted at a temperature which is above the freezing point of the reconstitution medium, but which will not degrade the compound and which will not be deleterious to the reconstitution stabilizer; preferably the temperature will be between about 2° C. to 50° C. The time taken to mix the reconstitution stabilizer and the dried compound should be for a sufficient period to prepare a suitable admixture; preferably mixing will be for between about 1 to 30 minutes. Generally, the reconstituted formulation is used soon after reconstitution.

In certain aspects, the present compositions are reconstituted from a lyophilized form. In other aspects, the present disclosure provides methods for producing the reconstituted composition, the method comprising providing a lyophilized composition; and reconstituting the composition with a solution to produce a reconstituted composition. In various aspects, the reconstituting solution comprises water. In some aspects, the reconstituting solution is selected from sterile water, physiological saline solution, glucose solution or other aqueous solvents (e.g., alcohols such as ethyl, n-propyl or isopropyl, butyl alcohol), or a combination thereof, which are capable of dissolving the dried composition and compatible with the selected administration route and which does not negatively interfere with the compound and the reconstitution stabilizers employed.

Applications

An active agent of the present disclosure may be used for various therapeutic applications. An active agent may be administered as a pharmaceutical composition. A pharmaceutical composition of the disclosure can be a combination of any active agent described herein with other chemical components, such as carriers, stabilizers, diluents, dispersing agents, suspending agents, thickening agents, and/or excipients. The pharmaceutical composition facilitates administration of an active agent described herein to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, inhalation, dermal, intra-articular, intrathecal, intranasal, and topical administration. A pharmaceutical composition can be administered in a local or systemic manner, for example, via injection of the active agent described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of an active agent described herein in water-soluble form. Suspensions of active agents described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduces the aggregation of such active agents described herein to allow for the preparation of highly concentrated solutions. Alternatively, the active agents described herein can be lyophilized or in powder form for re-constitution with a suitable vehicle, e.g., sterile pyrogen-free water, before use. In some embodiments, a purified active agent is administered intravenously.

An active agent of the disclosure can be applied directly to an organ, or an organ tissue or cells, during a surgical procedure. In some embodiments, an active agent may be applied directly to a cancerous tissue (e.g., a tumor). The active agents described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the active agent described herein described herein are administered in pharmaceutical compositions to a subject suffering from a condition. In some instances the pharmaceutical composition will affect the physiology of the animal, such as the immune system, inflammatory response, or other physiologic affect. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising an active agent described herein can be manufactured, for example, by expressing the active agent in a recombinant system, purifying the active agent, lyophilizing the active agent, mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of active agents described herein include formulating the active agent described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

"Product" or "dosage form" as used herein refers to any solid, semi-solid, lyophilized, aqueous, liquid or frozen formulation or preparation used for administration. Upon administration, the rate of release of an active moiety from a product is often greatly influenced by the excipients and/or product characteristics which make up the product itself. For example, an enteric coat on a tablet is designed to separate that tablet's contents from the stomach contents to prevent, for example, degradation of the stomach which often induces gastrointestinal discomfort or injury. According to the currently accepted conventional understanding, systemic exposure of the active moiety will be relatively insensitive to the small formulation changes.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

An active agent of the present disclosure may be administered to a patient in an effective amount. The term "effective amount," as used herein, can refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. Compositions containing such agents or compounds can be administered for prophylactic, enhancing, and/or therapeutic treatments. An appropriate "effective" amount in any individual case can be determined using techniques, such as a dose escalation study.

The methods, compositions, and kits of this disclosure can comprise a method to prevent, treat, arrest, reverse, or ameliorate the symptoms of a condition. The treatment can comprise treating a subject (e.g., an individual, a domestic animal, a wild animal or a lab animal afflicted with a disease or condition) with an active agent of the disclosure. Active agents of the present disclosure may be administered to treat a disease in a subject. The subject can be a human. A subject can be a human; a non-human primate such as a chimpanzee, or other ape or monkey species; a farm animal such as a cattle, horse, sheep, goat, swine; a domestic animal such as a rabbit, dog, and cat; a laboratory animal including a rodent, such as a rat, mouse and guinea pig, or the like. A subject can be of any age. A subject can be, for example, an elderly adult, adult, adolescent, pre-adolescent, child, toddler, infant, or fetus in utero.

Treatment can be provided to the subject before clinical onset of disease. Treatment can be provided to the subject after clinical onset of disease. Treatment can be provided to the subject after 1 day, 1 week, 6 months, 12 months, or 2 years or more after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment can also include treating a human in a clinical trial. A treatment can comprise administering to a subject a pharmaceutical composition, such as one or more of the pharmaceutical compositions described throughout the disclosure. A treatment can comprise a once daily dosing. A treatment can comprise delivering an active agent of the disclosure to a subject, either intravenously, subcutaneously, intramuscularly, by inhalation, dermally, intra-articular injection, orally, intrathecally, transdermally, intranasally, via a peritoneal route, or directly onto or into a diseased tissue, e.g., via topical, intra-articular injection route or injection route of application.

In some embodiments, the present disclosure provides a method for treating a cancer, the method comprising administering to a subject in need thereof an effective amount of an active agent of the present disclosure.

In some embodiments, the present disclosure provides a method for treating a cancer, the method comprising administering to a patient in need thereof an effective amount of a pharmaceutical composition comprising an active agent of the present disclosure and a pharmaceutically acceptable carrier.

Kits

An active agent of the present disclosure may be provided in various kits. In some embodiments, pharmaceutical compositions comprising an active agent of the present disclosure may be supplied as a kit. A kit may comprise a container that comprises an active agent. Therapeutic active agents can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic active agents. Such a kit may further comprise written information on indications and usage of the pharmaceutical composition.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

EXAMPLES

The following examples are illustrative and non-limiting to the scope of the compositions, methods, systems, and kits described herein.

Example 1

Administration of Heparin and N-Acetylcysteine to Treat a Coronavirus Infection

This example describes treatment of a coronavirus infection by administering heparin and N-acetylcysteine to a subject. A human subject having a coronavirus infection and breathing with assistance of a ventilator is administered by inhalation a composition comprising heparin and N-acetylcysteine. A composition comprising 1.5 g of sodium N-acetylcysteine and 22,000 international standard units (IU) of sodium heparin in a volume of 6 milliliters (mL) is administered through the side port of the mechanical ventilator using a nebulizer. The composition is administered continuously for 8 hours. The subject is administered three 6 mL doses per day such that 18 mL of the composition, comprising a total of 4.5 g of sodium N-acetylcysteine and 66,000 IU of heparin are administered over the course of 24 hours. The composition is administered to the subject for up to 7 days (up to forty-two 6 mL doses) or until the subject is weaned from mechanical ventilation, whichever is sooner. The maximum length of treatment is 7 days of 3 doses per day or 462,000 IU of heparin and 31.5 g of NAC.

The length of stay in the intensive care unit of subjects receiving sodium N-acetylcysteine and sodium heparin is decreased compared to subjects not receiving sodium N-acetylcysteine and sodium heparin. The mortality rate of subjects receiving sodium N-acetylcysteine and sodium heparin is decreased compared to subjects not receiving sodium N-acetylcysteine and sodium heparin. The lung damage of subjects receiving sodium N-acetylcysteine and sodium heparin, as measured by Lung Injury Score (LIS) is decreased compared to subjects not receiving sodium N-acetylcysteine and sodium heparin. Lung function of subjects receiving sodium N-acetylcysteine and sodium heparin, as measured by daily Oxygenation Index (OI), is increased compared to subjects not receiving sodium N-acetylcysteine and sodium heparin. The incidence of ventilator-associated pneumonia in subjects receiving sodium N-acetylcysteine and sodium heparin is decreased compared to subjects not receiving sodium N-acetylcysteine and sodium heparin.

The number of ventilator-free days is defined as the number of days a patient is breathing without assist of a ventilator during the lesser of total hospital stay or first 28 days; thus, the patient must be free of mechanical ventilation for 24 hours to have one ventilator-free day. Change in the plateau airway pressure during ventilation is decreased from the baseline (day 0, before randomization and or the start of intervention) to Day 1 and from Day 1 to Day 8 after the administration of heparin and N-acetylcysteine. Change in volume of the lungs per change in pressure during ventilation is improved from the baseline (day 0, before randomization and or the start of intervention) to Day 1 and from Day 1 to Day 8 after the administration of heparin and N-acetylcysteine.

Exclusion criteria include: receiving invasive ventilation >24 hours, expected duration of mechanical ventilation <24 hours, chronic obstructive pulmonary disease GOLD stage III and IV, any history of pulmonary hemorrhage in the past 3 months, any history of significant bleeding disorder, known allergy to heparin, including heparin-induced thrombocytopenia, pregnancy or breast feeding, unlikely to survive for >72 hours, serious basic diseases affecting survival, including: uncontrolled malignant tumor with multiple metastases that cannot be removed, hematological diseases, cachexia, active hemorrhage, severe malnutrition, AIDS, etc., Obstructive pneumonia, severe pulmonary interstitial fibrosis, alveolar proteinosis and allergic alveolitis caused by lung tumor, use in vitro life support, patients with bronchial asthma, peptic ulcer, and patients allergic to acetylcysteine, or any potential violation of test compliance or any other circumstance affecting safety and effectiveness evaluation that may exist, which the researchers believe is not suitable for patients participating in the study.

Example 2

Clinical Trial for Nebulized Heparin and N-Acetylcysteine in Patients with SARS-COV-2 on Mechanical Ventilation This example describes a clinical trial for nebulized heparin and N-Acetylcysteine in patients with SARS-COV-2 on mechanical ventilation. After obtaining institution medical board approval and written informed consent from patients or their next of kin, patients are enrolled to this prospective randomized, double-blinded trial. Patients included in the study are adults older than 18 years with a diagnosis of SARS-COV-19 infection and require mechanical ventilation.

Exclusion criteria include the following: pregnancy, hypersensitivity to heparin (including heparin induced thrombocytopenia, defined as platelet count below 50,000/mm³) or to N-acetylcysteine (NAC), severe cardiorespiratory, renal or hepatic comorbidities, uncontrolled bleeding, significant bleeding disorders, and inability to obtain informed consent. All patients are assessed by Acute Physiology and Chronic Health Evaluation (APACHE) II score.

All patients are ventilated initially with volume cycled ventilation, using a tidal volume of 5 to 7 mL/kg, so that peak airway pressure does not exceed 35 cm H₂O. Positive end-expiratory pressure (PEEP) is adjusted to achieve PaO₂ of 55 to 80 mmHg or SpO₂ of 88% to 95% using minimal fraction of inspired oxygen (FIO₂). Lung injury score (LIS) components are obtained for the study groups after admission and before changes are made to the ventilator settings every morning during the first 7 days. LIS is calculated from its components and used as the primary outcome.

Patients are randomized into 5 groups using a computer generated randomization list: group A receives 3 mL saline nebulized, continuously; group B receives alternatively heparin, 10,000 IU heparin sulfate diluted in 3 mL 0.9% saline, nebulized over two hours followed by 3 mL saline nebulized every two hours and repeating; group C receives alternatively N-acetylcysteine (NAC) diluted in 3 mL of 0.9% saline, nebulized over two hours followed by 3 mL saline nebulized every two hours and repeating; group D receives alternatively heparin and NAC nebulized at above concentrations and rates, alternating; group E receives heparin and NAC together in the same vehicle nebulized over two hours followed by two hours of nebulized saline and then repeating.

Administration of the study medications and assessing the scores is performed by investigators who are unaware of patients' allocation.

Coagulation parameters including APTT, TCT, international normalized ratio, and platelet count are followed up daily, and APTT more than 64 seconds, TCT more than 40 seconds, international normalized ratio above 1.5, or platelets count less than 50,000/mm³ are indications to stop heparin. Evidence of blood staining of respiratory secretions are assessed by the bedside nurses caring for the cases who were blinded to the study medications. Weaning is done using spontaneous pressure support mode of mechanical ventilation and adjusted to maintain the target tidal volume. Extubation is considered in cooperative hemodynamically stable patients with oxygen saturation of at least 95% on pressure support mode of ventilation less than 10 cm H₂O, PEEP less than 5 cm H₂O, and FIO₂ less than 0.5.

Tracheostomy is considered if patients are not suitable for extubation after 7 days of mechanical ventilation and show no clinical improvement. It is expected that group B will have a statistically significantly reduced time duration of mechanical ventilation, reduced ICU time, reduced mortality, and more rapid clearance of SARS-COV-19 virus titers.

Example 3

Clinical Trial for Face Mask Nebulized Heparin and N-Acetylcysteine in Patients with SARS-COV-2 not Receiving Mechanical Ventilation This example describes a clinical trial for face mask nebulized heparin and N-Acetylcysteine in patients with SARS-COV-2 not receiving mechanical ventilation. After obtaining institution medical board approval and written informed consent from patients or their next of kin, patients are enrolled to this prospective randomized, double-blinded trial. Patients included in the study are hospitalized adults older than 18 years with a diagnosis of SARS-COV-19 infection and who do not require mechanical ventilation.

Exclusion criteria include the following: pregnancy, hypersensitivity to heparin (including heparin induced thrombocytopenia, defined as platelet count b50,000/mm³) or NAC, severe cardiorespiratory, renal or hepatic comorbidities, uncontrolled bleeding, significant bleeding disorders, and inability to obtain informed consent. All patients are assessed by Acute Physiology and Chronic Health Evaluation (APACHE) II score.

Patients are randomized into 2 groups using a computer generated randomization list: group A receives saline nebulized via face mask continuously; group B receives the formulation, dosing, and timing identified above in the mechanical ventilation patient study.

Administration of the study medications and assessing the scores are performed by investigators who are unaware of patients' allocation. It is expected that group B will have a statistically significantly reduced time duration of hospitalization, reduced progression to the ICU, reduced mortality, and more rapid clearance of SARS-COV-19 virus titers.

Example 4

Safety and Efficacy of Nebulized Heparin and NAC in Normal Subjects

This example describes the safety and efficacy of nebulized heparin and NAC in normal subjects. A Phase 1 clinical study of nebulized heparin is conducted to investigate the safety of increasing doses of a well-defined lower respiratory tract (LRT) dose of inhaled heparin with regard to pulmonary function and coagulation. Ten volunteers inhale heparin from Sidestream jet nebulizers loaded with 100,000, 200,000, 300,000 or 400,000 International Units (ID) of heparin. Lung function, antifactor (anti)-Xa, activated partial thromboplastin time (APTT), tissue factor pathway inhibitor (TFPI), whole blood clotting time, platelets, von Willebrand factor, and C-reactive protein are determined before and 1, 3, 6, and 24 hours after inhalation. The highest LRT dose is 32,000 ID heparin. Inhaled heparin did not affect pulmonary function. The area under the curve of the anti-Xa activity increase with increasing doses of heparin, but remains unchanged for all other variables. Peak anti-Xa activity is 0.113 ID/mL 6 h after inhalation of 400,000 ID heparin. When compared to baseline values: anti-Xa increases after 200,000, 300,000, and 400,000 ID heparin; APTT increases to a maximum of 1.03 6 h after inhalation of 400,000 ID heparin (p=0.05); TFPI increases after 100, 000, 200,000, 300,000 and 400,000 IU.

Inhaled heparin delivery of 32,000 International Units (IU) to the lower respiratory tract can safely be inhaled for clinical or research purposes.

Example 5

Safety and Efficacy of Nebulized Heparin and NAC in Hospitalized Burn Patients with Inhalation Injury This example describes the safety and efficacy of nebulized heparin and NAC in hospitalized burn patients with inhalation injury. Inhalation injury is a major cause of morbidity and mortality in patients with burns. Presence of airways injury adds to the need of fluid supplementation, increases risk of pulmonary complications. Due to many mechanisms involved in pathophysiology the treatment is complex. Among them the formation of fibrin casts inside airways constitutes a prominent element. The material residing in tracheobronchial tree causes ventilation-perfusion mismatch, complicates mechanical ventilation, provides a medium for bacterial growth. Inhaled anticoagulation regimens employing heparin in management of inhalation injury are tested. Simultaneously safety, especially in connection with possible bleeding risk, is measured. Inhalation of heparin and HAC shows positive impact on treatment results with low risk of side effects.

Data are collected in patients receiving nebulized heparin and in historical controls. Data is analyzed separately with 1) all subjects included and 2) with subjects who died/were discharged on the ventilator excluded. Patients receiving nebulized heparin demonstrated a decrease in median (interquartile range) duration of initial mechanical ventilation compared with controls. Patients in the heparin group have increased number of median (interquartile range) ventilator-free days in the first 28 days. There are no differences in hospitalization length, lung injury score during the first 7 days post injury, 28-day mortality, ventilator-associated pneumonia rate, or bleeding events. Nebulized heparin 10,000 units in conjunction with a beta-agonist and mucolytic produces a significant decrease in duration of mechanical ventilation and increase in ventilator-free days in adult patients with IHI. Nebulized heparin is safe and did not result in an increase in bleeding events. Evaluation is performed on at least 50 subjects per treatment group.

Example 6

Safety and Efficacy of Nebulized Heparin and NAC in Patients with Inhalation Injury This example describes the safety and efficacy of nebulized heparin and NAC in patients with inhalation injury. Pneumonia, inhalation trauma and acute respiratory distress syndrome (ARDS), typical causes of lung injury in critically ill patients, are all three characterized by dysregulated inflammation and coagulation in the lungs. Nebulized anticoagulants have beneficial effects and attenuate pulmonary coagulopathy and decrease pulmonary inflammation.

Nebulized anticoagulants attenuate pulmonary coagulopathy in preclinical studies using various models for lung injury. Effects on inflammation are less consistent. Nebulized heparin, danaparoid, and TFPI reduce systemic coagulation, but APC and AT no not.

Nebulized heparin has an anticoagulant effect in the lungs in the presence of pulmonary infection or lung injury. Nebulized heparin also inhibits pulmonary inflammation in the presence of pulmonary infection or lung injury. Nebulized heparin also affects various physiologic parameters and other outcomes, in particular during pulmonary infection and inhalation trauma. Nebulized heparin does not cause systemic bleeding, indicating the safety of the treatment.

Nebulized heparin in combination with N-acetylcysteine and a bronchodilator is tested in patients with inhalation trauma. Nebulized heparin and NAC is associated with physiologic improvements. Nebulized heparin and NAC is associated with shorter duration of ventilator support and reduced mortality. It does not affect systemic coagulation or result in more systemic bleedings.

Reduction of pulmonary coagulopathy at dosages ≥400,000 U/day heparin is observed. Nebulized heparin does not affect physiological parameters, such as arterial oxygenation or pulmonary compliance. Systemic coagulation is affected at dosages ≥100,000 U but without affecting bleeding incidences.

A single dosage of nebulized heparin prior to cardiopulmonary bypass surgery decreases atelectasis and improves $CO_2$ elimination directly after the operation. Nebulized heparin increases the number of ventilator-free days following administration. Nebulized heparin does not increase mortality. Nebulized heparin affects systemic coagulation but does not result in differences in systemic bleedings.

Nebulized heparin and NAC are tested in patients with abnormal, viscid, or inspissated mucus secretions in such conditions as: Chronic bronchopulmonary disease (chronic emphysema, emphysema with bronchitis, chronic asthmatic bronchitis, tuberculosis, bronchietasis, and primary amyloidosis of the lungs); Acute bronchopulmonary disease (pneumonia, bronchitis, tracheobronchitis); Pulmonary complications of cystic fibrosis; Tracheostomy care; Pulmonary complications associated with surgery; Use during anesthesia; Post-traumatic chest conditions; Atelectasis due to mucus obstruction; Diagnostic bronchial studies (bronchograms, bronchospirometry, and bronchial wedge catheterization).

After administration of N-acetylcysteine, airways of patients are maintained by mechanical suction if necessary when a cough is inadequate. When there is a mechanical block due to foreign body or local accumulation, the airway is cleared by endotracheal aspiration with or without bronchoscopy. Asthmatics undergoing treatment are carefully monitored. Patients with bronchospasm are quickly relieved by the use of a bronchodilator administered by nebulization. If bronchospasms progress, medication is discontinued.

Antibiotic agents such as tetracycline hydrochloride, oxytetracycline hydrochloride, and erythromycin lactobionate may be administered to the patient in a solution separate from heparin and N-acetylcysteine.

Example 7

Inhibition of SARS-COV-2 Infectivity in VERO Cells by Heparin and N-Acetylcysteine This example describes inhibition of SARS-COV-2 infectivity in VERO cells. SARS-CoV-2 infectivity of VERO cells were inhibited by heparin and N-acetylcysteine at concentrations which were not cytotoxic. Incubation of SARS-COV-2 with LMWH at 125 μM before VERO cell exposure, the mode for testing antibody activity, showed complete inhibition of SARS-COV-2 infectivity, well below the expected pulmonary delivery dose. For comparison, the concentration of remdesivir needed for a similar level of inhibition was over 600-times higher than is expected to be achieved clinically. N-acetylcysteine was also effective in inhibiting viral entry at 25 mM, a dose that is ⅕₀th the expected clinical dose. Cytotoxicity was not seen at these concentrations for either drug. A review of non-clinical and clinical data for inhalation therapy of heparin and N-acetylcysteine in adult respiratory distress syndrome (ARDS), asthma, and burn-victim inhalation injury patients identified 12 clinical studies in over 800 patients tested. The systemic toxicity from inhalation of heparin and N-acetylcysteine was analyzed, with a special focus on the anti-coagulant effects of low molecular weight heparin (LMWH). Systemic toxicity was minimal and an improvement in lung function was seen. These results, taken together, support the rapid clinical development of heparin and N-acetylcysteine for the treatment of pulmonary complications in COVID-19 patients.

Low molecular weight heparin (enoxaparin, having an average molecular weight of about 4,500 g/mol), N-acetyl-cysteine, and hydroxychloroquine were obtained from Sigma-Aldrich. VERO cells were used by methods previously described (Shen et al. "Epitope resurfacing on dengue virus-like particle vaccine preparation to induce broad neutralizing antibody." eLife 2018).

For experiments in which infectivity was being tested, either VERO cells in media or SARS-COV-2 viral particles were incubated with potential inhibitors for one hour. Then viral particles were added to VERO cells and incubation continued for up to seven days. Cytotoxicity and viral-induced cytopathological effects were examined by light microscopy.

In order to test if AT-H201 had antiviral activity against SARS-COV-2 the standard VERO cells assay was performed. Test compounds were incubated either with the virus, to simulate antibody-like surface binding, or with the cells, to simulate either cell surface changes or to act intracellularly. Serial dilutions were conducted and the cytopathic effect (CPE) was observed by microscopy. Non-virus related cytotoxicity, if present was also noted.

N-Acetyl-cysteine did not inhibit infectivity when incubated with SARS-COV-2 but at 25 mM was able to completely inhibit infectivity when incubated with cells. On the other hand, LMWH was effective either when incubated with the virus or when incubated with the cells. The expected clinical dose of LMWH and NAC are large multiples of the doses that inhibited SARS-COV-2 in these in vitro experiments and compare favorably to the results seen for hydroxychloroquine and remdesivir.

LMWH at nanomolar concentrations was effectively in completely inhibiting viral cytopathic effects, whether incubated with the virus or with the cells. The concentration of hydroxychloroquine or remdesivir needed for the same level of inhibition was over two-logs higher, as shown in TABLE 3. This is the first published data in which SARS-COV-2 inhibition was achieved with a nanomolar potency.

mg/mL, 2.5 mg/mL, 5 mg/mL, 10 mg/mL or 20 mg/mL low molecular weight heparin. Infectivity in the absence of heparin (0 mg/mL) was tested as a negative control. Effect of heparin on viral infectivity was tested either by pre-treating the VERO cells with heparin or by pre-treating the SARS-COV-2 virus with heparin. For cell pretreatment, VERO cells at $5 \times 10^4$ cells per well were pre-treated with heparin for 1 hour at 37° C., then SARS-COV-2 was added at MOI==0.05 in 10 μL for 1 hour at 37° C. For virus pre-treatment, SARS-COV-2 at MOI=0.05 in 500 μL diluent heparin was incubated for 1 hour at 37° C., then the mixture was added to VERO cells at incubated for 1 hour at 37° C. Virus pre-treatment or cell pre-treatment mixtures were then removed, and fresh medium was added and incubated overnight at 37° C. Fixation was performed in 10% Formalin overnight and treated with 0.5% triton X-100. Human anti-SARS-2 N protein was added at 1 μg/mL and incubated at room temperature for 1 hour. Anti-human-IgG-488 was added at 1:1000 dilution and incubated for 1 hour at room temperature. Cell nuclei were stained with DAPI. The resulting images are shown in FIG. 8.

Figure 8:
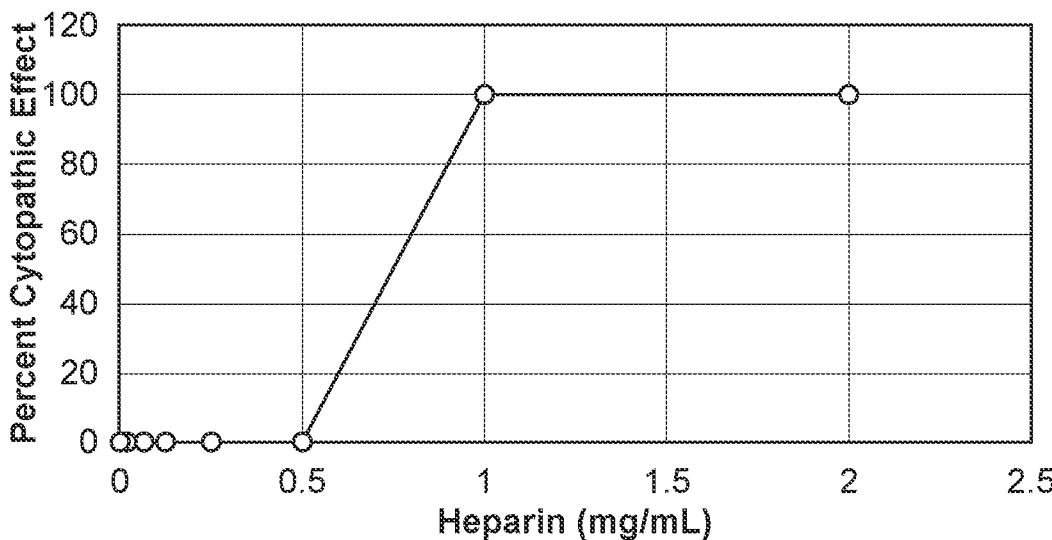
FIG. 8 shows a dose response curve of VERO cells treated with heparin. Test compounds were incubated either with the virus, to simulate antibody-like surface binding, or with the cells, to simulate either cell surface changes or to act intracellularly. Serial dilutions were conducted and the cytopathic effect (CPE) was observed by microscopy. Non-virus related cytotoxicity, if present was also noted.
Figure 9:
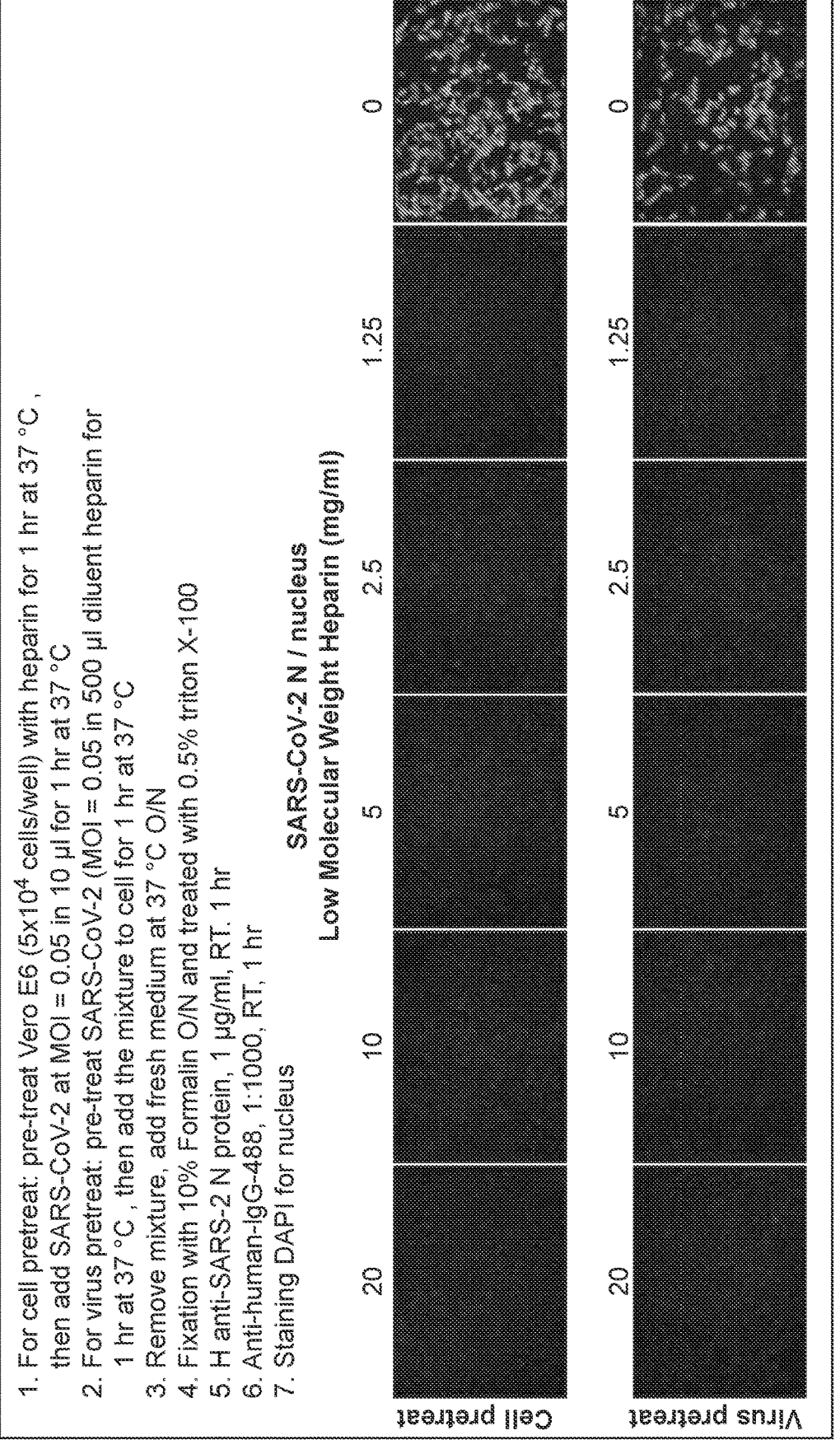
FIG. 9 shows detection of the presence of SARS-COV-2 N protein by immunostaining. VERO cells (top) or SARS-COV-2 (bottom) was pre-treated with low molecular weight heparin (LMWH). Pre-treatment of either cells or virus was capable of preventing viral replication.

Based on the in vitro activity of heparin, as shown in FIG. 8 and FIG. 9, and N-acetylcysteine, as shown in TABLE 4, in potently inhibiting SARS-COV-2 infectivity in VERO cells, a standard model for testing potential pharmaceuticals as anti-viral agents together with the demonstrated non-clinical animal and clinical studies of the drug combination the development of this treatment by the inhalation/nebulized route should be encouraged.

Based on a biophysical approach to SARS-COV-2 envelope protein features, host cell surface proteins and glycans, and their interactions, heparin and NAC may be able to block virus entry and prevent infectivity. In vitro testing of infectivity in VERO cells showed that LMWH can inhibit SARS-COV-2 infectivity with nanomolar efficacy and the most potent SARS-COV-2 inhibitor identified to date.

TABLE 3

Inhibition of Virus Infection by Test Compounds

| Test Compound | Incubation Conditions | Inhibition of Virus Infection | Clinical Dose/ In Vitro Effective Dose | Source |
|---|---|---|---|---|
| LMWH | Both with virus and with VERO cells | 100% at 150 μM | >5 | This study |
| NAC | With cells | 100% at 25 mM | >50 | This study |
| Hydroxychloroquine | With cells | 100% at 16 μM | <0.1 | This study |
| Remdesivir | With cells | 100% at 100 μM | <0.1 | Choy K-T, et al. Antiviral Research, 178 (2020); Sheahan et al., 2017 |

FIG. 8 shows the dose response for heparin in the microscopic cytopathic assay. The cytopathic effect induced by SARS-COV-2 on VERO cells was measured in the presence of increasing concentrations of heparin, up to 2 mg/mL. 100% cytopathic effect was seen in the presence of heparin concentrations at or above 1 mg/mL. Finally, in an assay examining the presence of SARS-COV-2 N protein in cells by immunostaining, pretreatment of either the VERO cells or SARS-COV-2 with LMWH (average molecular weight 4,500 g/mol) was capable of preventing all virus replication. Test conditions and results are shown in FIG. 9. Infectivity of SARS-COV-2 was measured in the presence of 1.25

Example 8

Safety and Efficacy of Inhaled Enoxaparin Alone or in Combination with N-Acetylcysteine for Treatment of COVID-19

This example describes a clinical trial to evaluate the safety, tolerability, and efficacy of inhaled enoxaparin (a low molecular weight heparin), alone or in combination with N-acetylcysteine, for treatment of COVID-19. The study is performed in healthy human volunteers and human patients hospitalized with COVID-19.

| Enoxaparin Formulation for Inhalation Enoxaparin: 100 mg per 1 mL injection syringe |
| --- |
| 100 mg per 1 mL enoxaparin sodium* |
| Water |
| Store protected from light, below 25° C. |

*Approximate anti-Factor Xa activity of 10,000 IU per 100 mg, based on reference to the W.H.O. First International Low Molecular Weight Heparin Reference Standard.

TABLE 5

| N-Acetylcysteine Formulation for Inhalation N-acetylcysteine: 2000 mg per 10 mL acetylcysteine solution for inhalation |
| --- |
| 20% (w/v) acetylcysteine (200 mg per 1 mL) |
| Disodium edetate |
| Sodium hydroxide |
| Water |
| Store protected from light, below 25° C. |

In a first part, enoxaparin is administered to healthy human volunteers by inhalation via nebulization, and the safety, tolerability, and pharmacokinetics of the enoxaparin are assessed. Twelve healthy male or female volunteers are randomized to receive single ascending doses of inhaled enoxaparin or placebo at a ratio of 3:1 in a total of 3 cohorts, with 4 participants per cohort. Nebulized saline is used as the placebo. Enoxaparin is administered by inhalation via nebulization at 0.5 mg/kg (about 50 IU/kg), 1 mg/kg (about 100 IU/kg), or 2 mg/kg (about 200 IU/kg) per dose. Participants receive a single dose of inhaled enoxaparin or placebo.

In a second part, enoxaparin is administered to healthy human volunteers by inhalation via nebulization, and the safety, tolerability, and pharmacokinetics of the enoxaparin are assessed. Eight healthy male or female volunteers are randomized to receive multiple ascending doses of inhaled enoxaparin or placebo at a ratio of 3:1 in a total of 2 cohorts, with 4 participants per cohort. Nebulized saline is used as the placebo. Enoxaparin is administered by inhalation via nebulization at 0.5 mg/kg or 1 mg/kg per dose. Participants receive a single dose of inhaled enoxaparin or placebo every 12 hours (±15 minutes) for 7 days.

In a third part, enoxaparin is administered via inhalation using a multiple dose schedule in combination with inhaled N-acetylcysteine to healthy human volunteers. The safety, tolerability, and pharmacokinetics of the enoxaparin and N-acetylcysteine combination treatment are assessed. Twelve healthy male or female volunteers are randomized to receive single and multiple ascending doses of inhaled enoxaparin or placebo plus inhaled N-acetylcysteine at a ratio of 2:1 in a total of 2 cohorts, with 6 participants per cohort. Nebulized saline is used as the placebo. Enoxaparin is administered by inhalation via nebulization at 0.5 mg/kg or 1 mg/kg per dose. N-acetylcysteine is administered by inhalation via nebulization at 600 mg per dose. Participants receive a single dose of N-acetylcysteine on study Day 1. Participants receive a single dose of inhaled enoxaparin or placebo on study Day 2. Participants receive a single dose each of inhaled enoxaparin or placebo followed by inhaled N-acetylcysteine 30 minutes (±5 minutes) after the enoxaparin or placebo on study Day 3. Participants receive inhaled enoxaparin or placebo every 12 hours (±15 minutes) and N-acetylcysteine every 6 hours (±15 minutes), with every other dose administered 30 minutes (±5 minutes) after enoxaparin or placebo, for 7 days starting on study Day 4.

In a fourth part, enoxaparin is administered via inhalation as an adjunct to inhaled N-acetylcysteine to human COVID-19 patients with moderate illness. The safety, tolerability, and efficacy of the enoxaparin and N-acetylcysteine combination treatment are assessed. Twelve male or female COVID-19 confirmed patients are randomized to receive inhaled enoxaparin or placebo plus N-acetylcysteine, along with best supportive care, at a ratio of 3:1. Nebulized saline is used as the placebo. Enoxaparin is administered by inhalation via nebulization at a dose level determined from the third part. N-acetylcysteine is administered by inhalation via nebulization at 600 mg per dose. Participants receive inhaled enoxaparin or placebo every 12 hours (±15 minutes) and N-acetylcysteine every 6 hours (±15 minutes), with every other dose administered 30 minutes (±5 minutes) after enoxaparin or placebo, for 7 days.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating a lung injury in a subject in need thereof, the method comprising:
  administering by inhalation a composition comprising a therapeutically effective amount of a heparin and N-acetylcysteine to the subject, thereby treating the lung injury in the subject and showing a physiological improvement, shorter duration of ventilator support, reduced mortality, or any combination thereof.

2. The method of claim 1, wherein the method inhibits a pulmonary inflammation in the subject.

3. The method of claim 1, wherein the method improves a lung function in the subject, as measured by a daily oxygenation index.

4. The method of claim 1, wherein the heparin has an average molecular weight of at least 4 kDa and not more than 5 kDa.

5. The method of claim 1, wherein the heparin is enoxaparin.

6. The method of claim 1, wherein the heparin is administered at a daily dose of at least 10,000 IU and not more than 400,000 IU.

7. The method of claim 1, wherein the N-acetylcysteine is administered at a daily dose of at least 1 g and not more than 30 g.

8. The method of claim 1, wherein the N-acetylcysteine is administered at a daily dose of at least 400 mg and not more than 700 mg.

9. The method of claim 1, wherein the heparin and the N-acetylcysteine are nebulized.

10. The method of claim 1, wherein the method comprises continuously administering the heparin and N-acetylcysteine, over a period of at least 8 hours.

11. The method of claim 1, wherein the method comprises administering the heparin and N-acetylcysteine, at least three times per day.

12. The method of claim 1, wherein the N-acetylcysteine is formulated as an aqueous N-acetylcysteine solution further comprising disodium edetate.

13. The method of claim 12, wherein the aqueous N-acetylcysteine solution has about 200 mg per mL N-acetylcysteine.

14. The method of claim 12, wherein the aqueous N-acetylcysteine solution has not less than 0.1 mg per mL and not more than 5 mg per mL disodium edetate.

15. The method of claim 1, wherein the heparin is formulated as an aqueous heparin solution.

16. The method of claim 15, wherein the aqueous heparin solution comprises about 100 mg per mL heparin.

\* \* \* \* \*